United States Patent
Fu et al.

(10) Patent No.: US 11,642,362 B2
(45) Date of Patent: May 9, 2023

(54) METHODS OF INHIBITING CELL PROLIFERATION AND METTL8 ACTIVITY

(71) Applicant: NATIONAL UNIVERSITY OF SINGAPORE, Singapore (SG)

(72) Inventors: Xin-Yuan Fu, Singapore (SG); Xinyu Liu, Singapore (SG); Lu Ang Xu, Singapore (SG)

(73) Assignee: NATIONAL UNIVERSITY OF SINGAPORE, Singapore (SG)

(*) Notice: Subject to any disclaimer, the term of this patent is extended or adjusted under 35 U.S.C. 154(b) by 314 days.

(21) Appl. No.: 16/628,597

(22) PCT Filed: Jul. 6, 2018

(86) PCT No.: PCT/SG2018/050337
§ 371 (c)(1),
(2) Date: Jan. 3, 2020

(87) PCT Pub. No.: WO2019/009813
PCT Pub. Date: Jan. 10, 2019

(65) Prior Publication Data
US 2020/0222444 A1    Jul. 16, 2020

(30) Foreign Application Priority Data
Jul. 6, 2017    (SG) ........................... 10201705556X

(51) Int. Cl.
| A61K 31/7105 | (2006.01) |
| A61P 35/00 | (2006.01) |
| A61K 31/122 | (2006.01) |
| A61K 31/13 | (2006.01) |
| A61K 31/18 | (2006.01) |
| A61K 31/192 | (2006.01) |
| A61K 31/282 | (2006.01) |
| A61K 31/37 | (2006.01) |
| A61K 31/407 | (2006.01) |
| C12N 15/113 | (2010.01) |
| C12N 15/86 | (2006.01) |
| A61K 45/06 | (2006.01) |

(52) U.S. Cl.
CPC ........ *A61K 31/7105* (2013.01); *A61K 31/122* (2013.01); *A61K 31/13* (2013.01); *A61K 31/18* (2013.01); *A61K 31/192* (2013.01); *A61K 31/282* (2013.01); *A61K 31/37* (2013.01); *A61K 31/407* (2013.01); *A61P 35/00* (2018.01); *C12N 15/1137* (2013.01); *C12N 15/86* (2013.01); *A61K 45/06* (2013.01)

(58) Field of Classification Search
CPC ..... A61P 15/00; C12N 15/111; C12N 15/113; C12N 15/1137; C12N 2310/14; C12N 2310/141
USPC ..................... 435/6.1, 91.1, 91.31, 455, 458; 514/44 A, 44 R; 536/23.1, 24.5
See application file for complete search history.

(56) References Cited

PUBLICATIONS

Xu et al (J. Biol. Chem., vol. 292, No. 35, pp. 14,695-14,703 (2017))( (Year: 2017).*
Xiang, G. (Doctoral Thesis, Dept. of Biochemistry, Faculty of Medicine, National Univ. Singapore (2014) (Year: 2014).*
Arnould, Sylvain, et al., "Engineering of Large Numbers of Highly Specific Homing Endonucleases that Induce Recombination on Novel DNA Targets," J. Mol. Biol., vol. 355, 2006, pp. 443-458.
Chonn, Arcadio, et al., "Recent advances in liposomal drug-delivery systems," Current Opinion in Biotechnology, vol. 6, 1995, pp. 698-708.
Donehower, Lawrence A., et al., "Mice deficient for p53 are developmentally normal but susceptible to spontaneous tumours," Nature, vol. 356, 1992, seven (7) pages.
Furtek, Steffanie L., et al., "Strategies and Approaches of Targeting STAT3 for Cancer Treatment," ACS Chemical Biology, vol. 11, 2016, pp. 308-318.
Gu, Hao, et al., "The STAT3 Target Mettl8 Regulates Mouse ESC Differentiation via Inhibiting the JNK Pathway," Stem Cell Reports, vol. 10, 2018, pp. 1807-1820.
International Search Report dated Jan. 2, 2019 issued in International Application No. PCT/SG2018/050337, six (6) pages.
Jacks, Tyler, et al., "Tumor spectrum analysis in p53-mutant mice," Current Biology, vol. 4, 1994, pp. 1-7.
Junxin, Liang, "Functional Characterization of Human Methyltransferase Like Protein 8 in DNA Damage Response," Doctoral Thesis (National University of Singapore, 2014), 141 pages.
Kamran, Mohammad Z., et al., "Role of STAT3 in Cancer Metastasis and Translational Advances," BioMed Research International, vol. 2013, Article ID 421821, 15 pages.
Kemp, George, et al., "Amifostine Pretreatment for Protection Against Cyclophosphamide-Induced and Cisplatin-Induced Toxicities: Results of a Randomized Control Trial in Patients with Advanced Ovarian Cancer," J Clin Oncol, vol. 14, 1996, pp. 2101-2112.
Kubbutat, Michael H.G., et al., "Keeping an old friend under control: regulation of p53 stability," Molecular Medicine Today, Jun. 1998, pp. 250-256.
Kumanohoso, Toru, et al., "Enhancement of therapeutic efficacy of bleomycin by incorporation into biodegradable poly-d, l-lactic acid," Cancer Chemother Pharmacol, 1997, vol. 40, pp. 112-116.

(Continued)

*Primary Examiner* — Jane J Zara
(74) *Attorney, Agent, or Firm* — Foley & Lardner LLP

(57) ABSTRACT

The disclosure provides a method of inhibiting proliferation of a cell, inhibiting m3C formation in a cell, inhibiting activity of Mettl8 in a cell, or activating ATM and p53 in a cell, the method comprising contacting the cell with a Mettl8 inhibitor. The disclosure also provides a composition comprising a cell with a reduced expression or activity of Mettl8. In another aspect, the disclosure provides methods of rendering a tumor cell sensitive to a cancer therapy.

8 Claims, 31 Drawing Sheets
Specification includes a Sequence Listing.

(56) References Cited

PUBLICATIONS

Meek, David W., "Regulation of the p53 response and its relationship to cancer," Biochem J., vol. 469, 2015, pp. 325-346.
Prykhozhij, Sergey V., et al., "CRISPR MultiTargeter: A Web Tool to Find Common and Unique CRISPR Single Guide RNA Targets in a Set of Similar Sequences," PLOS ONE, vol. 10, Issue 3, 2015, eighteen (18) pages.
Schiller, Joan H., et al., "Amifostine, Cisplatin, and Vinblastine in Metastatic Non-Small-Cell Lung Cancer: A Report of High Response Rates and Prolonged Survival," Journal of Clinical Oncology, vol. 14, No. 6, 1996, pp. 1913-1921.
Seligman, Lenny M., et al., "Mutations altering the cleavage specificity of a homing endonuclease," Nucleic Acids Research, 2002, vol. 30, No. 17, pp. 3870-3879.
Sipos, Eric P., et al., "Optimizing interstitial delivery of BCNU from controlled release polymers for the treatment of brain tumors," Cancer Chemother Pharmacol, vol. 39, 1997, pp. 383-389.
Spitzer, Michaela, et al., "E-CRISP: fast CRISPR target site identification," Nature Methods, vol. 11, No. 2, Feb. 2014, pp. 122-123.
Tsuchikama, Kyoji, et al., "Antibody-drug conjugates: recent advances in conjugation and linker chemistries," Protein Cell, vol. 9, Issue 1, 2018, pp. 33-46.
Vousden, Karen H., et al., "Blinded by the Light: The Growing Complexity of p53," Cell, vol. 137, 2009, nineteen (19) pages.
Xiang, Gao, "Biochemical Characterization of a Novel Nuclear Methyltransferase Complex (Revised)," Doctoral Thesis (National University of Singapore, 2014), 113 pages.
Xiao, Yufei, et al., "A novel significance score for gene selection and ranking," Bioinformatics, vol. 30, No. 6, 2014, pp. 801-807.
Xu, Luang, et al., "Three distinct 3-methylcytidine (m3C) methyltransferases modify tRNA and mRNA in mice and humans," J. Biol. Chem., vol. 292, Issue 35, 2017, pp. 14695-14703.
Zhang, Yanping, et al., "Signaling to p53: Ribosomal Proteins Find Their Way," Cancer Cell, vol. 16, 2009, nine (9) pages.
Zhu, Lihua J., et al., "CRISPRseek: A Bioconductor Package to Identify Target-Specific Guide RNAs for CRISPR-Cas9 Genome-Editing Systems," PLOS ONE, vol. 9, Issue 9, Sep. 2014, seven (7) pages.
Zhu, Lihua Julie, "Overview of guide RNA design tools for CRISPR-Cas9 genome editing technology," Front. Biol., vol. 10, Issue 4, 2015, pp. 289-296.
Communication pursuant to Article 94(3) EPC dated Feb. 8, 2022 issued in EP Application No. 18746019.1, 6 pages.
Joerger, Andreas C., et al. "The p53 Pathway: Origins, Inactivation in Cancer, and Emerging Therapeutic Approaches," Annu. Rev. Biochem, 2016, vol. 85, pp. 375-404.
Wasylishen, Amanda R., et al., "Attenuating the p53 Pathway in Human Cancers: Many Means to the Same End," Cold Spring Harbor Perspectives in Medicine, Jun. 21, 2016, vol. 6, No. 8, p. a026211, XP55886223.

\* cited by examiner

Human Mettl8 mRNA NM_024770

| Target | Sequence | Region |
| --- | --- | --- |
| gRNA 1 | TAACTTTTTAGGTACTGCTT | exon2 |
| gRNA2 | CTCAGCTGTGCGAGTCCTTC | exon3 |
| gRNA3 | GAAGGCGAGAGAATCATCAT | exon4 |

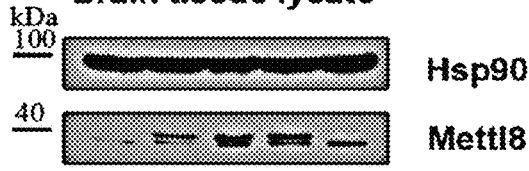

Genes upregulated by Stat3+OSM

Stat3 binding site is conserved in mouse and human

Stat3 binding site

Enrichment of Stat3 binding on human Mettl8 promoter region

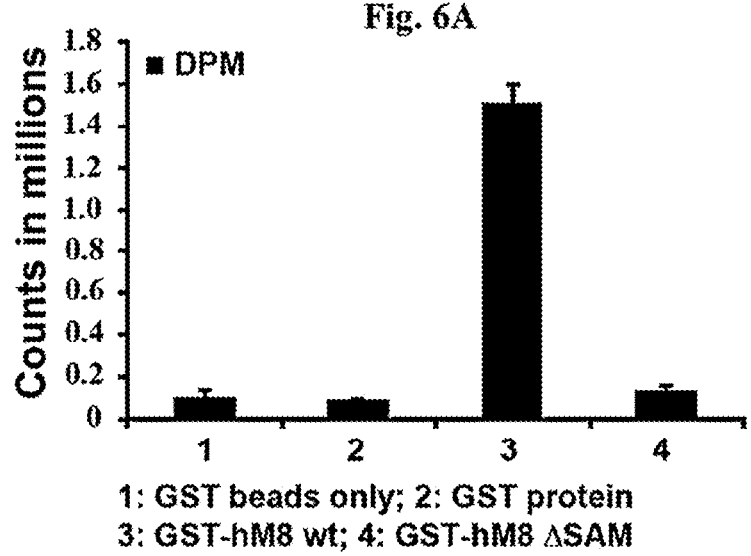
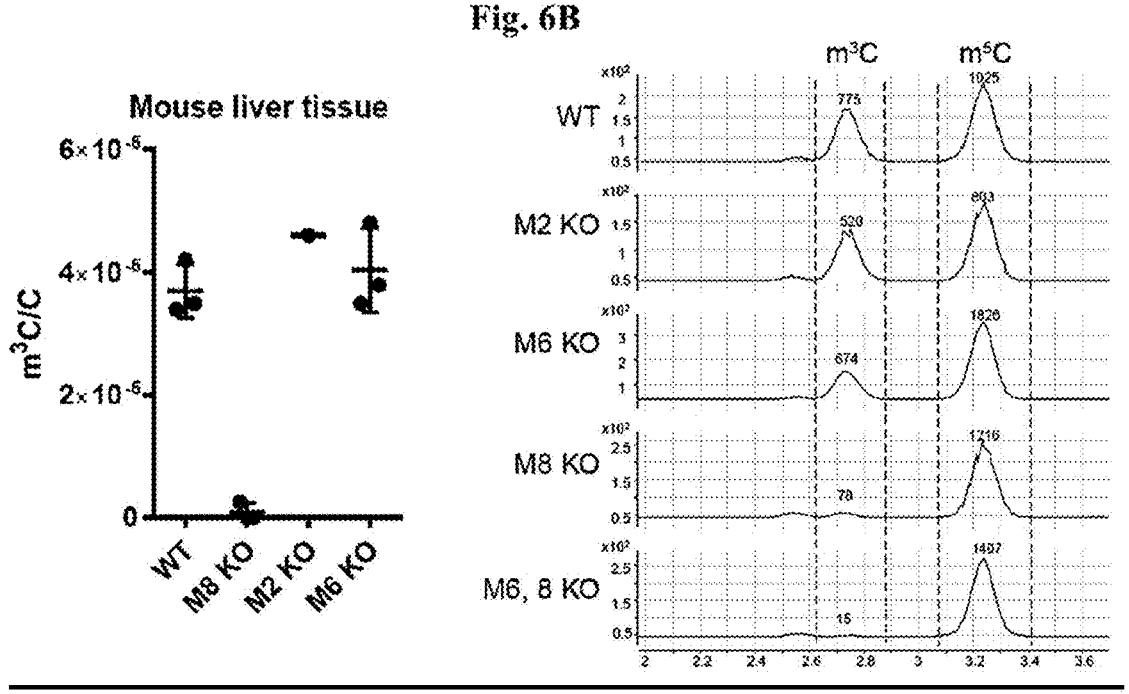

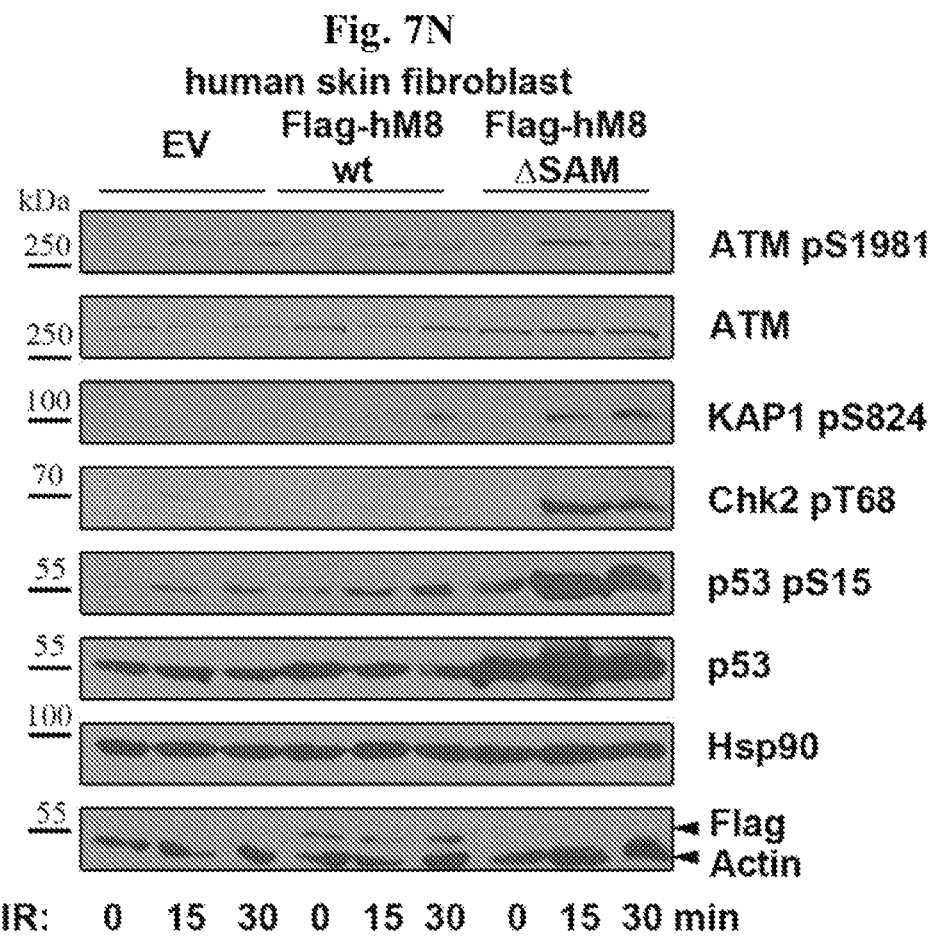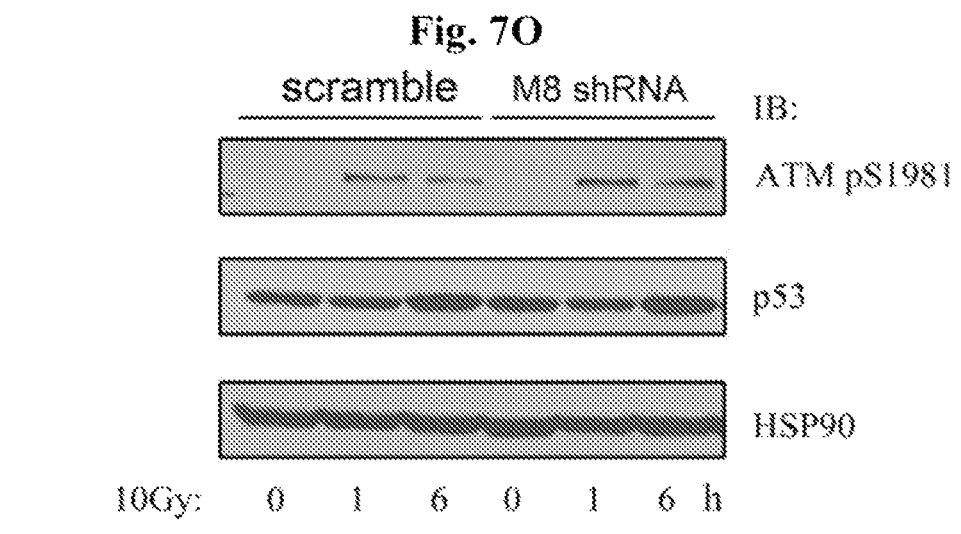

Fig. 8B

| Protein name | Peptides(95%) |
|---|---|
| Nucleolin (NCL) | 30 |
| Heterogeneous nuclear ribonucleoprotein U (HNRNPU) | 21 |
| Nucleolar RNA helicase 2 (DDX21) | 12 |
| Putative ATP-dependent RNA helicase (DHX30) | 12 |
| Insulin-like growth factor 2 mRNA-binding protein 1(IGF2BP1) | 10 |
| Nuclease-sensitive element-binding protein 1 (YBX1) | 9 |
| Interleukin enhancer-binding factor 2 (ILF2) | 5 |
| X-ray repair cross-complementing protein 5 (XRCC5) | 5 |
| Myb-binding protein 1A (MYBBP1A) | 5 |
| X-ray repair cross-complementing protein 6 (XRCC6) | 4 |
| Histone H2A.x (H2AFX) | 3 |
| Transcription intermediary factor 1-beta (TRIM28, KAP1) | 2 |
| Serine/arginine-rich splicing factor 7 (SRSF7) | 2 |
| Elongation factor 1-alpha 1(EEF1A1) | 2 |
| Splicing factor, proline- and glutamine-rich (SFPQ) | 2 |
| DNA topoisomerase 1 (TOP1) | 2 |
| TATA-binding protein-associated factor 2N (TAF15) | 1 |
| Non-POU domain-containing octamer-binding protein (NONO) | 1 |

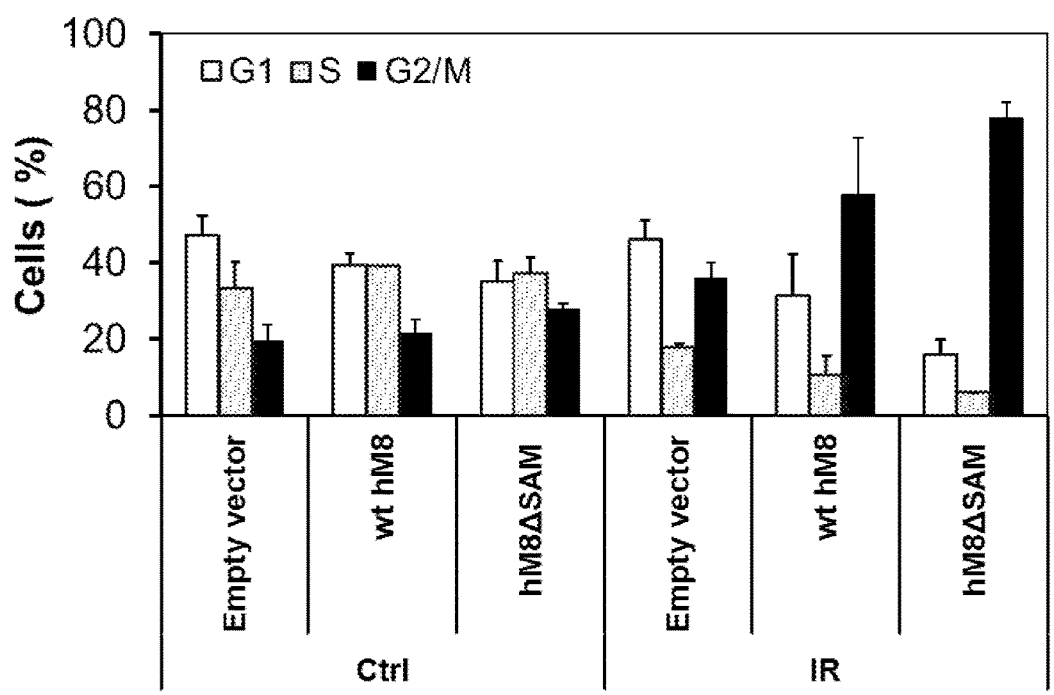
Fig. 9A
Fig. 9B
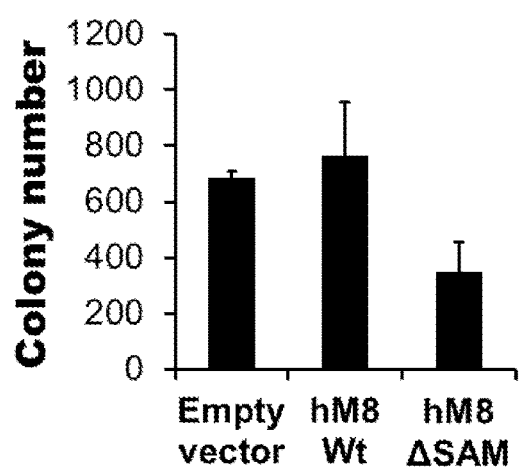
Fig. 9C
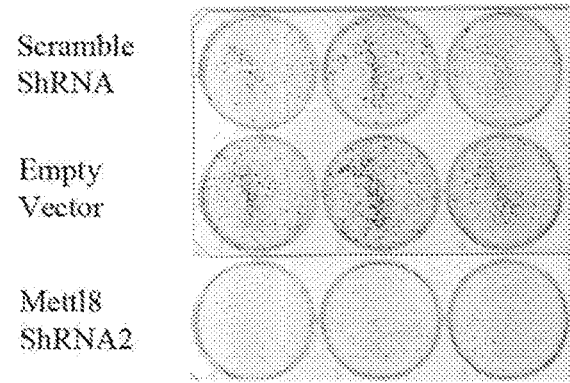

Cisplatin sensitivity_MTS assay

Cisplatin sensitivity colony assay

Cisplatin

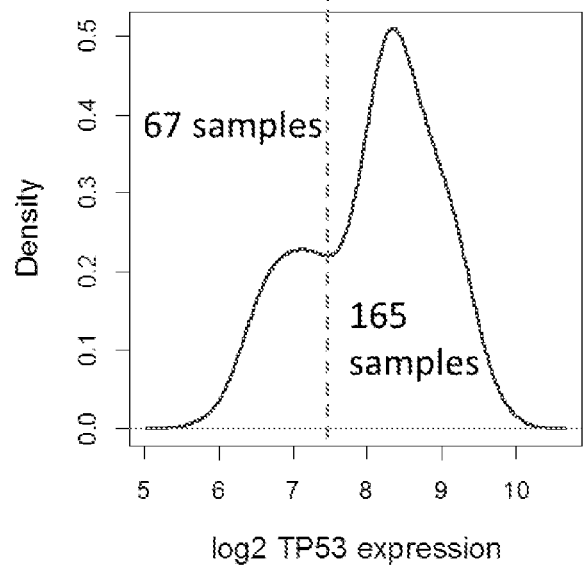
Fig. 11B
All (232) samples without TP53 stratification
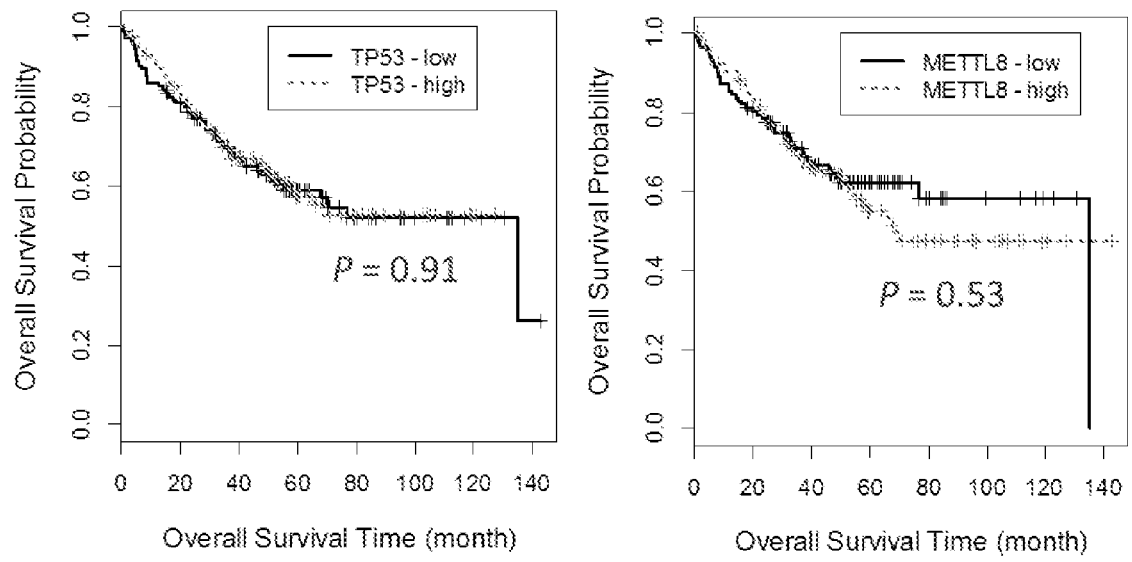

58 samples with low TP53 + 37 samples with TP53 deteriorative mutations 328 samples with TP53 high

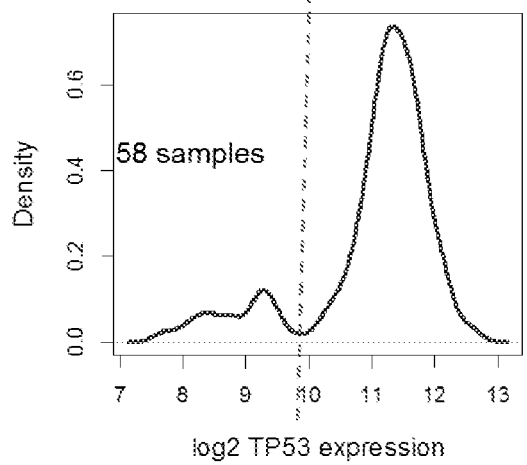
Fig. 11D
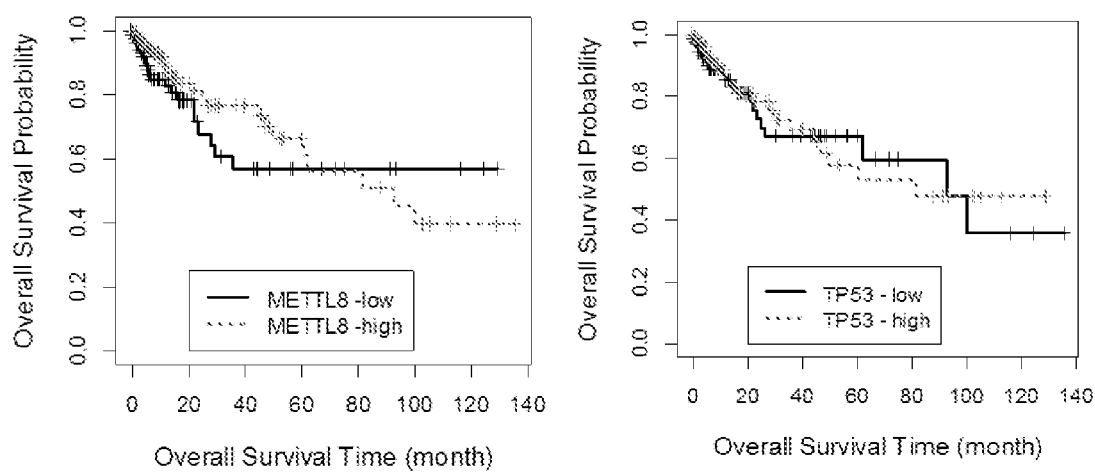
All samples (423) without TP53 stratification

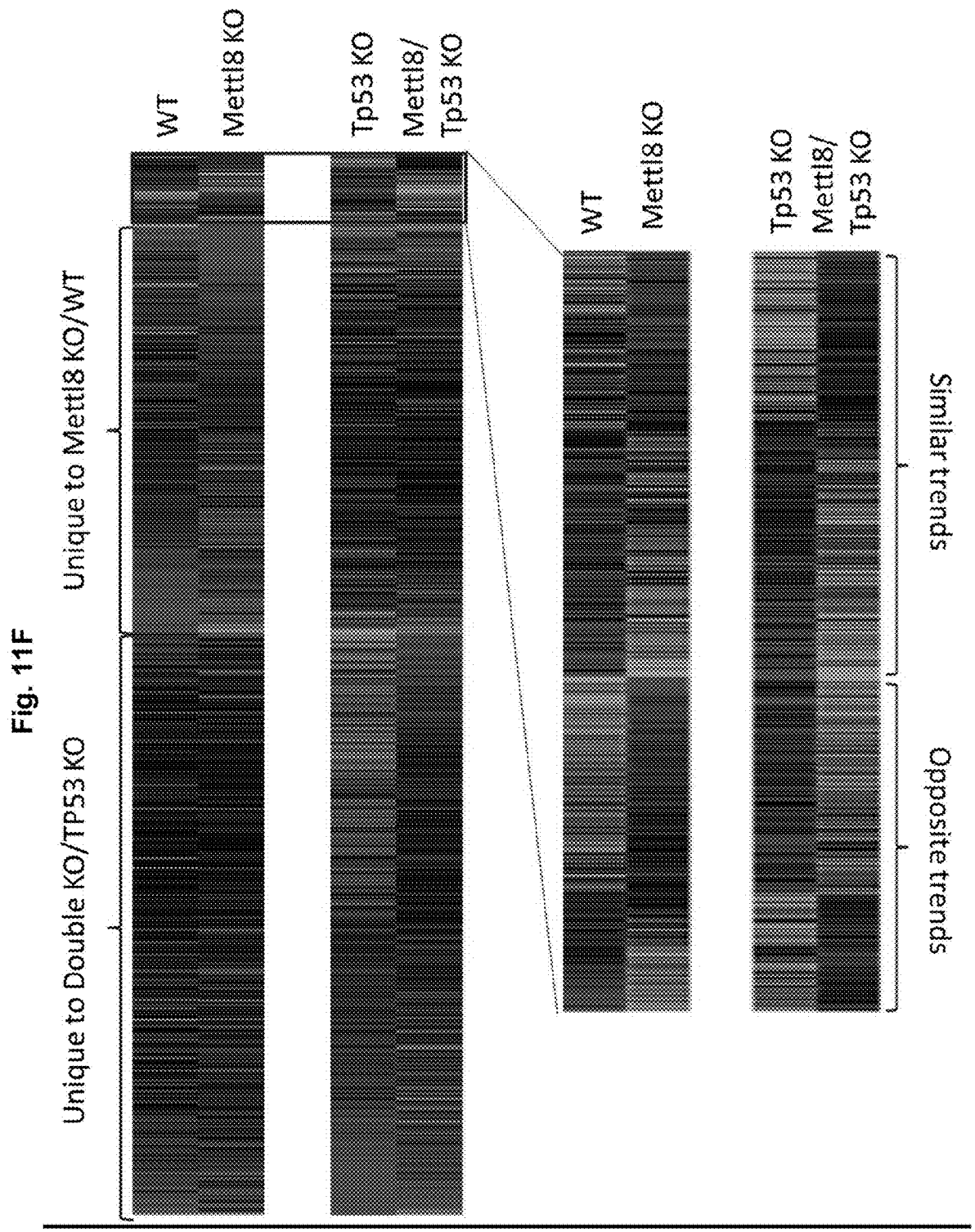

* indicates p<0.05; ** indicates p<0.01 in t-test analysis.

METHODS OF INHIBITING CELL PROLIFERATION AND METTL8 ACTIVITY

CROSS-REFERENCE TO RELATED PATENT APPLICATIONS

This application claims priority of a Singapore Application No. 10201705556X, filed on Jul. 6, 2017. The content of the application is hereby incorporated by reference in its entirety.

SEQUENCE LISTING

The instant application contains a Sequence Listing which has been filed electronically in ASCII format and is hereby incorporated by reference in its entirety. Said ASCII copy, created on Feb. 13, 2020, is named 119617-0138_SL.txt and is 14,536 bytes in size.

BACKGROUND OF THE INVENTION

Cancer is a leading cause of death in most countries, and the result of billions of dollars in healthcare expenses around the world. In 2012, there were about 14 million cancer patients in the world and the patient number is predicted to be 22 million over the next two decades.

TP53 is the most frequently mutated tumor suppressor gene in human cancers. Homozygous p53 knockout mice die largely of spontaneous tumor formation in multiple tissues within half a year (Donehower et al., 1992; Jacks et al., 1994). P53 serves as a master regulator in response to a variety of stresses, such as DNA damage, oncogene activation, ribosomal stress (Zhang and Lu, 2009), hypoxia and ROS (Meek, 2015; Vousden and Prives, 2009). It is tightly regulated at the protein level by its negative regulator MDM2 in a feedback manner to maintain homeostasis under normal physiological conditions. Once activated, p53 executes its tumor suppressor role by inducing cell growth arrest, apoptosis, autophagy, alterations of metabolism, ferroptosis and necrosis through transcription-dependent and/or transcription-independent mechanisms.

P53 is rapidly responsive to DNA damage agents which are still the mainstream cancer therapy. ATM, whose gene product is mutated in a rare human disease, ataxia telangiectasia (A-T), is the critical PI3K like kinase acting as an initial sensor of DNA damage, and can phosphorylate p53 at Sen 5 and MDM2 at Ser429 along many other sites. Subsequently p53 is stabilized via regulation of MDM2-p53 interaction, and phosphorylation is accompanied by p300/PCAF mediated acetylation at its C-terminal stretch, which collectively modulates p53 transactivation ability and turns on downstream target genes required for G1/S checkpoint, apoptosis and many other functions. One well-studied effector is p21 (also called CDKNA1, CIP1) which can suppress Cyclin E/A-dependent Cdk2 activation and prevent G1 to S phase progression. ATM also phosphorylates the checkpoint kinase to further intertwine the complex network via the CHK1/2 mediated phosphorylation on p53 as well as MDM2, cell cycle regulator Cdc25. ATM knockout mice mimic the human A-T patient in terms of cancer susceptibility, hypersensitivity to irradiation, and immune deficiency. DNA damage response is thus recognized as a barrier for tumor growth. Besides p53 and MDM2, ATM also phosphorylates a plethora of substrates of DNA damage response pathways that aim to prevent the genome instability.

Besides the canonical regulation of ATM by multiple factors such as γH2AX, MRN complex which help recruit ATM to double strand break sites and promote its activation, R-loops has been recently recognized as a factor contributing to ATM activation and genome instability. By definition, they are physiological structures consisting of an RNA-DNA hybrid and displaced single-stranded DNA, which regulate various cellular processes such as transcription, DNA replication. R-loops, consisting of an RNA-DNA hybrid and displaced single-stranded DNA, are physiological structures that regulate various cellular processes such as transcription, DNA replication. R-loops tend to form or be stabilized at certain DNA structural features such as negative DNA supercoiling, the formation of G-quartets in the displaced ssDNA. Intriguingly, changes in R-loop dynamics have also been associated with DNA damage accumulation and genome instability which could result in ATM activation via non-canonical manner. In yeast, the loss of DNA topoisomerase (TOP) 1 and 2 increases R-loop accumulation at the rDNA locus. Human TOP1-deficient cells had DNA breaks at active genes and replication defects. A feedback loop is likely to exist between R-loop and ATM, because ATM can not only be activated by R-loop, but also more R-loop accumulation is observed in ATM knockout mouse.

Considerable effort has been placed into cancer therapy related to p53 and ATM. For example, a retroviral vector containing the wild-type p53 gene was used to mediate transfer of wild-type p53 into cancer patients by direct injection with no clinically significant vector-related toxic effects were noted up to five months after treatment and tumor regression is some of the tested patients.

However, despite the therapeutic efficacy in some patients, others did not respond well in the p53 associated therapy. There remains an urgent need to identify a new target in the ATM-p53 pathway.

SUMMARY OF INVENTION

It is therefore an object of the disclosure to provide solutions to the aforementioned deficiencies in the art. To this end, the present disclosure relates generally to methods of inhibiting proliferation of a cell proliferation, inhibiting $m^3C$ formation in a cell, modulating R-Loop level in a cell, inhibiting activity of Mettl8 in a cell, or activating ATM and p53 in a cell, wherein the method comprising contacting the cell with a Mettl8 inhibitor. In one embodiment, the Mettl8 inhibitor comprises one or more of a CRISPR-Cas system directed to a Mettl8 gene, an shRNA, an RNAi, a miRNA, and cisplatin. In another embodiment, the CRISPR-Cas system comprises at least one guide RNA ("gRNA") that hybridizes to the Mettl8 gene and a Cas nuclease. In one embodiment, the cell is a cancer cell. In another embodiment, the cell is a mammalian cell.

In another aspect, the disclosure is related to a composition comprising a cell, wherein the cell has a reduced expression of Mettl8 compared to control. In another embodiment, the composition further comprises a Mettl8 inhibitor, wherein the Mettl8 inhibitor comprises one or more of a chemical, an antibody, a nucleotide sequence, and an enzyme. In another embodiment, the Mettl8 inhibitor comprises one or more of a CRISPR-Cas system directed to a Mettl8 gene, an shRNA, an RNAi, a miRNA, and cisplatin.

In another aspect, the disclosure provides a method of rendering a tumor cell sensitive to a cancer therapy, the method comprising contacting the tumor cell with a Mettl8 inhibitor. In one embodiment, the cancer therapy comprises cisplatin.

BRIEF DESCRIPTION OF THE DRAWINGS

FIGS. 6A-6D show modulation of $m^3C$ level on mRNA through inhibiting Mettl8 in both human and mouse tissues by CRISPR. FIG. 6A shows Mettl8 binds directly with $^3$H-SAM, but mutation of Mettl8 SAM binding domain abolished its binding activity to $^3$H-SAM. FIG. 6B shows chromatography for $m^3C$ and its quantification in mouse liver tissues with different genetic ablations (right panel) and the quantification of $m^3C$ in total cytidine (left panel). FIG. 6C shows LC-MS/MS chromatography and quantification of $m^3C$ levels in one pair of HCT116 (right panel) and the quantification result (left panel). FIG. 6D shows LC-MS/MS chromatography and quantification of $m^3C$ levels in HeLa S3 cell with Mettl8 wildtype, knockout, and knockout cells rescued by introducing Mettl8 WT or SAM mutant cDNA.

FIG. 7A shows human Mettl8 protein domain structures. FIG. 7N shows even with an efficient viral infect, the level of SAM mutant protein could be barely detected, but phosphorylations on p53, KAP1, Chk2 were enhanced with overexpressed SAM mutant protein. FIG. 7O shows downregulation of Mettle8 by knockdown enhanced ATM phosphorylation at Ser1981. FIG. 7R shows pre-treatment with ATM inhibitor either reverted or eliminated the hyperactivation of ATM, KAP1, Chk2, p53 by irradiation.

FIGS. 8A-8F show modulation of R-Loop level through inhibiting Mettl8 expression. FIG. 8A shows multiple protein bands detected on Flag peptide elution from Flag-Mettl8 immunoprecipitation but not on empty vector controls. FIG. 8B list proteins according to peptide number with 95% confidence in LC-MS analysis. FIG. 8C shows immunoprecipitation with Flag-Mettl8 from HCT116 stable cell. FIG. 8D shows the protein level of TOP1 was reduced in Mettl8 knockout cells. FIG. 8E shows Mettl8 knockout HCT116 cells with stronger R loop staining compared to wild type cells. FIG. 8F shows TOP1 inhibitor camptothecin treatment caused hyperactivation of ATM in Mettl8 knockout cells.

FIGS. 9A-9D show modulation of tumor cells growth by inhibition of Mettl8 expression. FIG. 9A shows HCT116 stable cells examined in cell cycle analysis. FIG. 9B shows HCT116 stable cells examined in soft agar colony assay. FIG. 9C shows a cell growth assay in which knockdown of Mettl8 in HCT116 cells significantly reduced the colony formation. FIG. 9D shows a xenograph assay in which Mettl8 knockout HCT116 cells showed lower tumor growth potential.

FIG. 10A shows results of a cisplatin sensitivity MTS assay. FIG. 10B shows results of a cisplatin sensitivity colony assay.

FIGS. 11A-11F show modulation of the overall survival rate in p53 null or mutant patients through inhibiting Mettl8. FIG. 11A shows in those patients with low p53 expression, Mettl8 low level group (upper panel) showed a better survival rate compared to group with high level of Mettl8 (lower panel). FIG. 11B shows p53 level alone in this cohort of patients makes little difference in terms of overall survival probability. FIG. 11C shows in p53 low or deteriorate mutation cohort, Mettl8-low group showed better survival rate than Mettl8-high group. FIG. 11D shows TP53 or Mettl8 level alone is not the defining marker for better survival rate. FIG. 11E shows survival curve of different genotypes of mice. FIG. 11F shows genes with differential expression levels in MEF from different genetic backgrounds plotted in heat-map.

DETAILED DESCRIPTION

Figure 1:
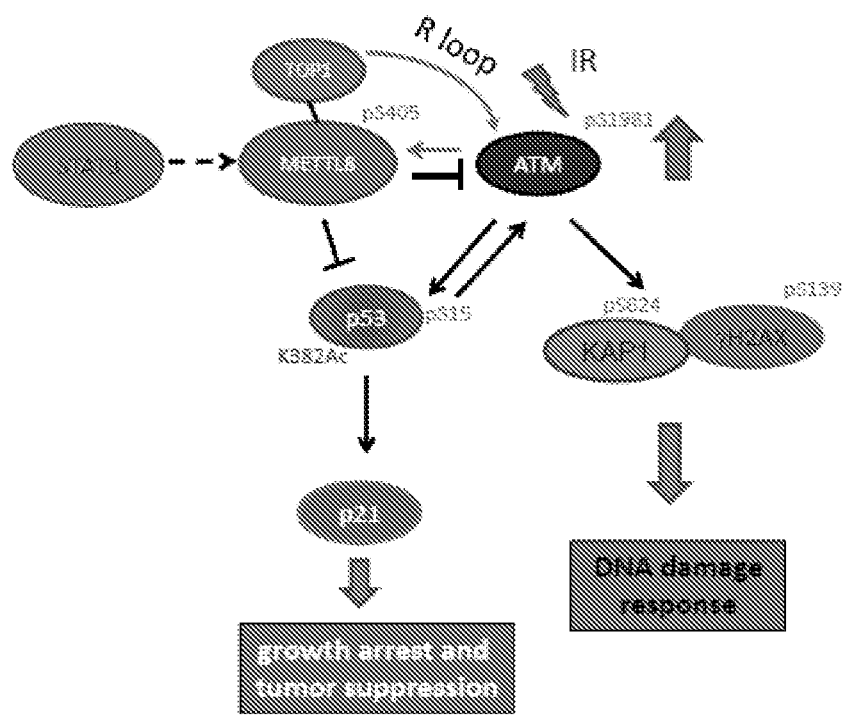
FIG. 1 shows the model of STAT3-Mettl8-ATM-p53 in DNA damage response.

It is to be understood that this invention is not limited to the particular methodology, protocols, cell lines, animal species or genera, compounds, polymers, and reagents described, as such may vary. It is also to be understood that the terminology used herein is for the purpose of describing particular embodiments only and is not intended to limit the scope of the present invention, which will be limited only by the appended claims.

As used herein, unless otherwise stated, the singular forms "a," "an," and "the" include plural reference. Thus, for example, a reference to "a compound" includes a plurality of compounds, and a reference to "a molecule" is a reference to one or more molecules.

All numerical designations, e.g., pH, temperature, time, concentration, amounts, and molecular weight, including ranges, are approximations which are varied (+) or (−) by 10%, 1%, or 0.1%, as appropriate. It is to be understood, although not always explicitly stated, that all numerical designations may be preceded by the term "about." It is also to be understood, although not always explicitly stated, that the reagents described herein are merely exemplary and that equivalents of such are known in the art.

The term "comprising" or "comprises" is intended to mean that the compositions and methods include the recited elements, but do not exclude others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than a trace amount of other ingredients and substantial method steps recited. Embodiments defined by each of these transition terms are within the scope of this invention.

The use of the term "or" in the claims is used to mean "and/or" unless explicitly indicated to refer to alternatives only, or the alternatives are mutually exclusive, although the disclosure supports a definition that refers to only alternatives and "and/or."

As used herein, the term "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The term "nuclease" is used to generally refer to any enzyme that hydrolyzes nucleic acid sequences.

The terms "polynucleotide," "nucleotide," "nucleotide sequence," "nucleic acid," and "oligonucleotide" are used interchangeably. These terms refer to a polymeric form of nucleotides of any length, either deoxyribonucleotides or ribonucleotides, or analogs. Examples of polynucleotides include, but are not limited to, coding or non-coding regions of a gene or gene fragment, exons, intrans, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. One or more nucleotides within a polynucleotide sequence can further be modified. The sequence of nucleotides may be interrupted by non-nucleotide components. A polynucleotide may also be modified after polymerization, such as by conjugation with a labeling agent.

The terms "dosage" or "dosage regiment" is defined herein, as the amount needed for effectiveness of each of the various disease states. Dosage regimens may be adjusted to provide the optimum desired response (e.g., a therapeutic or prophylactic response). For example, a single dosage may be administered or several divided doses may be administered over time or the dose may be proportionally reduced or increased as indicated by the exigencies of the therapeutic situation. Dosage unit form refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals. In some embodiments, the dosage of a particular compound is provided as absolute weight. In some embodiments, the dosage of a particular compound is provided as mass ratio wherein the mass ratio is the fraction of a particular compound out of the total composition. In some embodiments, the dosage is provided as mg compound per kg total bodyweight of the subject to whom the composition is provided, and this dosage format is hereinafter designated mg/kg. In some embodiments, the dosage is provided in hourly, daily, weekly, or monthly dosage regimens.

The terms "patient," "subject," "individual," and the like are used interchangeably herein and refer to any animal, or cells thereof, whether in vitro or in situ, amenable to the methods described herein. In a preferred embodiment, the patient, subject, or individual is mammal. In some embodiments, the mammal is a mouse, a rat, a guinea pig, a non-human primate, a dog, a cat, or a domesticated animal (e.g., horse, cow, pig, goat, sheep). In another embodiment, the patient, subject, or individual is a human.

The term "cancer" is used herein to refer to conditions in which abnormal cells divide without control and can invade nearby tissues. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue, such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord. In some embodiments, the cancer is one or more of pancreatic cancer, renal cancer, small cell lung cancer, brain cancer, neural cancer, bone cancer, lymphoma, myeloma, colon cancer, uterine cancer, breast cancer, leukemia, liver cancer, prostate cancer, skin cancer, and melanoma. In some embodiment the cancer is liver cancer. In some embodiments, the liver cancer is one or more of hepatocellular carcinoma, bile duct cancer, angiosarcoma, hemangiosarcoma, hepatoblastoma, hemangioma, hepatic adenoma, and focal nodular hyperplasia.

The term "treating" or "treatment" covers the treatment of a cancer described herein, in a subject, such as a human, and includes: (i) inhibiting a cancer, i.e., arresting its development; (ii) relieving a cancer or disorder, i.e., causing regression of the cancer; (iii) slowing progression of the cancer; and/or (iv) inhibiting, relieving, or slowing progression of one or more symptoms of the cancer. For example, treatment of a cancer includes, but is not limited to, elimination of the cancer or the condition caused by the cancer, remission of the tumor, inhibition of the cancer, reduction or elimination of at least one symptom of the tumor.

The term "antibody" is used herein to refer to immunoglobulins conventionally used in the art to recognize and bind specific antigens, and can be conjugated with small molecules for targeted delivery to specific cells and tissues as described in Tsuchikama et al., *Protein Cell* 9:33-46

(2018). A person having ordinary skill in the art will know how to conjugate small molecule drugs to antibodies.

The term "administering" or "administration" of an agent to a subject includes any route of introducing or delivering to a subject a compound to perform its intended function. A route of administration is the path by which a drug, fluid, poison, or other substance is taken into the body. Routes of administration are generally classified by the location at which the substance is applied. Administration can be carried out by any suitable route, including parenterally, orally, intraperitoneally, intravenously, intraarterially, transdermally, sublingually, intramuscularly, rectally, transbuccally, intranasally, liposomally, via minicells, via antibody conjugation, via cell targeting peptides, via inhalation, vaginally, intraocularly, via local delivery by catheter or stent, subcutaneously, intraadiposally, intraarticularly, or intrathecally.

The phrase "concurrently administering" refers to administration of at least two agents to a patient over a period of time. Concurrent administration includes, without limitation, separate, sequential, and simultaneous administration.

The term "separate" administration refers to an administration of at least two active ingredients at the same time or substantially the same time by different routes.

The term "sequential" administration refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients.

The term "simultaneous" administration refers to the administration of at least two ingredients by the same route and at the same time or at substantially the same time.

The term "therapeutic" as used herein means a treatment and/or prophylaxis. A therapeutic effect is obtained by suppression, remission, or eradication of a disease state.

The term "therapeutically effective amount" or "effective amount" refers to an amount of the agent that, when administered, is sufficient to cause the desired effect. For example, an effective amount of a composition may be an amount sufficient to treat, control, alleviate, or improve the conditions related to parasitic diseases. The therapeutically effective amount of the agent may vary depending on the pathogen being treated and its severity as well as the age, weight, etc., of the patient to be treated. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder.

The term "analog" refers to a compound in which one or more individual atoms or functional groups have been replaced, either with a different atom or a different functional, generally giving rise to a compound with similar properties. In some aspect, the analog refers to a structure that is similar to another but differs in one or two components.

The term "derivative" refers to a compound that is formed from a similar, beginning compound by attaching another molecule or atom to the beginning compound. Further, derivatives, according to the invention, encompass one or more compounds formed from a precursor compound through addition of one or more atoms or molecules or through combining two or more precursor compounds.

The term "pharmaceutically acceptable carrier" refers to a carrier that is conventionally used in the art to facilitate the storage, administration, and/or the healing effect of a biologically active agent. Pharmaceutical carriers can also provide timed delayed release of the drug and targeted release of the drug to specific tissues. Many types of delivery systems for targeted release of drugs are available and known to those of ordinary skill in the art, including controlled-release biodegradable polymers, polymeric microsphere carriers and liposomes, as well as the co-administration of cytoprotective agents with antineoplastics as described in Chonn and Cullis, Curr *Opinion in Biotechnology*, 6: 698-708 (1995); Kemp et al., *J. Clin. Oncol*, 14: 2101-2112 (1996); Kumanohoso et al., *Cancer Chemother. Pharmacol*, 40: 112-116 (1997); Schiller et al., *J. Clin. Oncol*, 14: 1913-1921 (1996); and Sipos et al., *Cancer Chemother. Pharmacol*, 39: 383-389 (1997). The liposome can be further coated with polyethene glycol (PEG) to prolong their circulation time. Furthermore, targeted delivery of the drugs can be achieved by using minicells as described in WO 2005/079854. The minicells comprises a first arm that carries specificity for a bacterially derived minicell surface structure and a second arm that carries specificity for a mammalian cell surface receptor, to target drug-loaded minicells to specific mammalian cells and to cause endocytosis of the minicells by the mammalian cells. Accordingly, in some embodiments, the pharmaceutical composition is administered in a targeted release system.

The term "Mettl8" refers to Methyltransferase-like protein 8, or the nucleic acid (cDNA or genomic DNA) encoding such a protein. Non-limiting examples of "Mettl8" protein include the human Mettl8 (GenBank: AAH25250.1) and mouse Mettl8 (GenBank: AAH57960.1).

The term "p53" refers to the nuclear protein that plays an essential role in the regulation of cell cycle, specifically in the transition from G0 to G1, or the nucleic acid (cDNA or genomic DNA) encoding such a nuclear protein. p53 is a DNA-binding protein containing DNA-binding, oligomerization and transcription activation domains. It is postulated to bind as a tetramer to a p53-binding site and activate expression of downstream genes that inhibit growth and/or invasion, and thus function as a tumor suppressor. Mutants of p53 that frequently occur in a number of different human cancers fail to bind the consensus DNA binding site, and hence cause the loss of tumor suppressor activity. Non-limiting exemplary "p53" proteins include the human p53, such as that listed by GenBank protein ID: NP-000537, and its structural and functional polymorphisms. The decoy p53 fragments can indirectly influence the function of p53. For example, it has been shown that mdm2 can promote the destabilization of p53 and that this function depends on interaction of both proteins. p53 decoy fragments can bind to mdm2 which can then make available the transcriptionally active p53. This could enhance the pro-apoptotic function of p53 in cancer treatment or its protective effect in normal cells from oxidative stress or radiation induced DNA damage (Kubbutal and Vousden, *Molecular Medicine Today*, June 1998, pgs. 250-256).

A term "therapeutic agent" as used herein refers to an agent which can mitigate, cure, treat or prevent a disease or condition. It is particularly desirable that the therapeutic agent be capable of exerting it effect locally (i.e., at or near the site of the disease or condition). Non-limiting examples of therapeutic agents include antibodies, antibiotics, anti-restenotics, anti-proliferative agents, anti-neoplastic agents, chemotherapeutic agents, anti-cancer agents, anti-inflammatory agents, immunosuppressive agents, anti-apoptotic and anti-tissue damage agents.

The terms "ATM" or "ATM kinase" refers to a polypeptide that phosphorylates target proteins that have an ATM kinase substrate recognition consensus sequence motif, or the nucleic acid (cDNA or genomic DNA) encoding such an ATM kinase. Such ATM kinases include human ATM kinase described in U.S. Pat. Nos. 5,756,288, 5,728,807, and 5,777,093, including both wild-type and naturally occurring mutant ATM kinases. Naturally occurring mutant ATM kinases are either truncated or are unstable proteins. The term as used herein also encompasses non-human ATM kinases, which can be used in the various assays and methods of the invention.

The term "sensitive," as used herein, refers to a condition when a disease, a cell, or an organ responds to a treatment. The sensitivity can be either intrinsic or acquired. In one embodiment, administration of an agent renders a cell sensitive to the therapeutic efficacy of another agent. For example, as in this invention, inhibition of Mettl8 activity renders a tumor cell more sensitive to various cancer therapies, e.g., cisplatin. On the contrary, the term "drug resistance" refers to a condition when a disease, a cell, or an organ does not respond to or less responsive to a treatment.

As used herein, the term "recombinant vector" refers to a vector transferring a polynucleotide sequence of interest to a target cell. Such a vector is capable of self-replication or incorporation into a chromosome in a host cell (e.g., a prokaryotic cell, yeast, an animal cell, a plant cell, an insect cell, an individual animal, and an individual plant, etc.), and contains a promoter at a site suitable for transcription of a polynucleotide of the present invention. The recombinant vector may comprise a structural gene and a promoter for regulating expression thereof, and in addition, various regulatory elements in a state that allows them to operate within host cells. It is well known in the art that a type of recombinant vector of a living organism such as an animal and a species of a regulatory element used may vary depending on the type of host cell used. The recombinant vector, as used herein, encompasses both viral and non-viral vectors. Non-limiting examples of viral vectors include a retroviral vector, a lentiviral vector, a murine leukemia viral ("MLV") vector, an Epstein-Barr viral ("EBV") vector, an adenoviral vector, a herpes viral ("HSV") vector (e.g., HSV-1 and HSV-2), and an adeno-associated viral vector.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "gRNA" or "guide RNA" refers to a RNA containing a sequence that is complementary or substantially complementary to a region of a target DNA sequence. A guide RNA may contain nucleotide sequences other than the region complementary or substantially complementary to a region of a target DNA sequence. A guide RNA may be a crRNA or a derivative thereof, e.g., a crRNA:tracrRNA chimera. Non limiting examples of guide sequences can be found at SEQ ID Nos: 9-14 of the present disclosure.

As used herein, the term "CRISPR-Cas system" or "CRISPR" refers to an enzyme system including a guide RNA sequence that contains a nucleotide sequence complementary or substantially complementary to a region of a target polynucleotide, and a protein with nuclease activity. CRISPR-Cas systems include Type I CRISPR-Cas system, Type II CRISPR-Cas system, Type III CRISPR-Cas system, and derivatives thereof. CRISPR-Cas systems include engineered and/or programmed nuclease systems derived from naturally accruing CRISPR-Cas systems. CRISPR-Cas systems may contain engineered and/or mutated Cas proteins. CRISPR-Cas systems may contain engineered and/or programmed guide RNA.

The term "Mettl8 inhibitor" as used herein refers to a molecule having the ability to inhibit a biological function of Mettl8. Accordingly, the term "inhibitor" is defined in the context of the biological role of Mettl8. While preferred inhibitors herein specifically interact with (e.g., bind to) Mettl8, molecules that inhibit a Mettl8 biological activity by interacting with other members of the Mettl8 signal transduction pathway are also specifically included within this definition. Non-limiting examples of Mettl8 inhibitor include peptides, shRNAs, CRISPR systems, non-peptide small molecules, antibodies, antibody fragments, antisense molecules, and oligonucleotide decoys.

The term "cisplatin" refers to a chemical comprising a formula of $Pt(NH_3)_2Cl$ and its derivatives and analogs. Non-limiting examples of cisplatin include carboplatin, ormaplatin, oxaplatin, 2-aminomethylpyrrolidine (1,1-cyclobutane dicarboxylato) platinum, lobaplatin, 1-cyclobutane-dicarboxylato(2−)-(2-methyl-1,4-butanediamine-N,N') platinum, zeniplatin, enloplatin, 254-S nedaplatin and JM-216 (bis-acetato-amine-dichloro-cyclohexylamine-platinum(IV)).

The term "interstrand crosslinking agent" refers to an agent that have two independently reactive groups within the same molecule, each of which is able to bind with a nucleotide residue of DNA. These agents are separated based upon their source of origin and labeled either as exogenous or endogenous. Non-limiting examples of interstrand crosslinking agents include nitrogen mustards, cisplatin, chloroethyl nitroso urea, psoralens, mitomycin C ("MMC"), nitrous acid, and bifunctional aldehydes.

STAT3 and p53

The Janus kinases (JAKs) and signal transducer and activator of transcription (STAT) proteins. The STAT3 oncogene is among the most promising new targets for cancer therapy. In addition to interleukin-6 (IL-6) and its family members, multiple pathways, including G-protein-coupled receptors (GPCRs), Toll-like receptors (TLRs) and microRNAs were recently identified to regulate JAK-STAT signalling in cancer. The JAK-STAT3 pathway is aberrantly hyperactivated in many types of cancer, and such hyperactivation is generally associated with a poor clinical prognosis. In the tumor microenvironment, JAK-STAT3 signaling acts to drive the proliferation, survival, invasiveness, and metastasis of tumour cells, while strongly suppressing the antitumour immune response.

p53 is one of the most studied tumor suppressors. An activated p53 can execute its tumor suppressor function by inducing cell growth arrest, apoptosis, autophagy, alterations of metabolism, ferroptosis and necrosis through transcription-dependent and/or transcription-independent mechanisms.

While p53 is a tumor suppressor and STAT3 acts as an oncogene, the functional interactions between the two proteins and their respectively involved pathways remain unclear. Surprisingly, in this disclosure, inventors unveil a functional link between the two pathways via the methyltransferase like protein 8 (Mettl8)-ATM loop. As shown in FIG. 1, Mettl8 as a target of STAT3 serves an important connection between the two pathways. Loss of function mutation or gene knockout of Mettl8 can lead to hyper activation of ATM and affect KAP1, p53 and H2AX activities, which together result in orchestrated DNA repair response and cell cycle checkpoint maintenance. Mettl8 deficiency can prevent the tumorigenesis originating from p53 deficiency, supporting a role of Mettl8 in regulation of p53 tumor suppressor function. Even as a substrate of ATM, Mettl8 can in turn suppress the activation of ATM and its downstream mediators in DNA damage response.

Figure 7A:
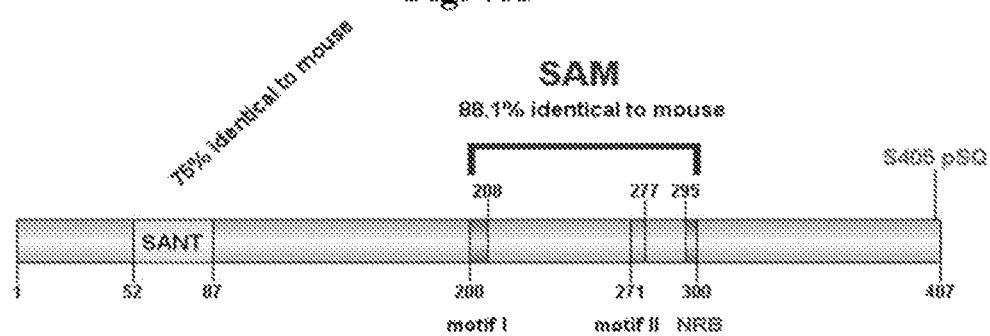
FIGS. 7A-7R show activation of ATM-p53 pathway by inhibiting Mettl8 expression.

Sequence analysis of human Mettl8 protein reveals that it is featured with an N-terminal SANT domain (Swi3, Ada2, N-CoR and TFIIIB) domain which recruits p300 and binds histone tails, a middle SAM binding domain for methyltransferase activity, and a C-terminal NRB (nuclear receptor binding) motif as shown in FIG. 7A. The SAM binding domain includes seven-stranded beta sheet with three helices on each side. The primary sequence may have variance but they define the Rossmann fold, hallmark structure of class I methyltransferase. The N-terminal region of the core fold contains highly conserved glycine-rich sequence E/DXGXGXG (often referred to as motif I) between β1 and αA, which interacts with the amino acid portion of SAM. Splicing isoforms of Mettl8 in mouse were identified in tension induction assay and played a role in lipogenesis possibly via SANT dependent p300 recruitment which in turn showed histone acetylation activity.

A unique pS/TQ motif sits at the very C-terminus of human Mettl8 protein. Surprisingly, inventors discovered that the pS/TQ motif is a substrate of ATM or its related ATR (ATM- and RAD3-related) and DNAPKcs (DNA-dependent protein kinase catalytic subunit) kinases. S/TQ is a minimal essential requirement for all three kinases. Hydrophobic amino acids and negatively charged amino acids immediately N-terminal to serine, or threonine are positive determinants. Positively charged amino acids in the region are negative determinants for substrate phosphorylation.

In addition, inventors found that abolishment of Mettl8 function causes resistance to irradiation and induces a cell growth checkpoint via p53 activation. Genetically, Mettl8 knockout in mice dramatically suppresses the oncogenesis caused by p53 deficiency. Consistently, Mettl8 is highly expressed in human colorectal cancers significantly associated with enhanced fatality in patients that harbor lower levels of p53. The results demonstrate that the STAT3-Mettl8 pathway mediates oncogenesis by inactivating the ATM-p53 pathway. Also, inventors discovered that Mettl8 is downregulated at transcriptional level by treatment with interstrand crosslinking agents like cisplatin and mitomycin C. Mettl8 knockout cells show higher sensitivity to cisplatin treatment, but more resistant to gamma irradiation. Moreover, inhibition of Mettl8 can modulate R-Loop level in a cell.

Therefore, the disclosure provides methods of inhibiting proliferation of a cell, inhibiting $m^3C$ formation in a cell, modulating R-Loop level in a cell, inhibiting activity of Mettl8 in a cell, or activating ATM and p53 in a cell, the method comprising contacting the cell with a Mettl8 inhibitor. In one embodiment, the Mettl8 inhibitor is a chemical, an antibody, a nucleotide sequence, or an enzyme.

The Mettl8 activity can be inhibited a genetic or non-genetic means. The Mettl8 inhibitor, in one embodiment, comprises one or more of a CRISPR system directed to a Mettl8 gene, a Mettl8 variant, an shRNA (short hairpin RNA), an siRNA, an RNAi, a miRNA, a STAT3 inhibitor, and an interstrand crosslinking agent. In one embodiment, the CRISPR-Cas system, the shRNA, the RNAi, and/or miRNA are encoded by one or more recombinant vectors.

The recombinant vector comprises at least one promoter which controls expression of at least one segment corresponding to a shRNA, to complementary short interfering RNA (siRNA) or miRNA.

The shRNA, siRNA, RNAi, or miRNA of the present invention can suppress or silence a gene of interest (e.g., Mettl8 and STAT3). The interfering RNA can be provided in several forms. For example, an interfering RNA can be provided as one or more isolated small-interfering RNA (siRNA) duplexes, longer double-stranded RNA (dsRNA), or as siRNA or dsRNA transcribed from a transcriptional cassette in a DNA plasmid. The interfering RNA may also be chemically synthesized. The interfering RNA can be administered alone or co-administered (i.e., concurrently or consecutively) with conventional agents used to treat a disease associated with Mettl8 activity. In one embodiment, the shRNA comprises a polynucleotide sequence that comprises SEQ ID No 1, SEQ ID No. 2, SEQ ID No. 3, SEQ ID No. 4, SEQ ID No. 5, SEQ ID No. 6, SEQ ID No. 7, or SEQ ID No. 8. The particular sequences of the above SEQ ID Nos are listed in Table 1.

TABLE 1 shRNA sequences

| Name | shRNA sequence | SEQ ID NO: |
|---|---|---|
| Scramble shRNA | GATTTAGACTAGGTAGAGA | SEQ ID No: 1 |
| M8 shRNA1 | GTTGAGGGAATTTCCTGAAAT | SEQ ID No: 2 |
| M8 shRNA2 | GCGAGAGAATCATCATGGGAT | SEQ ID No: 3 |
| M8 shRNA3 | GTGCTACAAATCGTTTCTCAA | SEQ ID No: 4 |
| M8 shRNA4 | GATCGCCGCTTACAAGTTAAT | SEQ ID No: 5 |
| M8 shRNA5 | CTCCTTGTGTCTCCGTTTAAA | SEQ ID No: 6 |
| STAT3 shRNA | TTTGTGCTTAGGATGGCCC | SEQ ID No: 7 |
| Full sequence of STAT3 shRNA | GATCCCCGGGCCATCCTAAGC ACAAATTCAAGAGATTTGTGC TTAGGATGGCCCTTTTTA | SEQ ID No: 8 |

The phrase "inhibiting expression of a target gene" refers to the ability of an shRNA, an siRNA, an RNAi, or an miRNA molecule of the present invention to silence, reduce, or inhibit expression of a target gene (e.g., Mettl8 and STAT3). For example, to examine the extent of gene silencing, a test sample (e.g., a biological sample from an organism of interest expressing the target gene or a sample of cells in culture expressing the target gene) is contacted with an siRNA or an shRNA that silences, reduces, or inhibits expression of the target gene. Expression of the target gene in the test sample is compared to expression of the target gene in a control sample that is not contacted with the siRNA. Control samples are assigned a value of 100%. Silencing, inhibition, or reduction of expression of a target gene is achieved when the value of test the test sample relative to the control sample is about 95%, 90%, 85%, 80%, 75%, 70%, 65%, 60%, 55%, 50%, 45%, 40%, 35%, 30%, 25%, 20%, or 10%. Suitable assays include, e.g., examination of protein or mRNA levels using techniques known to those of skill in the art such as dot blots, Northern blots, in situ hybridization, ELISA, immunoprecipitation, enzyme function, as well as phenotypic assays known to those of skill in the art. Thus, in one embodiment, the shRNA, siRNA, RNAi, or miRNA of the present invention can suppress or silence a gene of interest by more than 95%, 90%, 85%, 80%, 75%, 70%, 65%, 60%, 55%, 50%, 45%, 40%, 35%, 30%, 25%, 20%, 10%, 5%, or 1%.

The present disclosure takes advantage of a site-specific nuclease, which comprises CRISPR gene-editing system, omega, zinc finger, or TALE. The CRISPR gene-editing system use a gene-editing enzyme with one or multiple unique single guide (sg) RNA sequences that target mutant allele(s) specifically or that target a gene (e.g., Mettl8 gene) for destruction. Deletion of the gene, in one embodiment, results in the knockout of the gene in a cell, a mammal, or a subject. In one embodiment, the CRISPR system leads to the knockout of the Mettl8 gene in a cell. In another embodiment, the CRISPR system leads to the knockout of the Mettl8 gene in a mammal (e.g., mouse or human). The CRISPR system comprises a polynucleotide sequence comprising at least one guide RNA ("gRNA") that hybridizes to the Mettl8 gene. In one embodiment, the gRNA comprises a polynucleotide sequence of SEQ ID No 9, SEQ ID No 10, SEQ ID No 11, SEQ ID No 12, SEQ ID No 13, or SEQ ID No 14. In some embodiments, the CRISPR system comprises a polynucleotide sequence encoding a Cas family enzyme. The polynucleotide comprising a gRNA and the polynucleotide encoding the Cas family enzyme are encoded by one or more recombinant vectors. In one embodiment, the two polynucleotides are encoded by two different recombinant vectors.

The sequence-specific endonuclease (e.g., Cas) of the methods and compositions described here can be engineered, chimeric, or isolated from an organism. Endonucleases can be engineered to recognize a specific DNA sequence, by, e.g., mutagenesis. Seligman et al. (2002) *Mutations altering the cleavage specificity of a homing endonuclease, Nucleic Acids Research* 30: 3870-3879. Combinatorial assembly is a method where protein subunits form different enzymes can be associated or fused. Arnould et al. (2006) *Engineering of large numbers of highly specific homing endonucleases that induce recombination to novel DNA targets, Journal of Molecular Biology* 355: 443-458. In certain embodiments, these two approaches, mutagenesis and combinatorial assembly, can be combined to produce an engineered endonuclease with desired DNA recognition sequence.

The sequence-specific nuclease can be introduced into the cell in the form of a protein or in the form of a nucleic acid encoding the sequence-specific nuclease, such as an mRNA or a cDNA. Nucleic acids can be delivered as part of a larger construct, such as a plasmid or viral vector, or directly, e.g., by electroporation, lipid vesicles, viral transporters, microinjection, and biolistics. Similarly, the construct containing the one or more transgenes can be delivered by any method appropriate for introducing nucleic acids into a cell. Thus, the recombinant vector that encodes gRNA(s) and/or Cas can be a viral vector or a non-viral vector. Non-limiting examples of viral vectors include a retroviral vector, a lentiviral vector, a murine leukemia viral ("MLV") vector, an Epstein-Barr viral ("EBV") vector, an adenoviral vector, a herpes viral ("HSV") vector (e.g., HSV-1 and HSV-2), and an adeno-associated viral ("AAV") vector.

Single guide RNA(s) used in the methods of the present disclosure can be designed so that they direct binding of the Cas-gRNA complexes to pre-determined cleavage sites in a genome. In one embodiment, the cleavage sites may be chosen so as to release a fragment or sequence that contains a region of autosomal dominant disease-related gene. In further embodiment, the cleavage sites may be chosen so as to release a fragment or sequence that contains a region of Mettl8.

For Cas family enzyme (such as Cas9) to successfully bind to DNA, the target sequence in the genomic DNA should be complementary to the gRNA sequence and must be immediately followed by the correct protospacer adjacent motif or "PAM" sequence.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule, which can form hydrogen bonds (e.g., Watson-Crick base pairing) with a second nucleic acid sequence. Full complementarity is not necessarily required, provided there is sufficient complementarity to cause hybridization and promote formation of a CRIS PR complex. A target sequence may comprise any polynucleotide, such as DNA or RNA polynucleotides. The Cas9 protein can tolerate mismatches distal from the PAM, however, mismatches within the 12 base pairs (bps) of sequence next to the PAM sequence can dramatically decrease the targeting efficiency. The PAM sequence is present in the DNA target sequence but not in the gRNA sequence. Any DNA sequence with the correct target sequence followed by the PAM sequence will be bound by Cas9. The PAM sequence varies by the species of the bacteria from which Cas9 was derived. The most widely used CRISPR system is derived from *S. pyogenes* and the PAM sequence is NGG located on the immediate 3' end of the sgRNA recognition sequence. The PAM sequences of CRISPR systems from exemplary bacterial species include: *Streptococcus pyogenes* (NGG), *Neisseria meningitidis* (NNNNGATT), *Streptococcus thermophilus* (NNAGAA) and *Treponema denticola* (NAAAAC).

The gRNA(s) used in the present disclosure can be between about 5 and 100 nucleotides long, or longer (e.g., 5, 6, 7, 8, 9, 10, 11, 12, 13, 14, 15. 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides in length, or longer). In one embodiment, the gRNA(s) can be between about 15 and about 30 nucleotides in length (e.g., about 15-29, 15-26, 15-25; 16-30, 16-29, 16-26, 16-25; or about 18-30, 18-29, 18-26, or 18-25 nucleotides in length).

To facilitate gRNA design, many computational tools have been developed (See Prykhozhij et al. (PLoS ONE, 10(3): (2015)); Zhu et al. (PLoS ONE, 9(9) (2014)); Xiao et al. (Bioinformatics. January 21 (2014)); Heigwer et al. (Nat Methods, 11(2): 122-123 (2014)). Methods and tools for guide RNA design are discussed by Zhu (Frontiers in Biology, 10 (4) pp 289-296 (2015)), which is incorporated by reference herein. Additionally, there is a publically available software tool that can be used to facilitate the design of gRNA(s) (http://www.genscript.com/gRNA-design-tool.html). In one embodiment, the CRISPR system that targets Mettl8 comprises a gRNA that comprises a polynucleotide sequence of SEQ ID No 9, SEQ ID No 10, SEQ ID No 11, SEQ ID No 12, SEQ ID No 13, or SEQ ID No 14. The sequences of SEQ ID Nos 9-14 are listed in Table 2.

TABLE 2

Guide sequences in gRNAs

| gRNA | Sequence | SEQ ID NO: |
|---|---|---|
| Human Mettl8 gRNA 1 | TAACTTTTTAGGTACTGCTT | SEQ ID No: 9 |
| Human Mettl8 gRNA 2 | CTCAGCTGTGCGAGTCCTTC | SEQ ID No: 10 |
| Human Mettl8 gRNA 3 | GAAGGCGAGAGAATCATCAT | SEQ ID No: 11 |
| Mouse Mettl8 gRNA 1 | AAGTTTTTGAACACAACATG | SEQ ID No: 12 |
| Mouse Mettl8 gRNA 2 | AGTTTTGTCTCGCCAGAACC | SEQ ID No: 13 |
| Mouse Mettl8 gRNA 3 | GGGAAGACAGAGCCGTTTCC | SEQ ID No: 14 |

Surprising, inventors discovered that an interstrand crosslinking agent (e.g., cisplatin and MMC) can inhibit expression of Mettl8 expression. Thus, the Mettl8 inhibitor comprises an interstrand crosslinking agent. In one embodiment, the interstrand crosslinking agent comprises nitrogen mustard, cisplatin, chloroethyl nitroso urea, psoralens, mitomycin C ("MMC"), nitrous acid, bifunctional aldehyde, or combination thereof. In one embodiment, the interstrand crosslinking agent is cisplatin or MMC. In another embodiment, the interstrand crosslinking agent is cisplatin.

Figure 5A:
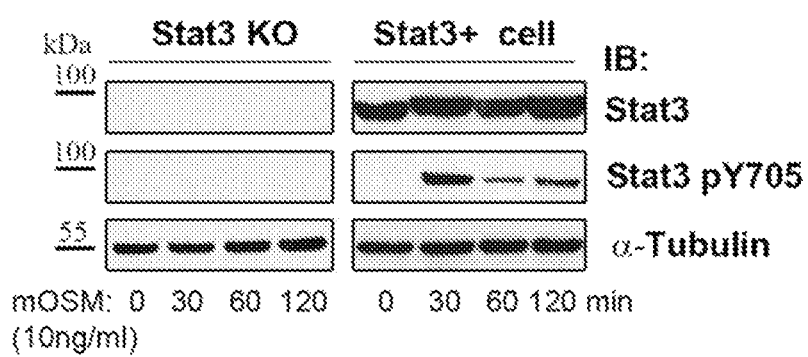
FIG. 5 shows regulation of Mettl8 protein expression by modulating STAT3 activity.
FIG. 5F discloses SEQ ID NOS 29 and 29-33, respectively, in order of appearance.
Figure 5B:
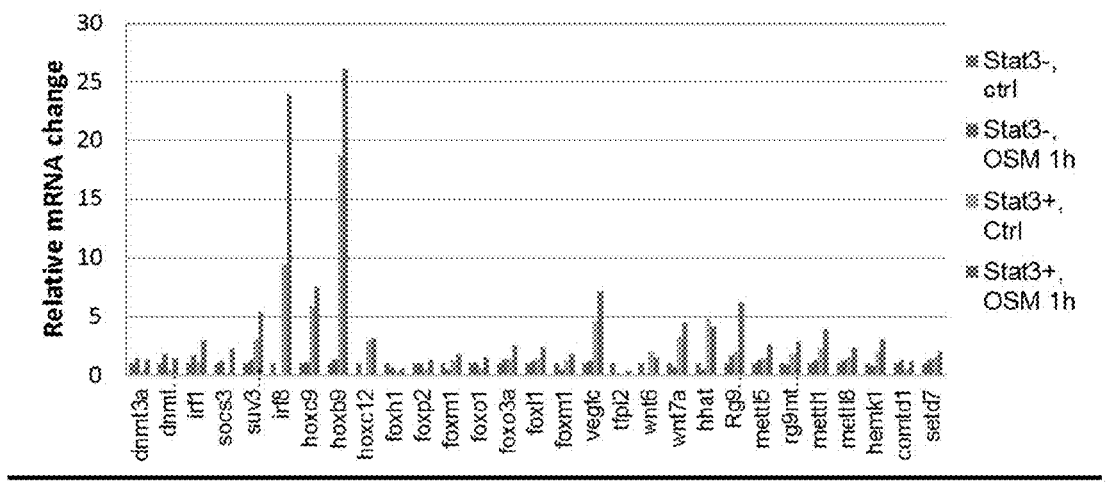
Figure 5C:
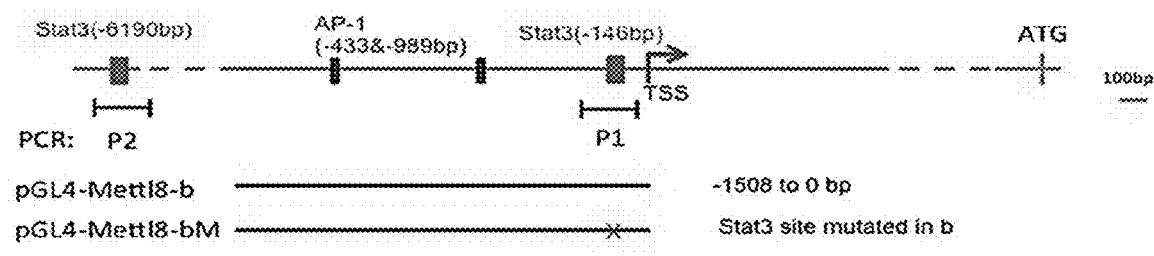
Figure 5D:
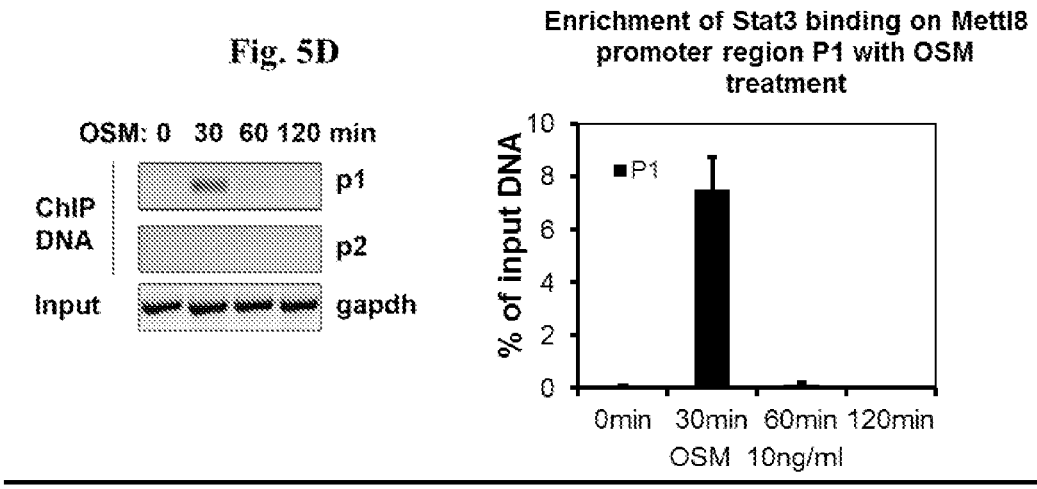
Figure 5E:
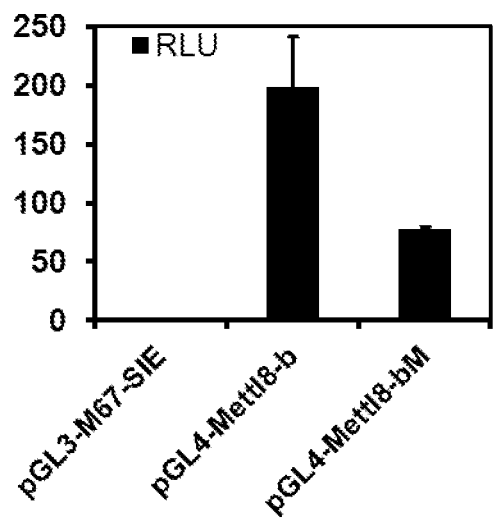
Figure 5F:
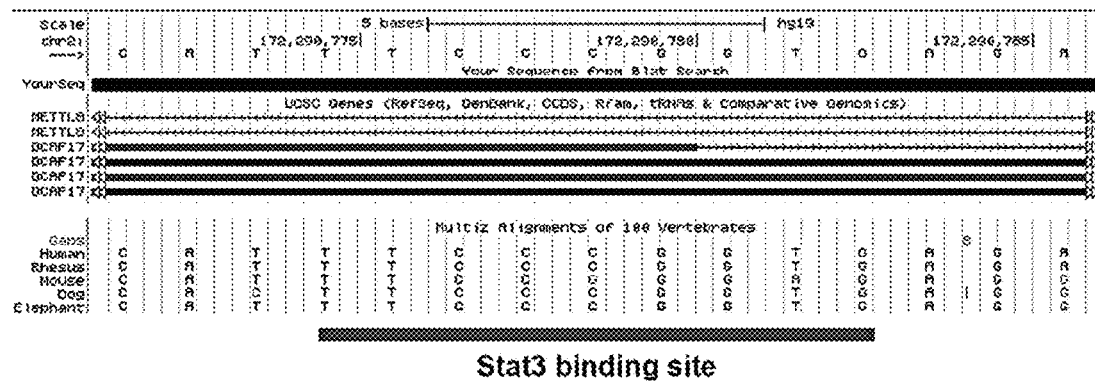
Figure 5G:
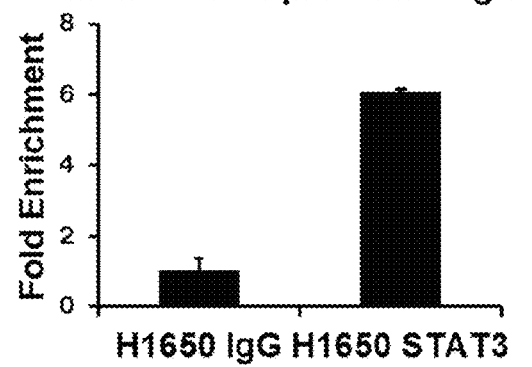
Figure 5H:
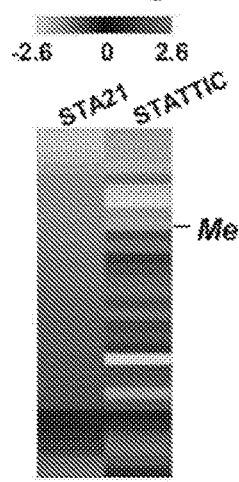
Figure 5I:
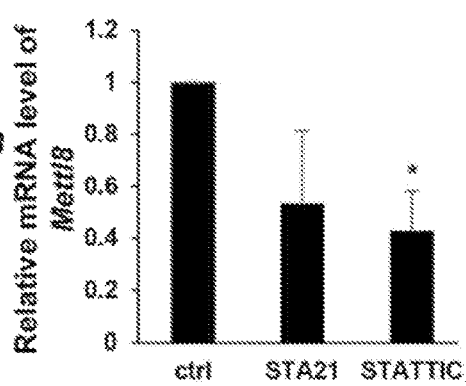

Because STAT3 is a transcriptional factor for Mettle8, inhibition of STAT3 can also suppress Mettle8 expression or activity (FIG. 5I). Thus, in one embodiment, the Mettl8 inhibitor comprises a STAT3 inhibitor. In another embodiment, the STAT3 inhibitor is a small molecule comprising one or more of STAT3 Inhibitor V, 6-Nitrobenzo[b]thiophene 1,1-dioxide (Stattic), (1E,6E)-1,7-Bis(4-hydroxy-3-methoxyphenyl)-1,6-heptadiene-3,5-dione (curcumin), N-(1',2-Dihydroxy-1,2'-binaphthalen-4'-yl)-4-methoxybenzenesulfonamide (C188-9), N-Hexyl-2-(1-naphthalenyl)-5-[[4-(phosphonooxy)phenyl]methyl]-4-oxazolecarboxamide (S3I-M2001), 8-hydroxy-3-methyl-3,4-dihydrotetraphene-1,7,12(2H)-trione (STA-21), 2-Hydroxy-4-[[2-[[(4-methylphenyl)sulfonyl]oxy]acetyl]amino]benzoic acid (S3I-201), Cepharanthine, Cucurbitacin I, *Cucumis sativus* L, Niclosamide, Cryptotanshinone, SD 1008, Stat3 Inhibitor III, WP1066, Nifuroxazide, Stat3 Inhibitor VI, S3I-201, STA-21, Kahweol, STAT3 Inhibitor IX, Cpd188; STAT3 Inhibitor VI, S3I-201; STAT3 Inhibitor VII Ethyl-1-(4-cyano-2,3,5,6-tetrafluorophenyl)-6,7,8-trifluoro-4-oxo-1,4-dihydroquinoline-3-carboxylate; STAT3 Inhibitor VIII, 5,15-DPP, STAT3 Inhibitor X, HJB; STAT3 Inhibitor XII, SPI; STAT3 Inhibitor XI, STX-0119; STAT3 Inhibitor XIV, LLL12; FLLL32; FLLL62 and any derivatives, analogs or any combinations thereof or any vehicle, matrix, nano- or micro-particle comprising the same. In one embodiment, the STAT3 inhibitor comprises one or more of static, STA-21, S31-201, or LLL12.

Figure 6C:
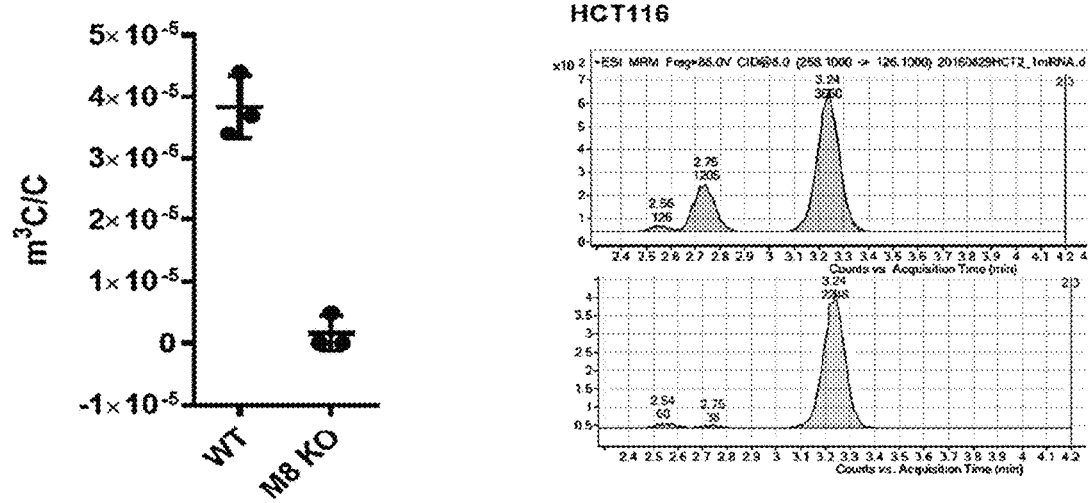

In another embodiment, the Mettl8 inhibitor is a Mettle8 variant protein or a polynucleotide sequence that encodes the Mettl8 variant protein. In one embodiment, the SAM domain in the Mettle8 variant protein is fully or partially deleted. Surprisingly, inventor discovered that expression of the Mettl8 ΔSAM variant in cells can induce ATM/p53 activation and cell growth arrest (FIGS. 9A and 9B). Without being bound by a theory, Mettle8 variant protein may inhibit the Mettle activity through a "competitive inhibition" mechanism, under which the Mettl8 variant competes with the endogenous Mettl8 in a cell, but because the Mettl8 variant lost the ability to bind the SAM donor molecule (FIG. 6A), the variant protein cannot activate the methyl transferring function as the endogenous Mettl8. In one embodiment, the Mettl8 variant is a protein that has a full or partial deletion in the SAM domain or the polynucleotide (e.g., DNA and RNA) that encodes the protein. In one embodiment, the deleted SAM domain sequence is Ile-Leu-Glu-Val-Gly-Cys-Gly-Ala-Gly (SEQ ID No. 16) or its encoding cDNA sequence is atactagaggttggttgtggagctgga (SEQ ID No. 17). In one embodiment, the deleted portion of SAM domain corresponds to aa 200-208 of the wide type human Mettl8 protein. The aforementioned deletion results in a Mettle8 variant with the following sequence:

(SEQ ID NO. 18)
MNMIWRNSISCLRLGKVPHRYQSGYHPVAPLGSRILTDPAKVFEHNMWDHM

QWSKEEEAAARKKVKENSAVRVLLEEQVKYEREASKYWDTFYKIHKNKFFK

DRNWLLREFPEILPVDQKPEEKARESSWDHVKTSATNRFSRMHCPTVPDEK

NHYEKSSGSSEGQSKTESDFSNLDSEKHKKGPMETGLFPGSNATFRNSVFP

ILNTLENSPESFLYCCDFASGAVELVKSHSSYRATQCFAFVHDVCDDGLPY

PFPDGILDVILLVFVLSSIHPDRMQGVVNRLSKLLKPGGMLLFRDYGRYDK

TQLRFKKGHCLSENFYVRGDGTRAYFFTKGEVHSMFCKASLDEKQNLVDRR

LQVNRKKQVKMHRVWIQGKFQKPLHQTQNSSNMVSTLLSQD

In another embodiment, the Mettl8 variant comprises a sequence of SEQ ID No. 18 or a polynucleotide that encodes the sequence of SEQ ID No. 18. In one embodiment, the polynucleotide that encodes the sequence of SEQ ID No. 18 comprises the following sequence:

(SEQ ID No. 19)
atgaatatgatttggagaaattccatttcttgtctaaggctaggaaaggtg ccacacagataccaaagtggttaccacccagtggcccctctgggatcaagg attttaactgacccagccaaagttttttgaacacaacatgtgggatcacatg cagtggtctaaggaagaagaagcagcagccagaaaaaaagtaaaagaaaac tcagctgtgcgagtccttctggaagagcaagttaagtatgagagagaagct agtaaatactgggacacattttacaagattcataagaataagttttcaag gatcgtaattggctgttgagggaatttcctgaaattcttccagttgatcaa aaacctgaagagaaggcgagagaatcatcatgggatcatgtaaaaactagt gctacaaatcgtttctcaagaatgcactgtcctactgtgcctgatgaaaaa aatcattatgagaaagttctggttcttcagaaggtcaaagcaaaacagaa tctgattttccaacctagactctgaaaaacacaaaaaaggacctatggag actggattgtttcctggtagcaatgccacttcaggaatagtgtgtttca attttgaacactttggagaactctccggagtcctttctgtattgttgtgat tttgcttctggagctgtggagctcgtaaagtcacactcgtcctacagagca acccagtgttttgcctttgttcatgatgtatgtgatgatggcttaccttac ccttttccagatgggatcctggatgtcattctccttgtctttgtgctctct tctattcatcctgacaggatgcaaggtgttgtaaaccgactgtccaagtta

```
ctgaaacctgggggaatgctgttatttcgagactatggaagatatgataag actcagcttcgttttaaaaagggacattgtttatctgaaaatttttatgtt cgaggagatggtaccagagcatatttctttacaaaaggggaagtccacagt atgttctgcaaagccagtttagatgaaaagcaaaatctggttgatcgccgc ttacaagttaataggaaaaaacaagtgaaaatgcaccgagtgtggattcaa ggcaaattccagaaaccattgcaccagactcagaatagctccaatatggta tctacactcctttcacaagactga.
``` m3C Formation

Chemical RNA modifications are central features of epitranscriptomics, highlighted by the discovery of modified ribonucleosides in mRNA and exemplified by the critical roles of RNA modifications in normal physiology and disease. Despite a resurgent interest in these modifications, the biochemistry of 3-methylcytidine ($m^3C$) formation in mammalian RNAs is still poorly understood. Unexpectedly, inventors discovered and characterized three distinct $m^3C$-contributing enzymes in mice and humans. Methyltransferase-like (METTL) 2 and 6 contribute to m3C formation in specific tRNAs and that METTL8 only contributes to $m^3C$ formation in mRNA. MS analysis revealed that there is a ~30%-40% and ~10%-15% reduction, respectively, in METTL2 and 6 null-mutant cells, of $m^3C$ in total tRNA. Primer extension analysis located METTL2-modified $m^3C$ at position 32 of tRNAThr isoacceptors and tRNAArg (CCU). METTL6 interacts with seryl-tRNA synthetase in an RNA-dependent manner, suggesting a role for METTL6 in modifying serine tRNA isoacceptors. METTL8, on the other hand, modified mRNA, as determined by biochemical and genetic analyses in Mettl8 null-mutant mice and two human METTL8 mutant cell lines. Thus, inventors identified that Mettl8 catalyzes 3-methylcytidine ($m^3C$) formation in poly-A enriched RNA.

The discoveries of $m^3C$ modification in mRNA and of METTL8 as an mRNA $m^3C$ writer enzyme provide another aspect of this disclosure. Thus, the disclosure provides a method of inhibiting $m^3C$ formation in a cell comprising contacting the cells with a Mettl8 inhibitor.

In one embodiment, the Mettl8 inhibitor is a chemical, an antibody, a nucleotide sequence, or an enzyme. In another embodiment, the Mettl8 inhibitor comprises one or more of a CRISPR-Cas system directed to a Mettl8 gene, a Mettl8 variant, an shRNA, an RNAi, a miRNA, an interstrand crosslinking agent, an STAT3 inhibitor.

In another embodiment, the CRISPR system comprises at least one guide RNA ("gRNA") that hybridizes to the Mettl8 gene. In another embodiment, the CRISPR-Cas system, the shRNA, the RNAi, and/or miRNA are encoded by a recombinant vector. The recombinant vector is a retroviral vector, a lentiviral vector, a murine leukemia viral ("MLV") vector, an Epstein-Barr viral ("EBV") vector, an adenoviral vector, a herpes viral ("HSV") vector, or an adeno-associated viral ("AAV") vector. In one embodiment, the gRNA of the CRSIPR system comprises a sequence of SEQ ID No 9, SEQ ID No 10, SEQ ID No 11, SEQ ID No 12, SEQ ID No 13, or SEQ ID No 14. In another embodiment, the shRNA comprises a sequence of SEQ ID No. 2, SEQ ID No. 3, SEQ ID No. 4, SEQ ID No. 5, SEQ ID No. 6, SEQ ID No. 7, or SEQ ID No. 8.

The Mettl8 inhibitor can also be an interstrand crosslinking agent that comprises one or more of cisplatin and mitomycin C. In another embodiment, the Mettl8 inhibitor is a STAT3 inhibitor, which comprises static, STA-21, S31-201, or LLL12.

Cells with Reduced Expression of Mettl8

As noted above, reduced expression or gene knockout of Mettl8 can lead to hyper activation of ATM and affect KAP1, p53 and H2AX activities, which together result in orchestrated DNA repair response and cell cycle checkpoint maintenance. Through both genetic (e.g., CRISPR and shRNA) and non-genetic (e.g., cisplatin), inventors were able to reduce expression or activity of Mettl8 in a cell. In another aspect, the disclosure provides a composition comprising a cell having a reduced expression or activity of Mettl8 compared to a control. In one embodiment, the control is a similar or same type of cell with wide type and/or functional Mettl8. In one embodiment, the Mettl8 inhibitor is a chemical, an antibody, a nucleotide sequence, or an enzyme.

In another embodiment, the Mettl8 inhibitor comprises one or more of a CRISPR system directed to a Mettl8 gene, an shRNA, an RNAi, a miRNA, an interstrand crosslinking agent, an STAT3 inhibitor. In another embodiment, the CRISPR-Cas system comprises at least one guide RNA ("gRNA") that hybridizes to the Mettl8 gene. In on embodiment, the CRISPR-Cas system comprises at least one guide RNA ("gRNA") that hybridizes to the Mettl8 gene. In another embodiment, the CRISPR-Cas system is encoded by a recombinant vector. In one embodiment, the recombinant vector is a retroviral vector, a lentiviral vector, a murine leukemia viral ("MLV") vector, an Epstein-Barr viral ("EBV") vector, an adenoviral vector, a herpes viral ("HSV") vector, or an adeno-associated viral ("AAV") vector.

In one embodiment, the gRNA comprises a sequence of SEQ ID No 9, SEQ ID No 10, SEQ ID No 11, SEQ ID No 12, SEQ ID No 13, or SEQ ID No 14. In another embodiment, the shRNA comprises a sequence of a sequence of SEQ ID No. 2, SEQ ID No. 3, SEQ ID No. 4, SEQ ID No. 5, SEQ ID No. 6, SEQ ID No. 7, SEQ ID No. 8, or SEQ ID No. 15. In one embodiment, the cell is a cancer cell. In another embodiment, the cell is a mammalian cell. In one embodiment, the cell is a cell in a mammal. In another embodiment, the mammal comprises a mouse, a rat, a guinea pig, a non-human primate, a dog, a cat, a horse, a cow, a pig, a goat, a sheep, and/or human.

In one embodiment, the expression or activity of Mettl8 in the cell is reduced by more than 95%, 90%, 85%, 80%, 75%, 70%, 65%, 60%, 55%, 50%, 45%, 40%, 35%, 30%, 25%, 20%, 10%, 5%, or 1%.

Increased Sensitivity of Tumor Cells to a Therapy

Cisplatin is commonly used in the treatment of various cancers, including ovarian cancers. However, ovarian cancer often loses sensitivity to cisplatin and eventually develops resistance to the drug. Since the cisplatin-resistant ovarian cancer is no longer susceptible to the treatment, additional administration of cisplatin will not produce desired therapeutic effects, but rather will result in side effects. In such a case, the patients may need to consider other therapeutic options.

Camptothecin, a DNA topoisomerase I (TOP1) inhibitor, can interfere with tumor growth. However, de novo or acquired clinical resistance to camptothecin is also developed among patients, although the clinical resistance to camptothecins is still a poorly understood phenomenon.

Figure 8A:
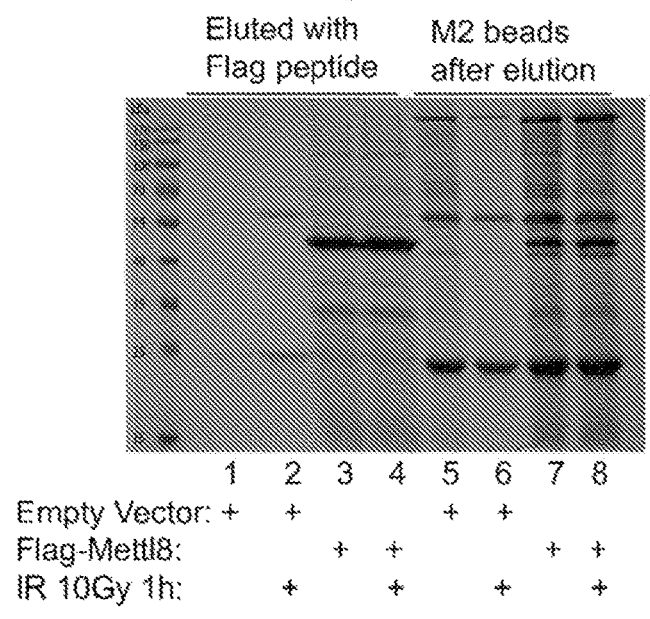
Figure 8C:
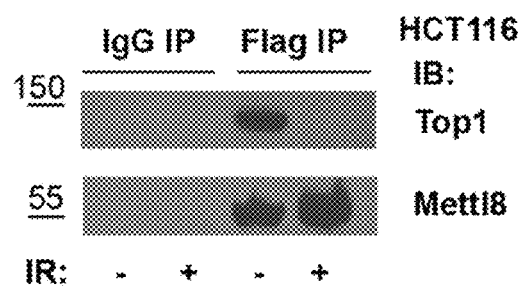
Figure 8C:
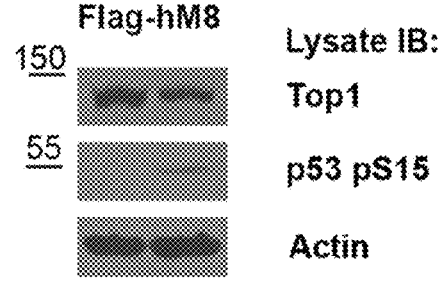

Surprisingly, inventors discovered that inhibition of Mettl8 in a tumor cell can increase the sensitivity of the cell to cancer therapy. For example, ATM was more activated (as evidenced by its phosphorylation status) in Mettl8 knockout cells than the wild type in presence of a TOP1 inhibitor (FIG. 8F). Also, inhibition of Mettl8 rendered the cells more sensitive to cisplatin treatment. Thus, in another embodiment, the present disclosure provides a method of rendering a tumor cell sensitive to a cancer therapy, comprising contacting the tumor cell with a Mettl8 inhibitor. In one embodiment, the Mettl8 inhibitor is a chemical, an antibody, a nucleotide sequence, or an enzyme. In another embodiment, the Mettl8 inhibitor comprises one or more of a CRISPR system directed to a Mettl8 gene, a Mettl8 variant, an shRNA, an RNAi, a miRNA, an interstrand crosslinking agent, an STAT3 inhibitor.

In another embodiment, the CRISPR system comprises at least one guide RNA ("gRNA") that hybridizes to the Mettl8 gene. In another embodiment, the CRISPR-Cas system, the shRNA, the RNAi, and/or miRNA are encoded by a recombinant vector. The recombinant vector is a retroviral vector, a lentiviral vector, a murine leukemia viral ("MLV") vector, an Epstein-Barr viral ("EBV") vector, an adenoviral vector, a herpes viral ("HSV") vector, or an adeno-associated viral ("AAV") vector. In one embodiment, the gRNA of the CRSIPR system comprises a sequence of SEQ ID No 9, SEQ ID No 10, SEQ ID No 11, SEQ ID No 12, SEQ ID No 13, or SEQ ID No 14. In another embodiment, the shRNA comprises a sequence of SEQ ID No. 2, SEQ ID No. 3, SEQ ID No. 4, SEQ ID No. 5, SEQ ID No. 6, SEQ ID No. 7, or SEQ ID No. 8.

In one embodiment, the tumor cell is drug-resistant. In another embodiment, the cancer therapy comprises one or more of cisplatin, 5'-fluorouracil, etoposide, irradiation, and a TOP1 inhibitor.

Topoisomerase I (TOP1) inhibitors include but are not limited to irinotecan, topotecan, camptothecin, lamellarine D, and their derivatives and analogs. In one embodiment, camptothecin includes but are not limited to homocamptothecin, DB67, BNP1350, exatecan, lurtototecan, ST1481 and CKD602, camptothecin, 9-aminocamptothecin, 9-nitrocamptothecin, 10-hydroxy camptothecin, 9-chloro-10,11-methylenedioxy (20S)-camptothecin (CMC), CPT-11, SN 38 and their derivatives and analogs. In one embodiment, the TOP1 inhibitors comprise camptothecin, topotecan, CPT-11, 9-aminocamptothecin, and 9-nitrocamptothecin. In one embodiment, the TOP1 inhibitors comprise camptothecin.

Pharmaceutical Compositions

In one aspect, the disclosure provides a pharmaceutical composition, wherein the pharmaceutical composition comprises a Mettl8 inhibitor, and a pharmaceutically acceptable carrier. In one embodiment, the Mettl8 inhibitor is a chemical, an antibody, a nucleotide sequence, or an enzyme.

The dosages of the Mettl8 inhibitor can vary among subjects. In some embodiments, the dosage to achieve the therapeutic effects of the Mettl8 inhibitor in the pharmaceutical composition is from about 0.1 mg/kg/day to about 100 mg/kg/day, from about 0.5 mg/kg/day to about 75 mg/kg/day, from about 1 mg/kg/day to about 50 mg/kg/day, from about 2 mg/kg/day to about 20 mg/kg/day, from about 2 mg/kg/day to about 15 mg/kg/day, or from about 4 mg/kg/day to about 10 mg/kg/day. In some embodiments, the dosage of imatinib is from about 0.1 mg/kg/day to about 100 mg/kg/day, from about 0.5 mg/kg/day to about 75 mg/kg/day, from about 1 mg/kg/day to about 50 mg/kg/day, from about 2 mg/kg/day to about 20 mg/kg/day, from about 2 mg/kg/day to about 15 mg/kg/day, or from about 4 mg/kg/day to about 10 mg/kg/day. In some embodiments, the dosage of imatinib is at least 0.1 mg/kg/day, at least 0.2 mg/kg/day, at least 0.3 mg/kg/day, at least 0.4 mg/kg/day, at least 0.5 mg/kg/day, at least 1 mg/kg/day, at least 2 mg/kg/day, at least 3 mg/kg/day, at least 4 mg/kg/day, at least 5 mg/kg/day, at least 6 mg/kg/day, at least 7 mg/kg/day, at least 8 mg/kg/day, at least 9 mg/kg/day, or at least 10 mg/kg/day.

In some embodiments, the pharmaceutical composition further comprises one or more of sorafenib, sunitinib, brivanib, bevacizumab, ramucirumab, vatalanib, linifanib, TSU-68, cediranib, erlotinib, nintedanib, regorafenib, cetuximab, lapatinib, cixutumumab, everolimus, sirolimus, and tivantinib.

A pharmaceutical composition can be formulated to be compatible with its intended route of administration. Examples of routes of administration include, but are not limited to, parenterally, orally, intraperitoneally, intravenously, intraarterially, transdermally, sublingually, intramuscularly, rectally, transbuccally, intranasally, liposomally, via minicells, via antibody conjugation, via cell targeting peptides, via inhalation, vaginally, intraocularly, via local delivery by catheter or stent, subcutaneously, intraadiposally, intraarticularly, or intrathecally. In a specific embodiment, the composition is formulated in accordance with routine procedures as a pharmaceutical composition adapted for parenterally, orally, intraperitoneally, intravenously, intraarterially, transdermally, sublingually, intramuscularly, rectally, transbuccally, intranasally, liposomally, via minicells, via antibody conjugation, via cell targeting peptides, via inhalation, vaginally, intraocularly, via local delivery by catheter or stent, subcutaneously, intraadiposally, intraarticularly, or intrathecally administration to human beings. Where necessary, the composition may also include a solubilizing agent and a local anesthetic such as lignocamne to ease pain at the site of the injection. In some embodiments, the composition may be formulated as a sterile aqueous solution suitable for injection intravenously, subcutaneously, intraperitoneally, or intramuscularly.

In one embodiment, the pharmaceutical compositions can be formulated orally in the form of tablets, capsules, cachets, gelcaps, solutions, or suspensions. The tablets may be coated by methods well-known in the art. Liquid preparations for oral administration may take the form of, but not limited to, solutions, syrups or suspensions, or they may be presented as a dry product for constitution with water or other suitable vehicle before use.

In some embodiments, the pharmaceutical compositions comprise one or more of binding agents, flavor agents, lubricating agents, flow agents, disintegration agents, delay agents, and organic solvents. In some embodiments, the binding agents comprise starch, modified starch, cellulose, modified cellulose, brewer's yeast, sucrose, dextrose, whey, and dicalcium phosphate. In some embodiments, the lubricating agents comprise magnesium stearate, stearic acid, starch, modified starch, and modified cellulose. In some embodiments, the flow agents comprise silica dioxide, modified silica, fumed silica, and talc. In some embodiments, the disintegration agents comprise croscarmellose sodium, sodium starch glycolate, starch, and modified starch. In some embodiments, the delay agents comprise one or more of stearic acid, stearic acid salts, magnesium stearate, polyethylene glycols, starch, modified starch, and methacrylate polymers. In some embodiments, the organic solvents comprise propylene glycol, polyethylene glycols, ethanol, dimethyl sulfoxide (DMSO), N-methyl-2-pyrrolidone, glycofurol, Solketal, glycerol formal, acetone, tetrahydrofurfuryl alcohol, diglyme, dimethyl isosorbide, and ethyl lactate. In some embodiments, the concentration of the organic solvent is 0.1% to about 35% of the total volume of the composition.

In some embodiments, the concentration of the organic solvent is 2% of the total volume of the composition.

Accordingly, all such modifications are intended to be included within the scope of the present disclosure. Furthermore, the order or sequence of any process or method steps may be varied or re-sequenced according to alternative embodiments. Other substitutions, modifications, changes, and omissions may be made in the design, operating conditions, and arrangement of the exemplary embodiments without departing from the scope of the present disclosure.

Modes of administration include oral, rectal, topical, nasal, intradermal, or parenteral routes. The term "parenteral" includes subcutaneous, intravenous, intramuscular, or infusion. Intravenous or intramuscular routes are not particularly suitable for long-term therapy and prophylaxis. Oral administration is used in prophylactic treatment because of the convenience to the patient as well as the dosing schedule.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Delivery systems that targets specific tissues is used for effective treatment of cancer to reduce toxic side effects on unintended tissues. Many types of delivery systems for targeted release of drugs are available and known to those of ordinary skill in the art, including controlled-release biodegradable polymers, polymeric microsphere carriers and liposomes, as well as the co-administration of cytoprotective agents with antineoplastics as described in Chonn and Cullis, *Curr. Opinion in Biotechnology*, 6: 698-708 (1995); Kemp et al., *J. Clin. Oncol.*, 14: 2101-2112 (1996); Kumanohoso et al., *Cancer Chemother. Pharmacol*, 40: 112-116 (1997); Schiller et al., *J. Clin. Oncol*, 14: 1913-1921 (1996); and Sipos et al., *Cancer Chemother. Pharmacol*, 39: 383-389 (1997). The liposomes can be further coated with polyethene glycol (PEG) to prolong their circulation time. Furthermore, targeted delivery of the drugs can be achieved by using minicells as described in WO 2005/079854. The minicells comprises a first arm that carries specificity for a bacterially derived minicell surface structure and a second arm that carries specificity for a mammalian cell surface receptor, to target drug-loaded minicells to specific mammalian cells and to cause endocytosis of the minicells by the mammalian cells. Accordingly, in some embodiment the pharmaceutical composition is administered in a targeted release system.

Compositions suitable for oral administration may be presented as discrete units, such as capsules, tablets, or lozenges, each containing a predetermined amount of the active agent(s). Other compositions include suspensions in aqueous liquids or non-aqueous liquids such as a syrup, an elixir, or an emulsion.

Other delivery systems can include time-release, delayed-release, or sustained-release delivery systems. Such systems can avoid repeated administrations of the pharmaceutical composition of this invention, increasing convenience to the subject and the physician. Many types of release delivery systems are available and known to those of ordinary skill in the art. They include polymer-based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids, including sterols such as cholesterol, cholesterol esters, and fatty acids or neutral fats such as mono-, di-, and tri-glycerides; hydrogel release systems; sylastic systems; peptide-based systems; wax coatings; compressed tablets using conventional binders and excipients; partially fused implants; and the like.

In one embodiment, the pharmaceutical composition is administered in a time-release, delayed-release, or sustained-release delivery system. In one embodiment, the time-release, delayed-release, or sustained-release delivery system comprising the pharmaceutical composition of the invention is inserted directly into the tumor.

When administered, the pharmaceutical preparations of the invention are applied in pharmaceutically acceptable amounts and in pharmaceutically acceptable compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium, or calcium salts.

Kit of Parts

In one aspect, this invention relates to a kit of parts for treatment of a cancer in a subject, the kit comprising a Mettl8 inhibitor. In one embodiment, the cancer is one or more of pancreatic cancer, renal cancer, small cell lung cancer, brain cancer, neural cancer, bone cancer, lymphoma, myeloma, colon cancer, uterine cancer, breast cancer, leukemia, liver cancer, prostate cancer, skin cancer, and melanoma.

In another embodiment, the kit further comprises sorafenib, sunitinib, brivanib, bevacizumab, ramucirumab, vatalanib, linifanib, TSU-68, cediranib, erlotinib, nintedanib, regorafenib, cetuximab, lapatinib, cixutumumab, everolimus, sirolimus, and tivantinib.

In one embodiment, the kit further comprises instructions for treating the cancer. In one embodiment, the kit of parts comprises instructions for dosing and/or administration of the pharmaceutic composition of this invention.

Working Examples

The following examples are for illustrative purposes only and should not be interpreted as limitations of the claimed invention. There are a variety of alternative techniques and procedures available to those of skill in the art which would similarly permit one to successfully perform the intended invention.

Example 1 Modulation of Mettl8 Expression

Screening for STAT3 target genes was performed with immortalized mouse liver cells in the presence or absence of STAT3, which identified Methyltransferase like protein 8 (Mettl8) as a target gene for STAT3.

To study the functions of Mettl8, hairpin shRNA was ordered and cloned into pLKO1 vector by AgeI/EcoRI, with the following sequence:

```
                                           (SEQ ID NO: 15)
CCGGGTTGAGGGAATTTCCTGAAATCTCGAGATTTCAGGAAATTCCCTCAA

CTTTTTTG.
```

Figure 2:
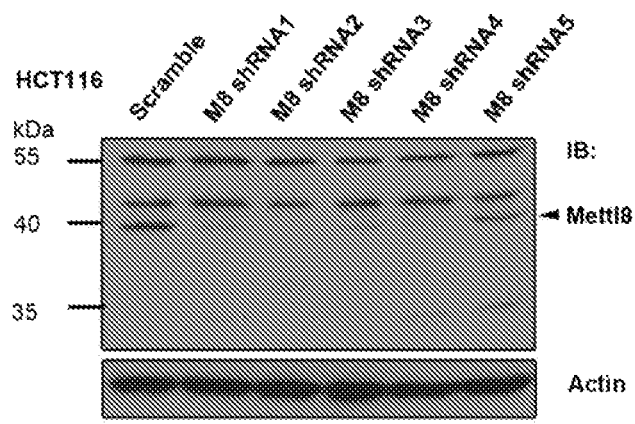
FIG. 2 shows modulation of Mettl8 protein level by shRNA-mediated knockdown.

The hairpin sequences in the shRNA were underlined. Lentivirus was prepared by co-transfection the pLKO1 vector with helper plasmids coding VSV-G and Gag protein into 293T cells. Supernatant was harvested after 48 hours and cleared by filtration. Then viral solution was added to fresh HCT116 culture in the presence of 6 ug/ml polybrene. After 72 h, the cells were lysed and equal amount of lysate was resolved on SDS-PAGE for knock down efficiency by Western blotting with anti-Mettl8 and actin antibodies as indicated in FIG. 2. The results show that the shRNA can knock down the expression of Mettl8 expression.

Figure 3A:
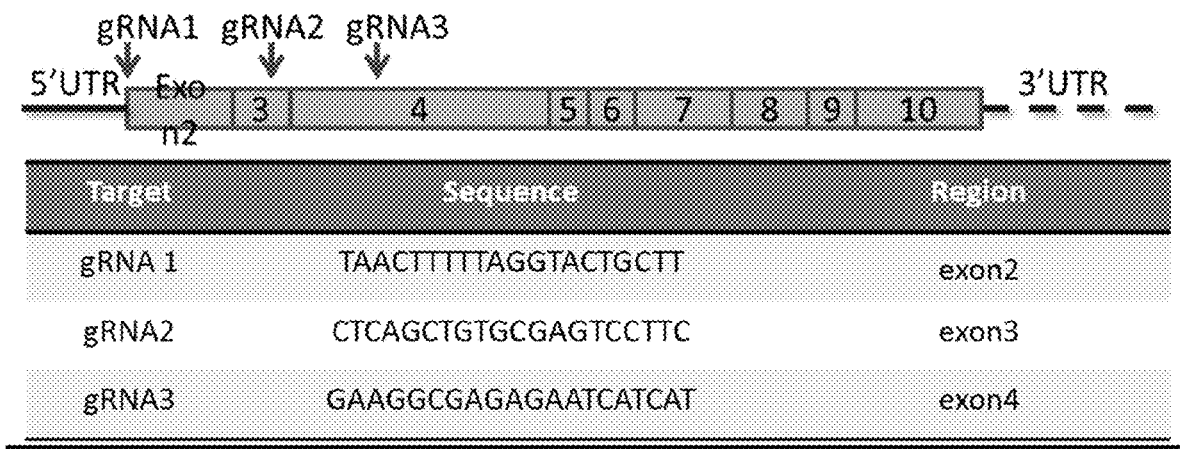
FIG. 3A discloses SEQ ID NOS 9-11, respectively, in order of appearance.
Figure 3B:
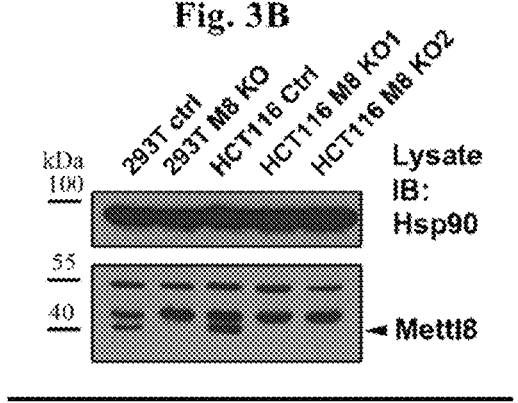
FIG. 3 shows ablation of Mettl8 protein expression by CRISPR technology.
FIG. 3C discloses SEQ ID NOS 20, 21, 34, 22, 23, 35, 24, 25, and 36, respectively, in order of appearance.
FIG. 3D discloses SEQ ID NOS 26-27, respectively, in order of appearance.
FIG. 3E discloses SEQ ID NO: 28.

Mettl8 knockout mouse models were generated using CRISPR-mediated mutagenesis technology. Three gRNAs were co-injected along with Cas9 mRNA into mouse embryos respectively, in which the deletion mutants were screened. The schematic diagram of human Mettl8 mRNA structure and the gRNA sequences are shown in FIG. 3A. Equal amount of lysates from different Mettl8 knockout clones and controls were resolved on gel and probed with Hsp90 and Mettl8 antibodies (FIG. 3B, arrowhead points to the band of Mettl8 endogenous protein). The sequencing results of individual knockout clones genomic DNA were aligned to the respective target region of each gRNA used (FIG. 3C), with deletion of various lengths shown with each gRNA underlined.

More specifically, during the generation of Mettl8 knockout mouse model by CRISPR technology, three gRNAs targeting Mettl8 mRNA coding region were injected into mouse embryo (FIG. 3D). The pups were screened for genetic mutation by sequencing. Several clones obtained and one clone with longest deletion (92 bp) were chosen which caused frameshift and premature termination of Mettl8 transcript. The results for sequencing validation of deletion mutant are shown in FIG. 3E, in which the region in blue is deleted (92 bp). Protein lysates of brain tissue from E14 mouse embryo were analyzed on SDS-PAGE and probed for antibodies indicated (FIG. 3F). The upper band corresponding to Mettl8 protein was undetectable in homozygous knockout pups. The results show that the CRISPR technology effectively ablated the Mettl8 expression in the mouse model.

Figure 4:
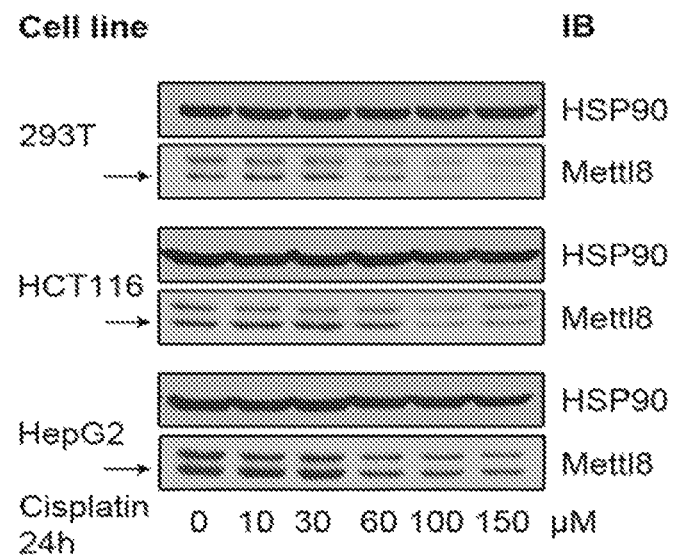
FIG. 4 shows suppression of Mettl8 protein expression by cisplatin treatment.

To further study modulation of Mettl8 protein, 293T, HCT116, and HepG2 cells were treated with different dosage of cisplatin (0, 10, 30, 60, 100, and 150 µM) for 24 h before cell lysates were collected and subjected to SDS-PAGE followed by immunoblotting with Mettl8 and Hsp90 antibodies. As shown in FIG. 4, Mettl8 protein in human cancers was dramatically reduced.

In aforementioned screening for STAT3 target genes, Inventors created the first cell line without STAT3 by clean-cut genetic approach in the laboratory. The cells were originated from C57BL/6 background with TTR-Cre driven STAT3 deletion in adult liver. To make a parallel control, STAT3 was reintroduced into the parental STAT3 knockout cell to generate STAT3+ liver cell. The expression of STAT3 was not detectible in original knockout cell, but was restored in the STAT3+ cells (FIG. 5A). STAT3 showed expected phosphorylation pattern at Tyrosine 705 when treated with 10 ng/ml murine OSM (a potent activator for STAT3) for the indicated periods in FIG. 5A. 300 pairs of primers were chosen to screen the mRNA level in STAT3−/+ liver cells by qPCR between untreated and OSM treated cells (1 hr). The shortlisted genes with obvious changes are presented in FIG. 5B, among which is Mettl8. The positive control is a known STAT3 target gene.

By analyzing promoter sequence of this gene, inventors found two STAT3 consensus sites, one very close (−146 bp) to TSS (transcription start site) and another one at distal region (about 6.2 kb upstream) (FIG. 5C). Two AP-1 sites are also present at −433 and −989 bp, which could be accounted for the induction by OSM in the absence of STAT3, as OSM can also activate MAPK pathway.

To confirm the binding of STAT3 to the promoter region, ChIP was performed with $10^7$ STAT3+ liver cells treated with OSM for different time points. Equal amount of eluted DNA was amplified in normal PCR to detect region of two binding sites (P1 and P2). As shown in FIG. 5D, a similar sized region on Gapdh gene was amplified against input DNA as internal control (left panel). The same experiment was carried out with qPCR to show the enrichment of STAT3 binding site as compared to percentage of the equal amount of input DNA (right panel of FIG. 5D).

Luciferase reporting assay was also carried out with pGL3-M67-SIE, pGL4-Mettl8-b(wild-type) and STAT3 site mutated vector in STAT3+ liver cell. As shown in FIG. 5E, STAT3 activated the Mettl8 promoter activity. FIG. 5F shows the UCSC genome browser screen capture of the STAT3 binding site on human Mettl8 gene with multi-alignment of different mammalian sequences on the same region. The STAT3 binding sites were underlined in FIG. 5F. STAT3 ChIP assay was also performed in human lung cancer cell H1650. The enrichment on STAT3 binding site was quantified by qPCR with primers specific to the region (FIG. 5G).

To investigated how STAT3 crosstalk with other potential pathways in pluripotency of embryonic stem cells ("ESCs"), inventors tried to identify factors that were regulated by STAT3 using mouse ESCs treated with STAT3 inhibitors STA-21 and STATTIC. Real-time PCR was performed to screen for changes when embryonic stem cells (ESCs) were treated with STAT3 inhibitor 10 µM STA-21 and STATTIC for 1 hr. RNAs were extracted with TRIZOL followed by reverse transcription. Mettl8 mRNA was among the genes downregulated during the process as shown in FIG. 5H.

Figure 5J:
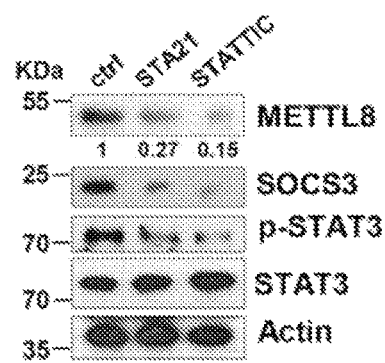

Total RNAs were extracted from E14 cells treated with STA-21 and STATTIC for 6 hr and analyzed by real-time PCR. As shown in FIG. 5I, Mettl8 mRNA expression was inhibited by STA-21 and STATTIC. The data are shown as the mean±SD from three independent experiments (*$p<0.05$). The cell lysates from treated E14 cells were also analyzed by Western blot. Consistent with the mRNA expression, the protein levels of Mettl8 were reduced with presence of STA-21 and STATTIC (FIG. 5J). The value of each band was calculated from three independent replicates and indicates the relative expression level after normalizing to the loading control Actin.

Figure 5K:
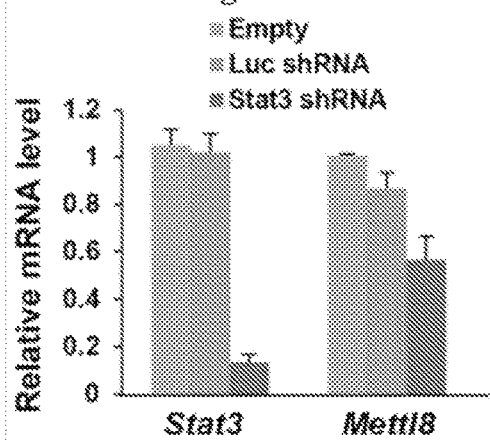
Figure 5L:
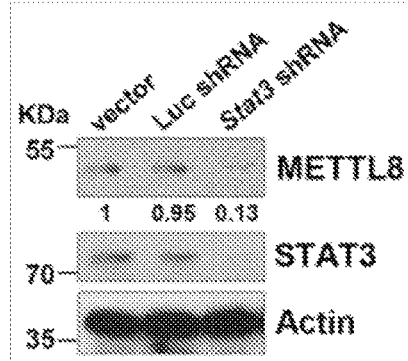

Knockdown of STAT3 with shRNA in E 14 cells resulted in downregulation of Mettl8 mRNA (FIG. 5K) and Mettl8 protein (FIG. 5L). Luc shRNA was used as control. Data in FIG. 5K are shown as the mean±SD from three independent experiments. The value of each band in FIG. 5L was calculated from three independent replicates and indicates the relative expression level after normalizing to the loading control Actin.

Figure 5M:
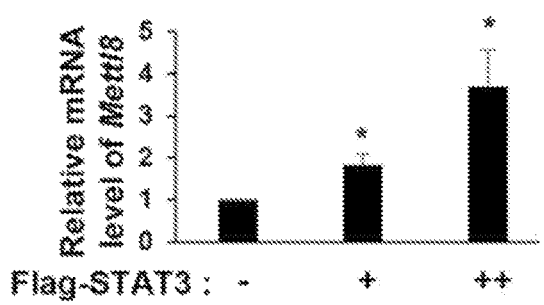
Figure 5N:
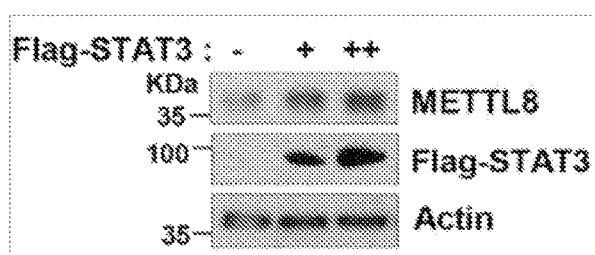

Overexpression of STAT3 increased the mRNA and protein expressions of Mettl8 (FIG. 5M and FIG. 5N). In this experiment, E14 cells were transfected with Flag-vector or Flag-tagged STAT3 at increasing concentrations. Total RNAs were extracted followed by real-time PCR analysis. Data in FIG. 5M are shown as the mean±SD from three independent experiments (*$p<0.05$).

Example 2 Inhibition of Mettl8 Modulates $m^3C$ Level in mRNA

Mettl8 has an SAM (S-adenosyl-Methionine) binding domain, which consists of seven-stranded beta sheet with three helices on each side. The primary sequence may have variance but they define the Rossmann fold, hallmark structure of class I methyltransferase. The N-terminal region of the core fold contains highly conserved glycine-rich sequence E/DXGXGXG (often referred to as motif I) between β1 and αA, which interacts with the amino acid portion of SAM.

To test the ability of Mettl8 to bind SAM, equal amounts of GST, GST-Mettl8 WT and mutant proteins were conjugated on Glutathione sepharose 4B beads and incubated with $^3$H-SAM for 30 min at 30° C. with empty beads control. After extensive washing, the beads were transferred to scintillation tubes and measured on liquid scintillation counter in triplicate. As shown in FIG. 6A, Mettl8 binds directly with $^3$H-SAM, but mutation of Mettl8 SAM binding domain abolished its binding activity to $^3$H-SAM.

mRNA was extracted from the liver tissue of different mouse strains (WT: wide type; M8 knockout (Mettle8 knockout); M2 knockout (Mettle2 knockout); M6 knockout (Mettle6 knockout). After poly(A) enrichment and removal of rRNA, digested single nucleoside were resolved on Liquid Chromatography-MS/MS (Mass Spectrometry). As in FIG. 6B, chromatography for $m^3C$ and its quantification in mouse liver tissues with different genetic ablations were shown at right panel, and the quantification of $m^3C$ in total cytidine was shown on the left panel. Only in Mettl8 knockout but not Metl12 or Mettl6 knockout mice was the $m^3C$ modification was ablated.

A similar procedure was performed on mRNA from human HCT116 cells with wild-type or Mettl8 knockout. As in FIG. 6C, LC-MS/MS chromatography and quantification of $m^3C$ levels in one pair of HCT116 was shown on the right panel, and the quantification result was shown on the left panel. The results showed that $m^3C$ level was dramatically reduced in Mettl8 knockout samples compared to wild-type control.

Figure 6D:
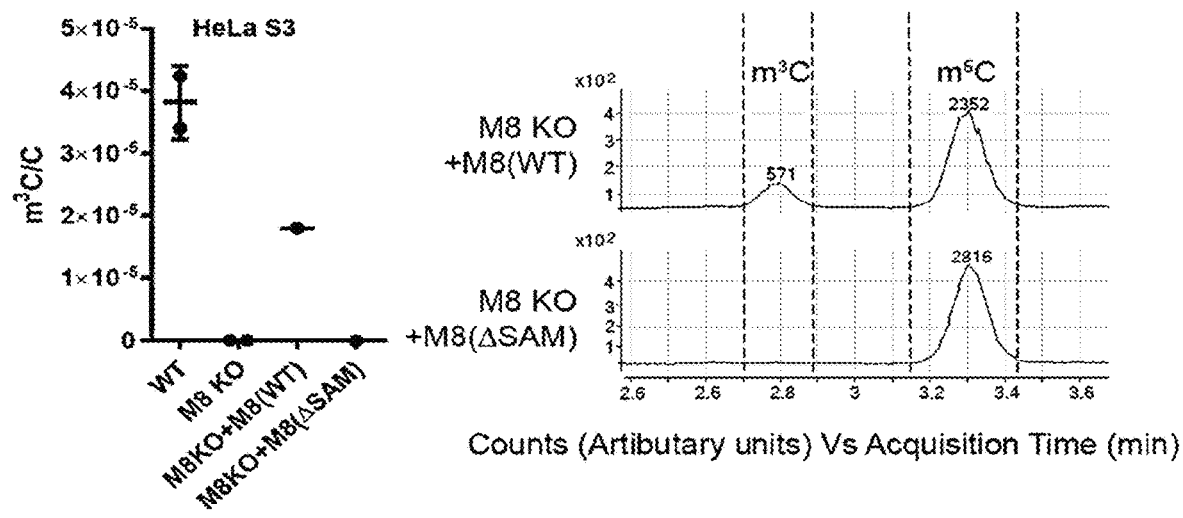

FIG. 6D shows LC-MS/MS chromatography and quantification of $m^3C$ levels in HeLa S3 cell with Mettl8 wildtype, knockout, and knockout cells rescued by introducing Mettl8 WT or SAM mutant cDNA. The value of $m^3C$ is presented relative to canonical cytidine. Data with error bars represent mean±SD for at least 3 biological replicates. Mettl8 knokcout cells showed abolished level of $m^3C$ ratio in total cytidine compared to wildtype control. HeLa knockout cells rescued with Mettl8 wild-type cDNA showed partially restored m3C level, but not in cells rescued with a mutant Mettl8 (FIG. 6D).

Inventors also identified possible Mettl8 $m^3C$-containing mRNAs as listed in Table 3. Here, total RNA from WT or Mettl8 Knock-out HeLa cell and mouse liver cells were subject to small RNA exclusion, poly(A) enrichment, $m^3C$ antibody pull-down and RNA-seq analysis. The procedure was adapted from m1A pull-down seq. Total RNA was extracted by Trizol™ Column based large RNA enrichment and size exclusion chromatography was used to reduce tRNA contents. Oligo-dT Dyna beads were used to enrich poly(A) tailed mRNA. RNA fragmentation were performed using NEB fragmentation module for 4 min at 94 degrees; the fragmented RNA were ethanol precipitated with the aid of Glyco-blue, and dissolved in Tris (7.5, 10 mM), 10% was saved for RNA-seq. The remaining fragmented RNA was used for $m^3C$-IP. The RNA bound by the $m^3C$ antibody were eluted with 10 mM to 20 mM $m^3C$ nucleoside (Carbosynth) and subject to NEBnext Ultra stranded library preparation and Illumina HiSeq High Output 2×101 bp (multiplexed) sequencing.

TABLE 3

Mettl8 M³C RIP sequence targets

| chr | start | end | fold_enrichment | region | refgene_TSSpm1kb | all_mRNA_TSSpm1kb_ACC_ol | refgene_Symbol_ol | refgene_TSSpm1kb_Symbol_ol | refgene_TSSpm1kb_Symbol_ln | refgene_TSSpm1kb_Symbol_rn |
|---|---|---|---|---|---|---|---|---|---|---|
| chr1 | 11648416 | 11648840 | 8.43558 | chr1:11648416-11648840 | | | | PTCHD2 | | LOC101929181 |
| chr1 | 11649136 | 11649239 | 5.5 | chr1:11649136-11649239 | | | | PTCHD2 | | LOC101929181 |
| chr1 | 11649976 | 11650086 | 8.91581 | chr1:11649976-11650086 | | | | PTCHD2 | | LOC101929181 |
| chr1 | 11650495 | 11650814 | 9.18598 | chr1:11650495-11650814 | | | | PTCHD2 | | LOC101929181 |
| chr1 | 16613365 | 16613449 | 7.29475 | chr1:16613365-16613449 | | AK027902 // AK096437 // AY037157 // BC035725 | FBXO42 | RSG1 | | FBXO42 |
| chr1 | 27668284 | 27668342 | 6.21405 | chr1:276 68284-27668342 | SYTL1 // SYTL1 | | | LOC644961 | | MAP3K6 |
| chr1 | 36322069 | 36322139 | 7.02457 | chr1:36322069-36322139 | | | AGO4 | AGO4 | | AGO1 |
| chr10 | 18691869 | 18691912 | 8.91581 | chr10:18691869-18691912 | | | | ADARB2 | | LINC00700 |
| chr10 | 18708773 | 18710833 | 6.1119 | chr10:18707773-18710833 | | | | ADARB2 | | LINC00700 |
| chr10 | 131110329 | 131110387 | 8.64563 | chr10:131110329-131110387 | | | CCDC3 | CCDC3 | | CCDC3 |
| chr10 | 131116275 | 131116312 | 6.21405 | chr10:131116275-131116312 | | | | CCDC3 | | CCDC3 |
| chr10 | 131118881 | 131119013 | 7.02457 | chr10:131118881-131119013 | | | CCDC3 | CCDC3 | | CCDC3 |
| chr10 | 131123985 | 131124028 | 7.56493 | chr10:131123985-131124028 | | | CCDC3 | CCDC3 | | CCDC3 |
| chr10 | 131125940 | 131126012 | 7.02457 | chr10:131125940-131126012 | | | CCDC3 | CCDC3 | | CCDC3 |
| chr10 | 131127738 | 131127827 | 6.48422 | chr10:131127738-131127827 | | | CCDC3 | CCDC3 | | CCDC3 |
| chr11 | 19957725 | 19951995802 | 7.109 | chr11:19957725-1995802 | AK126915 | | | MRPL23 | | MRPL23-AS1 |
| chr11 | 19961156 | 19961996207 | 9.45808 | chr11:19961156-1996207 | AK126915 // AK126380 | | | MRPL23 | | MRPL23-AS1 |
| chr11 | 19961354 | 19961996431 | 10.53186 | chr11:19961354-1996431 | AK126915 // AK126380 | | | MRPL23 | | MRPL23-AS1 |
| chr11 | 64152331 | 64152388 | 6.33333 | chr11:64152331-64152388 | | | | MIR1237 | | LOC100996455 |

TABLE 3-continued

| chr | start | end | fold_enrichment | region | refgene_TSSpm1kb_Symbol_ol | Mettl8 M³C RIP sequence targets all_mRNA_TSSpm1kb_ACC_ol | refgene_Symbol_ol | refgene_TSSpm1kb_Symbol_ol | refgene_TSSpm1kb_Symbol_ln | refgene_TSSpm1kb_Symbol_rn |
|---|---|---|---|---|---|---|---|---|---|---|
| chr11 | 65422868 | 65422905 | 5.10018 | chr11:65422868-65422905 | | | RELA // RELA // RELA // RELA | MIR4489 | | RELA |
| chr12 | 10378585 | 10378671 | 7.56493 | chr12:10378585-10378671 | | BC042884 | | GABARAPL1 | | KLRD1 |
| chr12 | 10388806 | 10388854 | 7.8351 | chr12:10388806-10388854 | | | | GABARAPL1 | | KLRD1 |
| chr12 | 88130330 | 88130421 | 6.21405 | chr12:88130330-88130421 | | | | MGAT4C | | MKRN9P |
| chr13 | 45975418 | 45975514 | 5.25 | chr13:45975418-45975514 | | CR627474 | SLC25A30 // SLC25A30 // SLC25A30 | TPT1-AS1 | | SLC25A30 |
| chr13 | 1.13E+08 | 1.13E+08 | 7.29475 | chr13:113087283-113087357 | | | SPACA7 | SPACA7 | | TUBGCP3 |
| chr13 | 1.13E+08 | 1.13E+08 | 8.37545 | chr13:113096367-113096445 | | | | SPACA7 | | TUBGCP3 |
| chr13 | 1.13E+08 | 1.13E+08 | 7.6356 | chr13:113096765-113096853 | | | | SPACA7 | | TUBGCP3 |
| chr14 | 52010906 | 52010972 | 7.56493 | chr14:52010906-52010972 | | | FRMD6-AS2 // FRMD6 | FRMD6 | | FRMD6-AS2 |
| chr14 | 52068788 | 52068935 | 8.64563 | chr14:52068788-52068935 | | | FRMD6 | FRMD6-AS2 | | FRMD6-AS1 |
| chr14 | 58535691 | 58535793 | 7.8351 | chr14:58535691-58535793 | | | | SLC35F4 | | C14orf37 |
| chr15 | 64950997 | 64951102 | 6.7544 | chr15:64950997-64951102 | | | ZNF609 | ZNF609 | | OAZ2 |
| chr15 | 64951890 | 64951941 | 6.28019 | chr15:64951890-64951941 | | | ZNF609 | ZNF609 | | OAZ2 |
| chr15 | 64952193 | 64952292 | 6.95479 | chr15:64952193-64952292 | | | ZNF609 | ZNF609 | | OAZ2 |
| chr15 | 64952729 | 64952918 | 6.48422 | chr15:64952729-64952918 | | | ZNF609 | ZNF609 | | OAZ2 |
| chr15 | 64954493 | 64954700 | 5.5 | chr15:64954493-64954700 | | | ZNF609 | ZNF609 | | OAZ2 |
| chr15 | 92882872 | 92882913 | 7.00483 | chr15:92882872-92882913 | | | | SLCO3A1 | | ST8SIA2 |
| chr16 | 3069263 | 3069311 | 6.90184 | chr16:3069263-3069311 | | | | CLDN6 | | TNFRSF12A |
| chr16 | 30076354 | 30076427 | 5.66667 | chr16:30076354-30076427 | ALDOA // ALDOA // ALDOA // ALDOA | FJ474908// M11560 // BC016800 // BC013614 // BX647566 // D28356 // BC010660 // X05236 // | ALDOA // ALDOA // ALDOA | ALDOA | | |
| chr16 | 30073007 | 30076427 | | | | | | | | PPP4C |

TABLE 3-continued

Mettl8 M³C RIP sequence targets

| chr | start | end | fold_enrichment | region | refgene_TSSpm1kb_Symbol_ol | all_mRNA_TSSpm1kb_ACC_ol | refgene_Symbol_ol | refgene_TSSpm1kb_Symbol_ol | refgene_TSSpm1kb_Symbol_ln | refgene_TSSpm1kb_Symbol_m |
|---|---|---|---|---|---|---|---|---|---|---|
| chr 17 | 4228 8475 | 4228 8534 | 5.79252 | chr17:42288475-42288534 | | DL492329 // DL490818 // AK026577 // BC012880 // BC015888 // AK301993 | UBTF // UBTF // UBTF // UBTF | MIR6782 | | UBTF |
| chr 17 | 6782 6191 | 6782 6254 | 6.1119 | chr17:67826191-67826254 | | | LOC10192 8122 // LOC10192 8122 | LOC101928122 | | LOC102723487 |
| chr 17 | 7591 4195 | 7591 4262 | 6.20964 | chr17:75914195-75914262 | | | | FLJ45079 | | TNRC6C |
| chr 17 | 7591 5048 | 7591 5104 | 6.11085 | chr17:75915048-75915104 | | | | FLJ45079 | | TNRC6C |
| chr 18 | 4802 0402 | 4802 0526 | 7.29475 | chr18:48020402-48020526 | | | | SKA1 | | MAPK4 |
| chr 19 | 9981 82 | 9982 90 | 7.24638 | chr19:998182-998290 | | | | WDR18 | | GRIN3B |
| chr 19 | 2417 753 | 2418 173 | 7.02457 | chr19:2417753-2418173 | | | | TMPRSS9 | | TIMM13 |
| chr 19 | 3557 381 | 3557 481 | 5.55556 | chr19:3557381-3557481 | MFSD12 // MESD12 | DQ895484 // DQ892284 // CU691388 // BC036706 // BC094804 // BC068439 | MFSD12// MFSD12 | C19orf71 | | HMG20B |
| chr 19 | 3379 6554 | 3379 6704 | 5.83333 | chr19:33796554-33796704 | | | | | CEBPA-AS1l CEBPG | |
| chr 19 | 4619 6388 | 4619 6487 | 8.68878 | chr19:46196388-46196487 | SNRPD2 // SNRPD2 // QPCTL // QPCTL | AK000091 // AK172764 // AK222636 // BC011553 // AB528634 | QPCTL // QPCTL | MIR642B | | FBX046 |
| chr 19 | 4619 7357 | 4619 7514 | 6.45474 | chr19:46197357-46197514 | | | QPCTL // QPCTL ROCK2 | QPCTL | | FBX046 |
| chr 2 | 1140 2027 | 1140 2064 | 7.29475 | chr2:11402027-11402064 | | | ROCK2 | PQLC3 | | ROCK2 |
| chr 2 | 1140 2229 | 1140 2987 | 8.64563 | chr2:11402229-11402987 | | | | PQLC3 | | ROCK2 |
| chr 2 | 3286 6912 | 3286 6970 | 8.69963 | chr2:32866912-32866970 | | | TTC27 // TTC27 | MIR4765 | | LINC00486 |
| chr 2 | 9531 4480 | 9531 4617 | 7.3723 | chr2:95314480-95314617 | | | | ACTR3BP2 | | FAM95A |

TABLE 3-continued

Mettl8 M³C RIP sequence targets

| chr | start | end | fold_enrichment | region | refgene_TSSpm1kb_Symbol_ol | all_mRNA_TSSpm1kb_ACC_ol | refgene_Symbol_ol | refgene_TSSpm1kb_Symbol_ln | refgene_TSSpm1kb_Symbol_m |
|---|---|---|---|---|---|---|---|---|---|
| chr 2 | 95315239 | 95315629 | 8.37545 | chr2:95315239-95315629 | | | | ACTR3BP2 | FAM95A |
| chr 2 | 95318192 | 95318233 | 6.48422 | chr2:95318192-95318233 | | | | ACTR3BP2 | FAM95A |
| chr 2 | 95319449 | 95319678 | 7.56493 | chr2:95319449-95319678 | | | | ACTR3BP2 | FAM95A |
| chr 2 | 95320513 | 95320663 | 8.10528 | chr2:95320513-95320663 | | | | ACTR3BP2 | FAM95A |
| chr 2 | 95321101 | 95321190 | 6.48422 | chr2:95321101-95321190 | | | | ACTR3BP2 | FAM95A |
| chr 2 | 2.32E+08 | 2.32E+08 | 7.41309 | chr2:232457248-232457298 | C2orf57 | | | NMUR1 | PTMA |
| chr 2 | 2.32E+08 | 2.32E+08 | 5.68182 | chr2:232458857-232458948 | | BC024251 // BC063389 // 8C034405 // DQ891288 // DQ894472 | | C2orf57 | PTMA |
| chr 2 | 2.32E+08 | 2.32E+08 | 6.66667 | chr2:232460072-232460220 | | | | C2orf57 | PTMA |
| chr 2 | 232E+08 | 232E+08 | 12.79181 | chr2:232460367-232460736 | | | | C2orf57 | PTMA |
| chr 20 | 44745675 | 44745797 | 7.02457 | chr20:44745675-44745797 | | | | NCOA5 | CD40 |
| chr 20 | 44745914 | 44746154 | 6.7544 | chr20:44745914-44746154 | CD40 // CD40 | BC064518 // BC012419 // X60592 // AK222896 // AJ300189 // AB209660 // AB590222 // DQ891804 // DQ894988 // BT019901 // AY225405 // AX781593 | | NCOA5 | CDH22 |
| chr 20 | 63488263 | 63488389 | 7.8351 | chr20:63488263-63488389 | | | | LINC00266-1 | |
| chr 20 | 63494936 | 63495106 | 7.56493 | chr20:63494936-63495106 | | | | L1NC00266-1 | |
| chr 21 | 45990968 | 45991007 | 7.8351 | chr21:45990968-45991007 | KRTAP10-4 | AB076351 // BC125048 // KRTAP10-4 // BC021197 // AJ566382 | TSPEAR // TSPEAR | KRTAP10-3 | KRTAP10-4 |
| chr 21 | 45994164 | 45994203 | 7.8351 | chr21:45994164-45994203 | BC125049 | | TSPEAR // TSPEAR | KRTAP10-3 | KRTAP10-5 |
| chr 3 | 9649622 | 9649707 | 5.67369 | chr3:9649622-9649707 | | | | LHFPL4 | MTMR14 |
| chr 3 | 19947242 | 19947380 | 7.8351 | chr3:19947242-19947380 | | | EFHB | MIR4791 | EFHB |
| chr 3 | 48567753 | 48567879 | 7.02457 | chr3:48567753-48567879 | | | PEKFB4 | SHISA5 | MIR6823 |
| chr 3 | 48568114 | 48568177 | 7.56493 | chr3:48568114-48568177 | | | PEKFB4 | SHISA5 | MIR6823 |
| chr 3 | 48568818 | 48568863 | 6.21405 | chr3:48568818-48568863 | | | PEKFB4 | SHISA5 | MIR6823 |

TABLE 3-continued

| | | | | | | Mettl8 M³C RIP sequence targets | | | |
|---|---|---|---|---|---|---|---|---|---|
| chr | start | end | fold_enrichment | region | refgene_TSSpm1kb_Symbol_ol | all_mRNA_TSSpm1kb_ACC_ol | refgene_Symbol_ol | refgene_TSSpm1kb_Symbol_ln | refgene_TSSpm1kb_Symbol_m |
| chr3 | 48579644 | 48579686 | 8.91581 | chr3:48579644-48579686 | | | PEKFB4 | SHISA5 | MIR6823 |
| chr3 | 1.61E+08 | 1.61E+08 | 8.22755 | chr3:160565280-160565353 | | | PPM1L | PPM1L | B3GALNT1 |
| chr4 | 2261779 | 2261832 | 6.48422 | chr4:2261779-2261832 | | | MXD4 | MIR4800 | MXD4 |
| chr4 | 1.38E+08 | 1.38E+08 | 6.04767 | chr4:138242023-138242168 | | | | LINC00613 | PCDH18 |
| chr5 | 1878019 | 1878802 | 8.64563 | chr5:1878019-1878802 | | | IRX4 // IRX4 // IRX4/ IRX4 | LOC101929034 | IRX4 |
| chr5 | 1879525 | 1879651 | 6 | chr5:1879525-1879651 | | | IRX4 // IRX4 // IRX4 // IRX4 // IRX4 | LOC101929034 | IRX4 |
| chr5 | 1.35E+08 | 1.35E+08 | 5.66667 | chr5:135399139-135399178 | | CU674033 // CU678833 | TGFBI | TGFBI | VTRNA2-1 |
| chr5 | 1.73E+08 | 1.73E+08 | 5.77778 | chr5:173328196-173328338 | | | CPEB4 | CPEB4 | C5orf47 |
| chr5 | 1.81E+08 | 1.81E+08 | 6.48422 | chr5:180529265-180529344 | | | | MIR8089 | OR2V1 |
| chr6 | 1312506 | 1312962 | 9.72633 | chr6:1312506-1312962 | FOXQ1 | BC053850 | EOXQ1 | LOC285768 | FOXF2 |
| chr6 | 1313253 | 1313290 | 7.56493 | chr6:1313253-1313290 | FOXQ1 | BC053850 | FOXQ1 | LOC285768 | FOXF2 |
| chr6 | 13977052 | 13977290 | 6.48422 | chr6:13977052-13977290 | | DQ892444 // DQ895649 // DQ892438 // DQ895648 // CU688980 // AB464692 // CU688981 // AK098091 | RNF182 // RNF182 // RNF182 // RNF182 | RNF182 | CD83 |
| chr6 | 13977398 | 13977544 | 6.48422 | chr6:13977398-13977544 | | DQ892444 // DQ895649 // DQ892438 // DQ895648 // CU688980 // AB464692 // CU688981 // AK098091 | RNF182 // RNF182 // RNF182 // RNF182 | RNF182 | CD83 |

TABLE 3-continued

Mettl8 M³C RIP sequence targets

| chr | start | end | fold_enrichment | region | refgene_TSSpm1kb | all_mRNA_TSSpm1kb_ACC_ol | refgene_Symbol_ol | refgene_TSSpm1kb_Symbol_ol | refgene_TSSpm1kb_Symbol_ln | refgene_TSSpm1kb_Symbol_m |
|---|---|---|---|---|---|---|---|---|---|---|
| chr6 | 13979868 | 13979935 | 6.48422 | chr6:13979868-13979935 | | RNF182 // RNF182 | RNF182 | CD83 | | |
| chr6 | 87088153 | 87088209 | 7.65859 | chr6:87088153-87088209 | | | | SNHG5 | HTR1E | |
| chr6 | 1.31E+08 | 1.31E+08 | 7.21868 | chr6:130865577-130865641 | | | | TMEM200A | SMLR1 | |
| chr6 | 1.55E+08 | 1.55E+08 | 6.21405 | chr6:154510197-154510234 | | OPRM1 // | OPRM1 // IPCEF1 // IPCEF1 1/ IPCEF1 | IPCEF1 | | |
| chr6 | 1.67E+08 | 1.67E+08 | 8.64563 | chr6:166938931-166939022 | | | RPS6KA2 // RPS6KA2 | MIR1913 | RPS6KA2 | |
| chr7 | 6643817 | 6643889 | 5.94387 | chr7:6643817-6643889 | | | C7orf26 | C7orf26 | ZNF853 | |
| chr7 | 29920143 | 29920202 | 7.56493 | chr7:29920143-29920202 | | | | WIPF3 | SCRN1 | |
| chr7 | 77571069 | 77571106 | 6.16667 | chr7:77571069-77571106 | | | | PHTF2 | RPL13AP17 | |
| chr7 | 93807945 | 93808219 | 9.18598 | chr7:93807945-93808219 | | | WIPF3 | BET1 | COL1A2 | |
| chr7 | 93808331 | 93808694 | 7.56493 | chr7:93808331-93808694 | | | PHTF2 // PHTF2 // PHTF2 | BET1 | COL1A2 | |
| chr7 | 93808958 | 93808995 | 7.29475 | chr7:93808958-93808995 | | | | BET1 | COL1A2 | |
| chr7 | 1.01E+08 | 1.01E+08 | 6.7544 | chr7:100539443-100539499 | | | | ACHE | MUC3A | |
| chr7 | 1.01E+08 | 1.01E+08 | 5.67369 | chr7:100605680-100605723 | | | MUC3A | MUC3A | MUC12 | |
| chr7 | 1.01E+08 | 1.01E+08 | 5.52923 | chr7:100606468-100606533 | | | MUC3A | MUC3A | MUC12 | |
| chr7 | 1.03E+08 | 1.03E+08 | 8.10528 | chr7:102988402-102988677 | PSMC2 // PSMC2 | D11094// AK298821 AB075520 // AK312648 // AK298529 // BC002589 // CU678056 // AB527557 // EU446703 | PSMC2 // PSMC2 | DNAJC2 | LOC101927870 | |
| chr7 | 1.3E+08 | 1.3E+08 | 6 | chr7:129952696-129952863 | | | CPA4 // CPA4 | CPA4 | CPA5 | |
| chr8 | 74320956 | 74321304 | 8.64563 | chr8:74320956-74321304 | | | | RDH10 | STAU2-AS1 | |
| chr9 | 93952176 | 93952330 | 7.3723 | chr9:93952176-93952330 | | | | LOC100129316 | AUH | |

TABLE 3-continued

Mettl8 M³C RIP sequence targets

| chr | start | end | fold_enrichment | region | refgene_TSSpm1kb_Symbol_ol | all_mRNA_TSSpm1kb_ACC_ol | refgene_Symbol_ol | refgene_TSSpm1kb_Symbol_ol | refgene_TSSpm1kb_Symbol_ln | refgene_TSSpm1kb_Symbol_m |
|---|---|---|---|---|---|---|---|---|---|---|
| chr9 | 1.35E+08 | 1.35E+08 | 7.02457 | chr9:135087763-135087809 | | | | NTNG2 | NTNG2 | SETX |
| chr9 | 1.35E+08 | 1.35E+08 | 6.7544 | chr9:135088027-135088069 | | | | NTNG2 | NTNG2 | SETX |
| chr9 | 1.35E+08 | 1.35E+08 | 7.29475 | chr9:135090185-135090295 | | | | NTNG2 | NTNG2 | SETX |
| chr9 | 1.35E+08 | 1.35E+08 | 9.18598 | chr9:135095874-135095975 | | | | NTNG2 | NTNG2 | SETX |
| chr9 | 1.35E+08 | 1.35E+08 | 7.20318 | chr9:135098344-135098460 | | | | NTNG2 | NTNG2 | SETX |
| chr9 | 1.35E+08 | 1.35E+08 | 5.66667 | chr9:135106740-135106811 | | | | NTNG2 | NTNG2 | SETX |
| chrX | 41555324 | 41555743 | 6.21405 | chrx:4155324-4155743 | | | | | LOC389906 | LOC10192820 1 |
| chrX | 41556122 | 41556211 | 7.56493 | chrx:4156122-4156211 | | | | | LOC389906 | LOC10192820 1 |
| chrX | 48458703 | 48458934 | 5.83333 | chrx:48458703-48458934 | | AK301186 // BC002507 | WDR13 // WDR13 // WDR13 | | WDR13 | WAS |
| chrX | 48466249 | 48466321 | 6.48422 | chrx:48466249-48466321 | | | | | WDR13 | WAS |
| chrX | 48467009 | 48467057 | 8.37545 | chrx:48467009-48467057 | | | | | WDR13 | WAS |
| chrX | 1.2E+08 | 1.2E+08 | 4.33333 | chrx:119841155-119841217 | | | | C1GALT1C1 | C1GALT1C1 | CT47B1 |

Example 3 Activation of the ATM-p53 Pathway by Inhibiting Mettl8

Figure 7B:
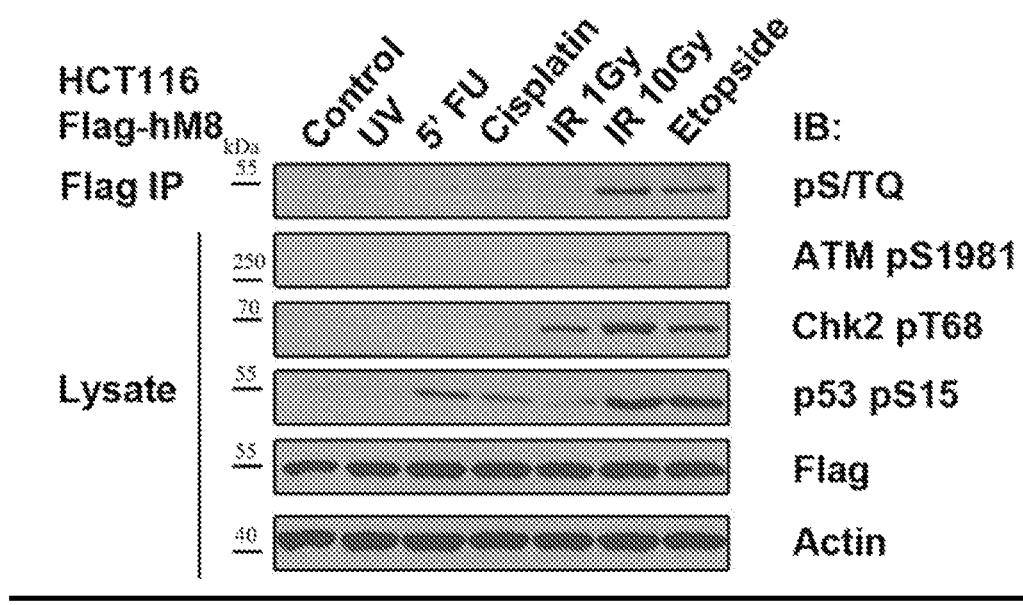
FIG. 7B shows HCT116 cell lysates immunoblotted by anti-Flag, Actin, ATM pS1981, Chk2 pT68 and p53 pS15 antibodies.

Since both ATM and p53 are tumor suppressors in response to DNA damage, inventors further explored the function of Mettl8 in DNA damage. The sketch of human Mettl8 protein domain structures shows the SANT, SAM and NRB motifs, and pSQ site (FIG. 7A). HCT116 stable cells overexpressed with Flag human Mettl8 protein were treated with various DNA damage agents (UV 100 J/m$^2$ dose, recovered for 6h; 25 µM 5'fluorouracil (5' FU) for 6h; 30 µg/ml cisplatin for 6h, gamma irradiation at 1Gy or 10Gy, recovered for 1 h; 10 µM etoposide for 6h). Equal amount of lysates were subject to Flag immunoprecipitation ("IP") with M-2 beads and washed extensively before being resolved on SDS-PAGE and followed by immunoblotting with an phosphorylation-specific antibody against pS/TQ motif (Cell signaling) and a Flag antibodu. The lysates were immunoblotted by anti-Flag, Actin, ATM pS1981, Chk2 pT68 and p53 p515 antibodies. The result in FIG. 7B is representative of three independent repeats, which show that gamma irradiation and etoposide promoted phosphorylation at the pS/TQ motif on Mettl8.

Figure 7C:
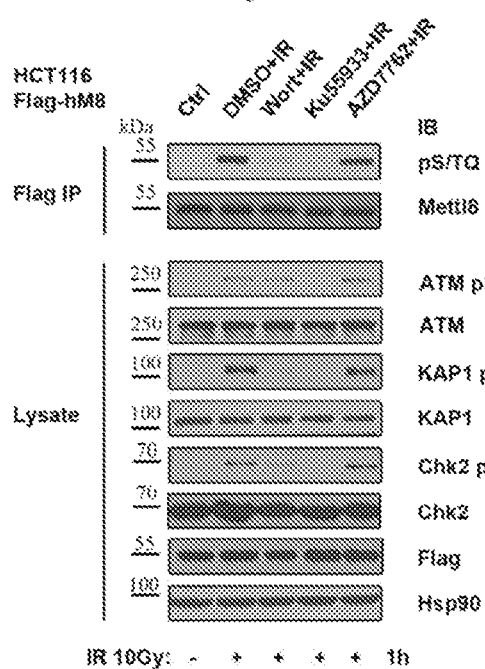
FIG. 7C shows phosphorylation at the pS/TQ motif when HCT116 cells stably overexpressing Flag-Mettl8 were pretreated with DMSO and AZD7762 and then irradiated.

Similar phosphorylation was observed at the pS/TQ motif when HCT116 cells stably overexpressing Flag-Mettl8 were pretreated with DMSO and 0.5 µM AZD7762 (Chk1/2 inhibitor) for 1 hour, and were then irradiated at 10 Gy for another 1 (FIG. 7C). Wortmannin (PIKK inhibitor) and Ku55933 (ATM inhibitor) reduced the phosphorylation. In this experiment, equal amount of lysate was immunopurified with M2 beads and probed for pS/TQ antibody, the lysate was checked for antibodies indicated in FIG. 7C. The results indicate that pSQ motif can be phosphorylated by PIKK and ATM.

Figure 7D:
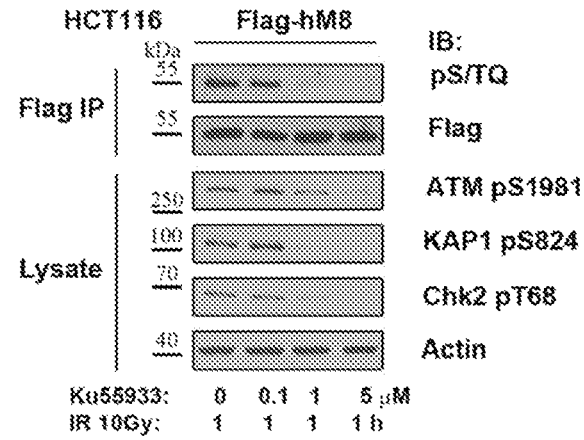
FIG. 7D shows dose responses on Mettl8 phosphorylation by IR.

As Ku55933 at 10 µM could inhibit DNAPKcs activity (IC$_{50}$ about 5 µM) and ATM, but not ATR, inventors then tested dose responses on Mettl8 phosphorylation by IR, as shown in FIG. 7D. 1 µM Ku55933 was sufficient to prevent the phosphorylation of Mettl8, suggesting that ATM is the kinase that phosphorylates Mettl8. Here, HCT116 stable cell with Flag-Mettl8 was pretreated with DMSO or dependent dose of Ku55933 at 0.1, 1 or 5 µM concentration for 1 hour, then they were irradiated at 10 Gy and harvested 1 h later. Equal amounts of lysate were immunopurified with M2 beads and probed for pS/TQ antibody, the lysate was checked for antibodies indicated.

Figure 7E:
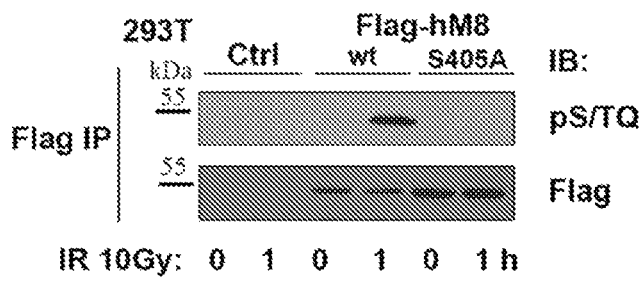
FIG. 7E shows pS/TQ phosphorylation was detected on wild type Mettl8 upon irradiation, but not on S405A mutant.

To further verify whether Ser 405 on Mettl8 is the pS/TQ motif, inventors mutated Ser 405 to alanine. As shown in FIG. 7E, pS/TQ phosphorylation was detected on wild type Mettl8 upon irradiation, but not on S405A mutant, indicating that Ser-405 is the sole target of ATM. Here, 293T cells transfected with wt Flag-Mettl8 and S405A mutant were irradiated at 10Gy and harvested 1 hour later, together with untransfected cells. Equal amount of lysate was subject to Flag immunoprecipitation and probed for pS/TQ, Flag antibodies.

Figure 7F:
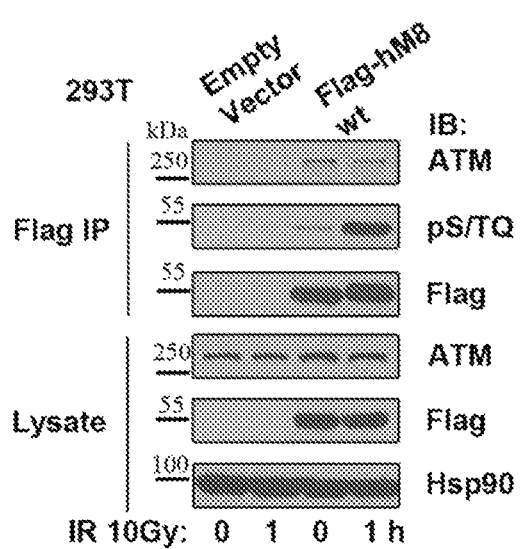
FIG. 7F shows endogenous ATM found in immunoprecipitation of Flag-Mettl8, either in the resting state, or after irradiation with 10Gy.
Figure 7G:
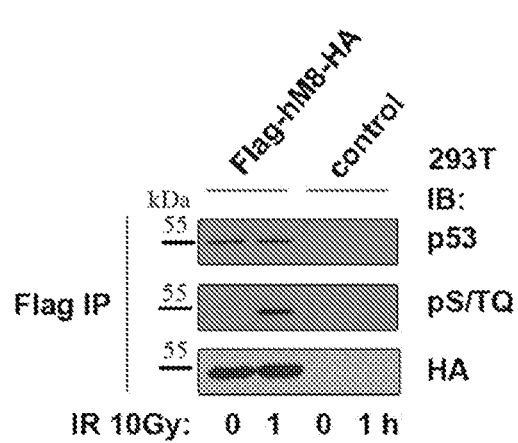
FIG. 7G shows interactions independent of irradiation-induced phosphorylation of pS/TQ motif that were observed between Mettl8 and endogenous p53.

Endogenous ATM was found in immunoprecipitation of Flag-Mettl8, either in the resting state, or after irradiation with 10Gy (FIG. 7F), suggesting that the interaction is independent of the status of Mettl8 pSQ motif. In this experiment, Flag-Mettl8 was overexpressed in 293T cell and irradiated at 10Gy for 1 h. IP product with Flag antibody was probed for endogenous ATM, pS/TQ and Flag antibodies, together with lysate probed with ATM, Flag and Hsp90 antibodies. This interaction was not dependent on RNA or DNA, as RNase A or DNase I treatment did not affect the interaction significantly (data not shown). A similar interaction, independent of irradiation-induced phosphorylation of pS/TQ motif, was observed between Mettl8 and endogenous p53 (FIG. 7G). In this experiment, Flag-Mettl8-HA was over-expressed in 293T and immunopurified by M2 beads after irradiation for various time, and subject to immunoblotting with p53, HA and pS/TQ antibodies.

Figure 7H:
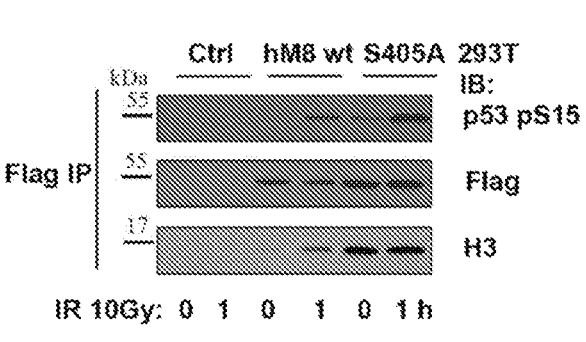
FIG. 7H shows either wild type or Ser405Ala mutant was detected in Mettl8 immunoprecipitates.
Figure 7I:
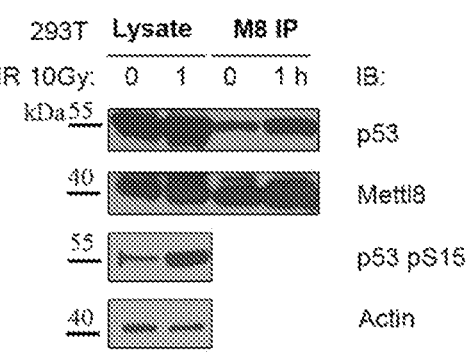
FIG. 7I shows 293T IP with endogenous Mettl8.

Moreover, phospho-S15 p53 was also found in Flag IP of Mettl8. Either wild type or Ser405Ala mutant (FIG. 7H) or histone 3 was detected in Mettl8 immunoprecipitates, along with other core histones (data not shown), suggesting that at least a portion of Mettl8 protein pool may interact with chromatin. This result is confirmed in 293T IP with endogenous Mettl8 (FIG. 7I), suggesting a constitutive complex between p53, Mettl8 and ATM.

Figure 7J:
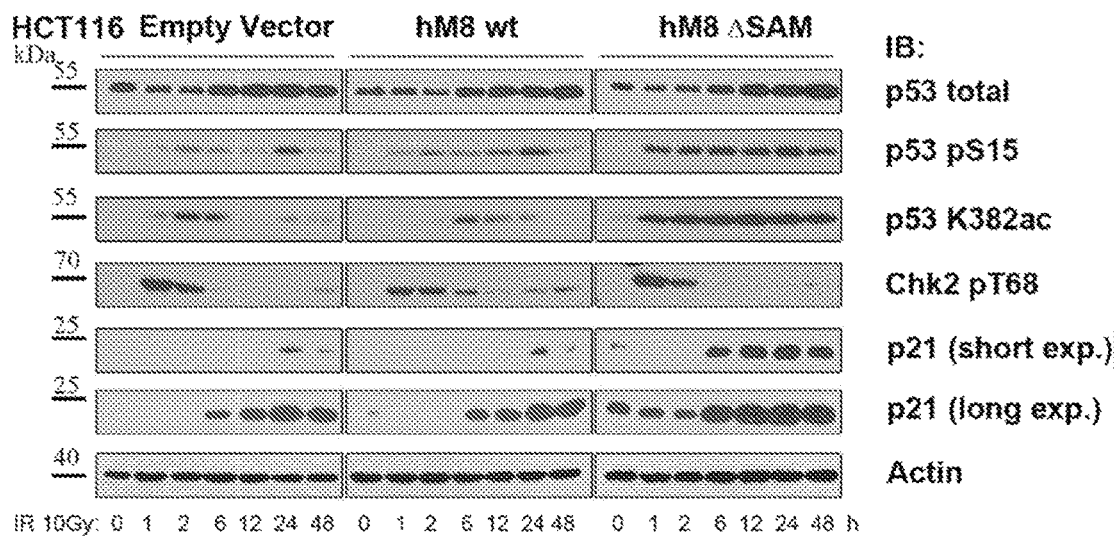
FIG. 7J shows p53 phosphorylation at Ser 15 in response to IR was enhanced in cells expressing a Mettl8 SAM mutant compared to the wild type and empty vector control.

As both ATM and p53 are tumor suppressors in response to DNA damage, inventors further explored the function of Mettl8 in DNA damage. In a time-course study (FIG. 7J), p53 phosphorylation at Ser 15 in response to IR was enhanced in cells expressing a Mettl8 SAM mutant compared to the wild type and empty vector control. Acetylation at Lys 382 on p53 was also increased, while total induced p53 expression were at similar levels in both mutant and wild type. Chk2 phosphorylation by ATM was altered in mutant cells, showing a shorter duration than wild type and at a higher intensity (FIG. 7J). This change in Chk2 activation is consistent with the changes in total p53 level in mutant Mettl8 cells, conforming the function of Chk2 in stabilizing p53 by phosphorylating Ser20 of p53 and disrupting MDM2-p53 binding. Strikingly, p21, a target of p53, was induced significantly in Mettl8 mutant cells, either at basal level or after irradiation (FIG. 7J). These observations indicate that Mettl8 may affect the activation of p53 target genes.

Figure 7K:
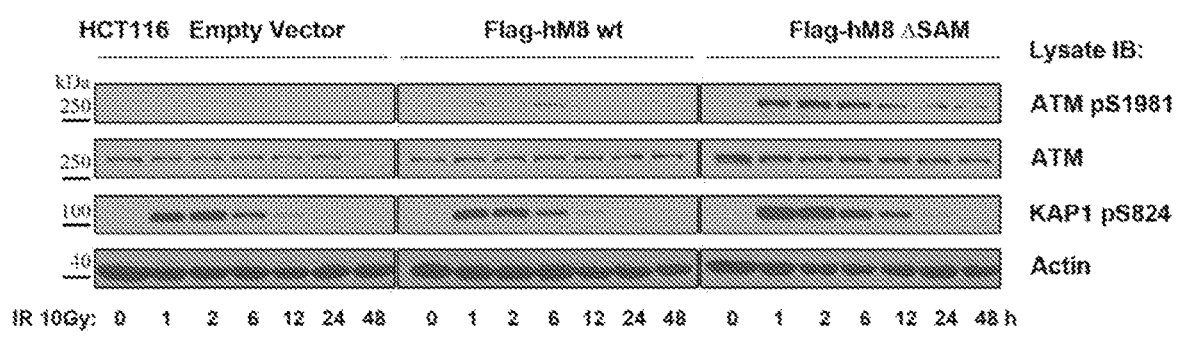
FIG. 7K shows Ser1981 phosphorylation was upregulated in mutant cells compared to wild type Mettl8 cells.

Since p53 Ser15 is a target site of ATM, inventors also examined the autophosphorylation at Ser1981 for ATM activation (24). Ser1981 phosphorylation was upregulated in mutant cells compared to wild type Mettl8 cells (FIG. 7K). Phosphorylation of heterochromatin factor KAP1, another substrate of ATM, was elevated in mutant cells. Interestingly, the level of ATM protein was also elevated in the mutant cells, consistent with upregulation of auto-phosphorylation.

Figure 7L:
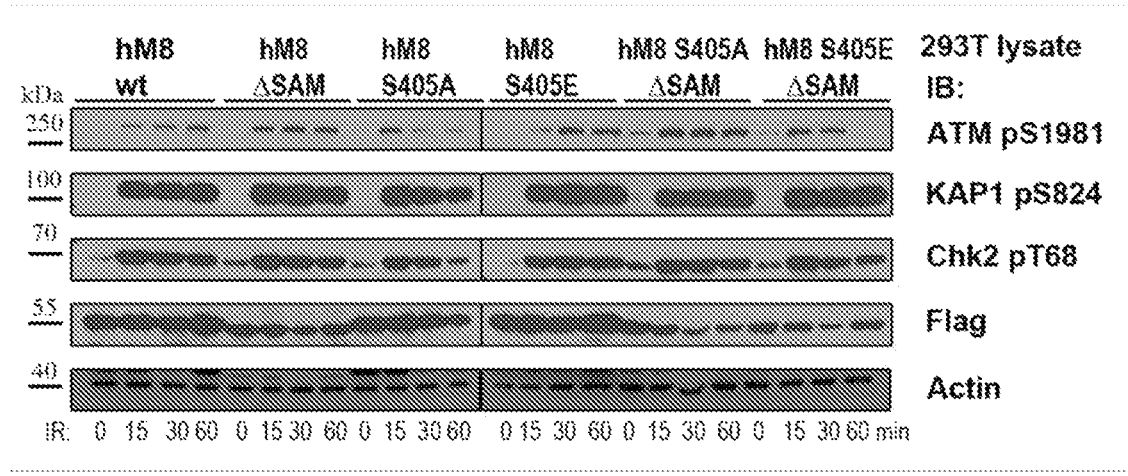
FIG. 7L shows S405A mutant showed enhanced ATM phosphorylation at 15 min after IR, which quickly diminished between 30 to 60 min after IR.

To investigate if pS/TQ motif is required for Mettl8 function to activate ATM kinase, Mettl8 wild type, SAM mutant, S405A or S405E and double mutant with S405 and SAM domain were examined in 293T cells (FIG. 7L). SAM mutant showed enhanced ATM activation compared to wild type, which is consistent with the results obtained in HCT116 cells. S405A mutant showed enhanced ATM phosphorylation at 15 min after IR, but quickly diminished between 30 to 60 min after IR (FIG. 7L). S405E, the phosphor-mimic mutant, showed otherwise. Although the initiation of ATM activation was delayed, S405A and SAM double mutant cells showed greater and longer activation than each single mutant. S405E and SAM double mutant showed shorter ATM activation, which differed from each single mutant phenotype. Without being bound by a theory, these results indicate ATM activation could be affected by the pS/TQ motif on Mettl8 in a distinct manner.

Figure 7M:
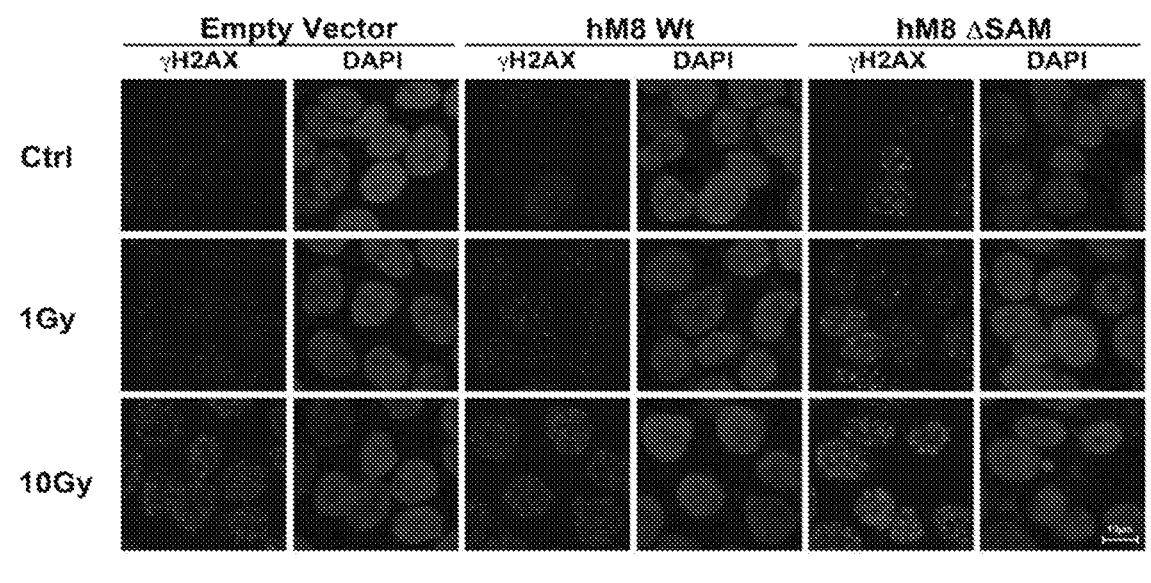
FIG. 7M shows H2AX, the marker for DNA damage, was also substantially enhanced in SAM mutant cells compared to empty vector and wild type Mettl8.

H2AX, the marker for DNA damage, was also substantially enhanced in SAM mutant cells compared to empty vector and wild type Mettl8 (FIG. 7M), in relation to the intensity of staining with a γH2AX antibody. Brighter and more foci of γH2AX were observed in mutant cells, even without irradiation, indicating endogenous DNA damage. In this experiment, HCT116 stable clone with empty vector, wt or ΔSAM Mettl8 were irradiated at 1 or 10Gy and left in recovery for 1 h before standard immunostaining procedure with γH2Ax antibody, counter stain with DAPI. Image was presented after Z-stack processing.

The above results from cell lines were further supported by data from primary human skin fibroblasts which were transduced with lentiviral vector expressing GFP control, wildtype Mettl8 or SAM mutant in T2A EGFP vectors. As shown in FIG. 5N, even with an efficient viral infect, the level of SAM mutant protein could be barely detected, but phosphorylations on p53, KAP1, Chk2 were enhanced with overexpressed SAM mutant protein. ATM phosphorylation and p53 total protein level were also elevated significantly. In this experiment, normal human skin fibroblast cells were transduced with lentivirus expressing empty vector, wild-type Flag-Mettl8 or SAM mutant. After selection with puromycin for 3d, they were irradiated at 10Gy and harvested at indicated time points. Equal amount of lysates were subject to immunoblotting with various antibodies listed.

Figure 7P:
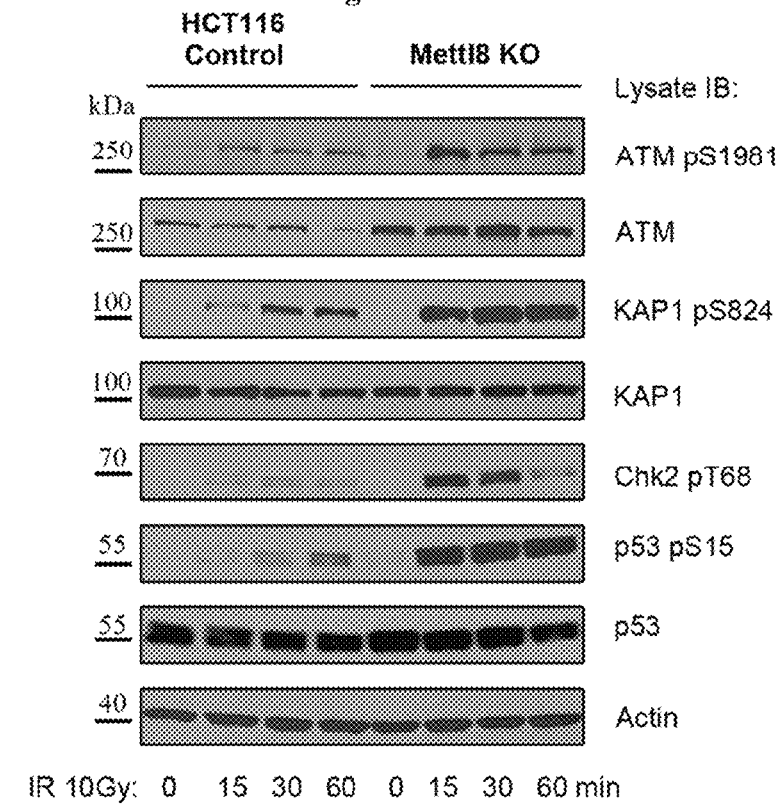
FIG. 7P shows downregulation of Mettle8 by knockout enhanced ATM phosphorylation at Ser1981.

To validate the results in endogenous conditions, endogenous Mettle8 gene was either knocked down with shRNA or knocked down with CRISPR. Downregulation of Mettle8, either by knockdown (FIG. 7O) or knockout (FIG. 7P), enhanced ATM phosphorylation at Ser1981. The enhancement was observed as early as 15 min after irradiation in Mettl8 knockout cells as compared to the control, along with significant elevation of downstream ATM substrates phosphorylation, such as Chk2, KAP1, and p53 (FIG. 7P). The level of ATM total protein was also increased in the knockout cells as found in mutant cells (FIG. 7P). Similar observations were recorded in two other clones of Mettl8 knockout, using either HCT116 or 293T cells (data not shown).

Figure 7Q:
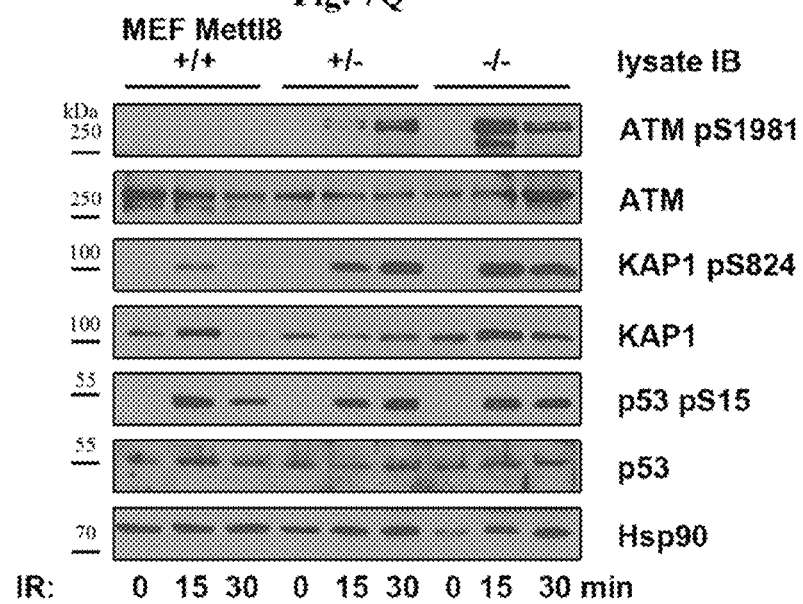
FIG. 7Q shows strong ATM phosphorylation signals observed in heterozygous MEF and knockout MEF, and KAP1 phosphorylation was also elevated significantly in knockout MEF and heterozygous MEF.

Inventors also generated Mettl8 knockout mouse models using CRISPR-mediated mutagenesis technology. Three gRNAs were co-injected along with Cas9 mRNA into mouse embryos respectively, in which the deletion mutant was screened. A deletion mutant that caused frame shift and premature termination was selected. Mouse embryonic fibroblast (MEF) cells were isolated from the E13.5 day sibling embryos which resulted from the mating of heterozygous Mettl8. They were then irradiated with 10Gy, similar treatment given to human cells previously, as shown in FIG. 7N. Due to limited sensitivity of mouse ATM phosphorylation antibody at Serine 1981, barely any signal was detected in wild type MEF cells treated with irradiation, while strong ATM phosphorylation signals were observed in heterozygous MEF (FIG. 7Q). Knockout MEF showed the strongest signal. KAP1 phosphorylation was also elevated significantly in knockout MEF and heterozygous MEF than in wild type MEF (FIG. 7Q). p53 phosphorylation was slightly stronger at 15 min after IR in knockout cells compared to wild type. These findings further support that Mettl8 regulates the ATM-p53 pathway.

Figure 7R:
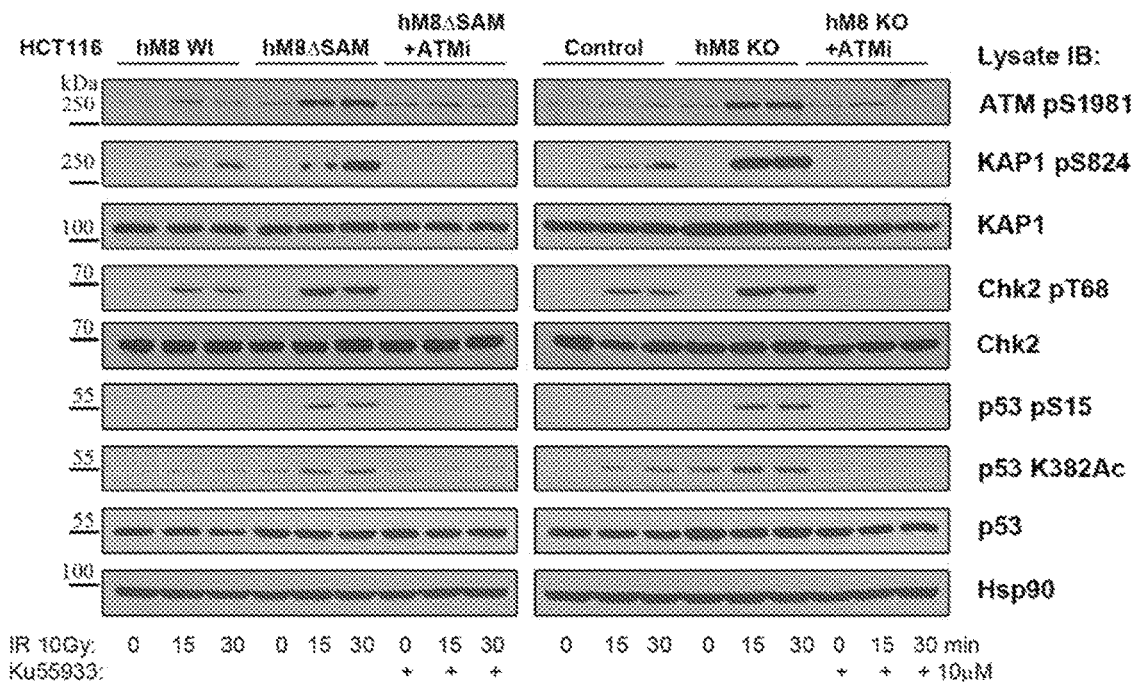

In addition, the mutant or knockout cells were pre-treated with specific ATM inhibitor Ku55933 was used to pretreat before irradiation. As shown in FIG. 7R, pre-treatment with ATM inhibitor either reverted or eliminated the hyper activation of ATM, KAP1, Chk2, p53 by irradiation, indicating in these irradiated cells, ATM activation is controlled by Mettl8.

To explore the binding partners of Mettl8, Flag immunoprecipitate followed by LC-MS analysis was performed. As shown in FIG. 8A, multiple protein bands were detected on Flag peptide elution from Flag-Mettl8 immunoprecipitation but not on empty vector controls (lanes 3 and 4 compared to lanes 1 and 2), irradiation treatment made little difference to the band pattern. Gel slices were prepared from the lanes and subject to in-gel digestion followed by LC-MS analysis. The proteins were listed in FIG. 8B according to peptide number with 95% confidence.

Among them, some RNA splicing factors and DNA damage factors were found. KAP1 (TRIM28), H2AX and many other histones (not shown here) were detected. TOP1 drew our attention as TOP1 has been suggested to play a role in ATM activation, and formed genetic network with ATM, RNaseH1. It is also a key negative regulator of R-loop formation through its topological enzymatic domain. The binding was validated in immunoprecipitation with Flag-Mettl8 from HCT116 stable cell, interestingly, endogenous TOP1 was only found in untreated cells but not in irradiated ones, consistent with LC-MS data (FIG. 8C).

Figure 8D:
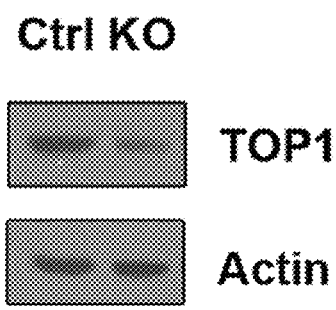
Figure 8D:
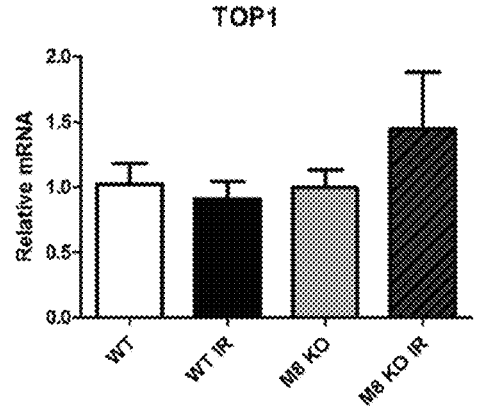
Figure 8E:
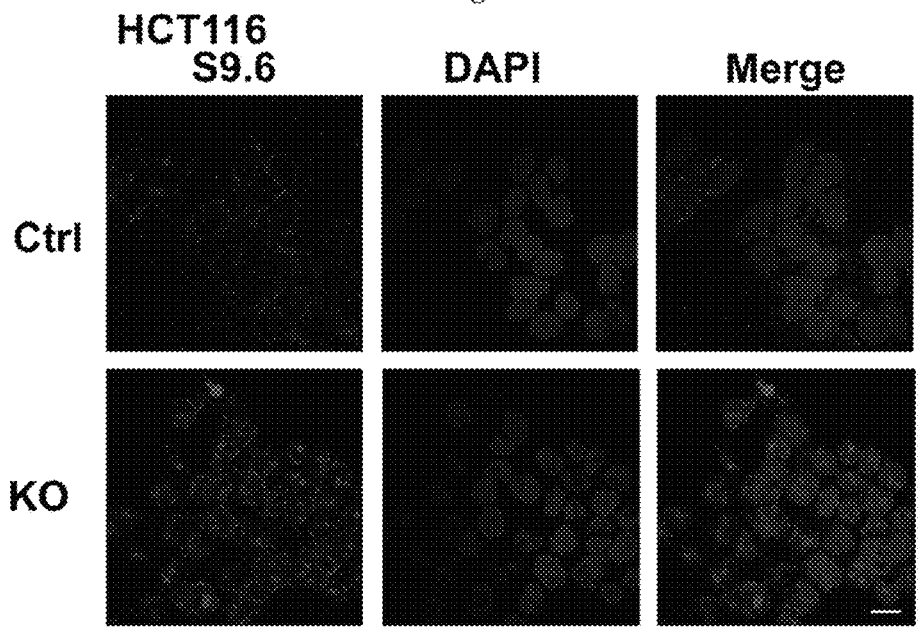
Figure 8F:
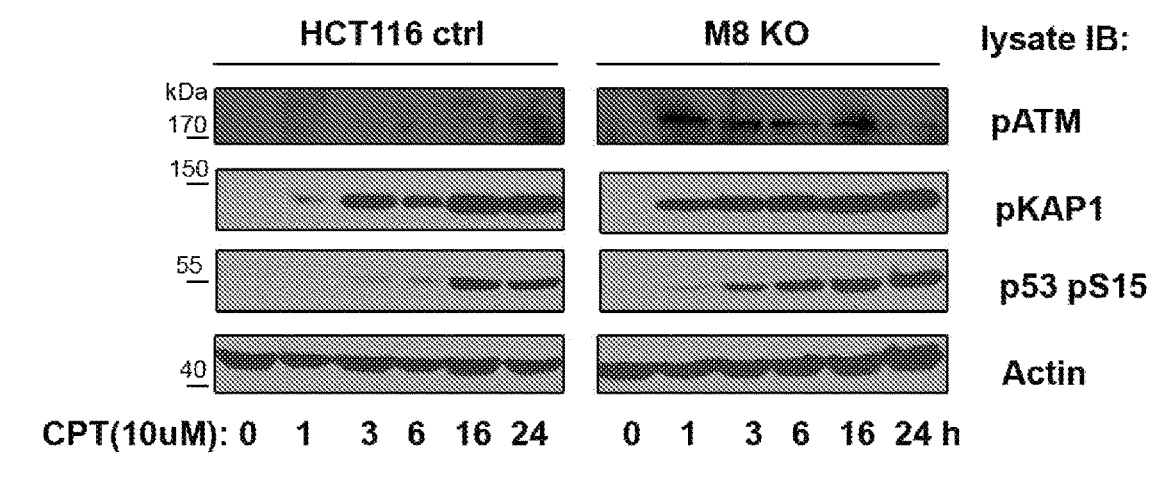

While the mRNA level of TOP1 remained unchanged (data not shown), the protein level of TOP1 was reduced in Mettl8 knockout cells (FIG. 8D). Because R loop has been shown to be involved with ATM signaling as well as p53 activation, the expression of R loop level was examined using immunostaining with the widely-accepted S9.6 monoclonal antibody. Mettl8 knockout HCT116 cells showed stronger R loop staining compared to wild type cells (FIG. 8E). Similar results were obtained from HeLa cells with Mettl8 (data not shown), consistent with the lower level of TOP1 found in Mettl8 knockout cells.

HCT116 WT and METTL8 KO cells were treated with 10 μM camptothecin for 0 h, 1 hr, 3 hr, 6 hr, 16 hr, and 24 hr. Equal amount of lysates were resolved on SDS-PAGE followed by immunoblotting with antibodies. As shown in FIG. 8F, TOP1 inhibitor camptothecin treatment caused hyperactivation of ATM in terms of intensity and speed in Mettl8 knockout cells to a greater extent. Because activation of ATM leads to downstream function in tumor suppression (FIG. 1), the results suggest that loss of Mettl8 sensitized the tumor cell for TOP1 inhibition.

Example 4 Mettl8 Regulates Cell Growth

As ATM is essential for cell checkpoint, the cell cycle profiles were studies in this experiment. The plasmid containing the cDNA of human Mettle8 SAM deletion mutant was constructed by PCR based mutagenesis method to delete the specific nucleotide sequence in the SAM domain as shown in FIG. 7A. After the plasmid was transfected into HCT116 wildtype cells, stable colonies of cell containing the plasmid were selected, which were called Mettl8 ΔSAM cells. The HCT116 cells containing an empty vector or wildtype Mettl8 plasmid were used as control cell lines, as shown in FIGS. 7J and 7K. The Mettle8 ΔSAM variant cDNA was also transduced into human skin fibroblast as shown in FIG. 7N by a lentivirus based method. These HCT116 stable cells were examined in cell cycle analysis (FIG. 9A) and soft agar colony assay (FIG. 9B). Recombinant purified protein of GST-Mettl8 wt and SAM mutant was tested in SAM binding assay (FIG. 6A), which shows that Mettl8 ΔSAM variant protein lost the ability to bind the SAM donor molecule which is the first and essential step for methyl transferring reaction.

In addition, HCT116 stable cells with Mettl8 variant were fixed with 70% ethanol and stained with pI followed by cell cycle profiling on FACS and data were analysed with FlowJo software. As shown in FIG. 9A, wild-type Mettl8 cells showed similar profiles as the empty vector cells under un-stressed conditions, while ΔSAM mutant cells showed more accumulation of G2/M populations. A significantly higher percentage of G2/M cells were in both wild type and ΔSAM mutant cells when subjected to irradiation.

Therefore, Mettl8 ΔSAM variant inhibited the function of Mettl8, and induces ATM/p53 activation and cell growth retardation/arrest.

Soft agar colony assays also showed much reduced colony numbers in mutant Mettl8 cells as compared to the empty vector (FIG. 9B). In the soft agar colony assay, HCT116 cells with Mettl8 wt or ΔSAM were seeded at 500 cells/well in 6-well plate in triplicate and after 2-week colonies grown up in soft agar was shown. Colonies with more than 50 cells were counted with Quantity One software. A similar result was observed in a cell growth assay, in HCT116 cells with scramble snRNA, empty vector or Mettl8 shRNA2 were seeded into a 6-well plate with 500 cells/well in triplicate manner. 7 days later, cells were fixed and stained with crystal violet. The images of plates were collected with ImageLab software. Based on the cell growth assay in FIG. 9C, knockdown of Mettl8 in HCT116 cells significantly reduced the colony formation.

Figure 9D:
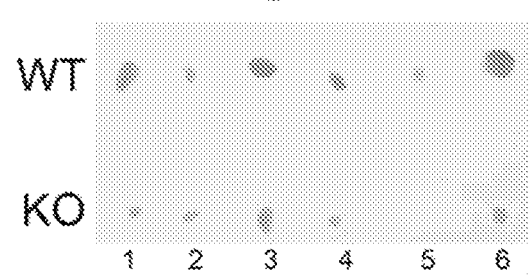
Figure 9D:
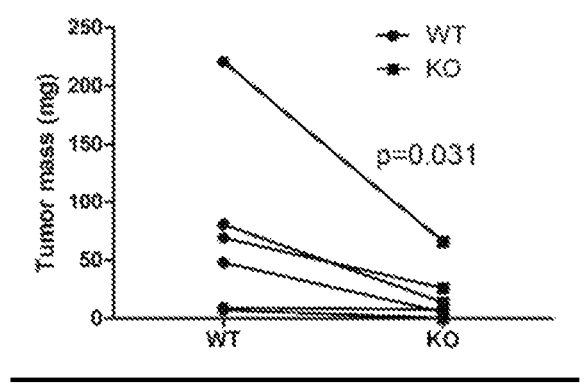

In a xenograph assay, $1 \times 10^5$ HCT116 control and Mettl8 knockout cells were mixed with Matrigel and injected subcutaneously into the left or right flank on the back of 6-week old female NOD-SCID mice. After 4 weeks, tumor tissue was dissected and photographed. Mettl8 knockout HCT116 showed lower tumor growth potential than do control cells (FIG. 9D). Without being bound by a theory, these results suggest the role of Mettl8 in checkpoint responses and growth control.

Example 5 Inhibition of Mettl8 Renders the Cell Sensitive to Cisplatin Treatment The previous experiment showed that cisplatin treatment significantly reduced Mettl8 protein level (FIG. 4). To further study the relationship between cisplatin and Mettl8, MTS and colony survival assays were performed. In the MTS assay, HCT116 wildtype and Mettl8 knockout cells were seed in 96 well at 1000 cell/well density and treated with different dose of cisplatin. In the colony survival assay, 500 cells per well of HCT116 control and Mettl8 knockout cells were seeded into 6-well plates in triplicate and subjected to different dosage of cisplatin treatment for 2 h.

Figure 10A:
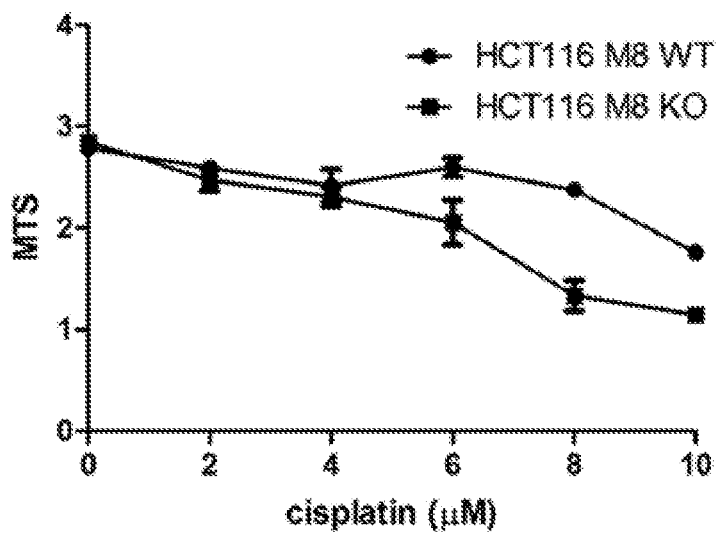
FIGS. 10A-10B show that tumor cells are more sensitive to cisplatin treatment by inhibiting Mettl8 expression.
Figure 10B:
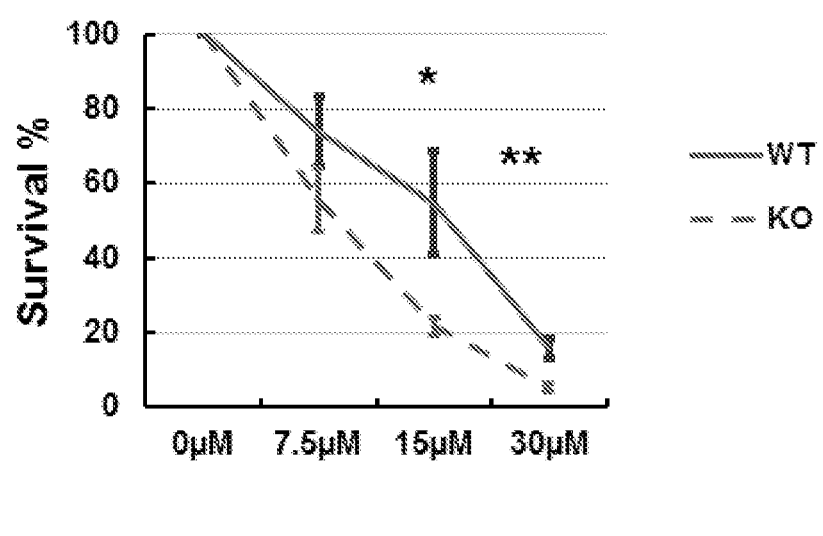

Cells were grown in fresh media for a week and the survival cell colonies were fixed and stained with crystal violet. Colonies with more than 50 cells were counted. The result was presented in ±SEM of percentage of colonies survived compared to untreated samples. Both the MTS assay (FIG. 10A) and the colony survival assay (FIG. 10B) show that Mettl8 knockout cells were more sensitive to cisplatin treatment. This effect is dependent on p53 for cisplatin induced apoptosis (data not shown). This difference in sensitivity could be exploited in clinical context that patients with functional p53 and low Mettl8 tumor may benefit more from cisplatin treatment instead of radiotherapy.

Example 6 Modulation of the Survival Rates in p53 Null or Mutant Patients Through Inhibiting Mettl8

Figure 11A:
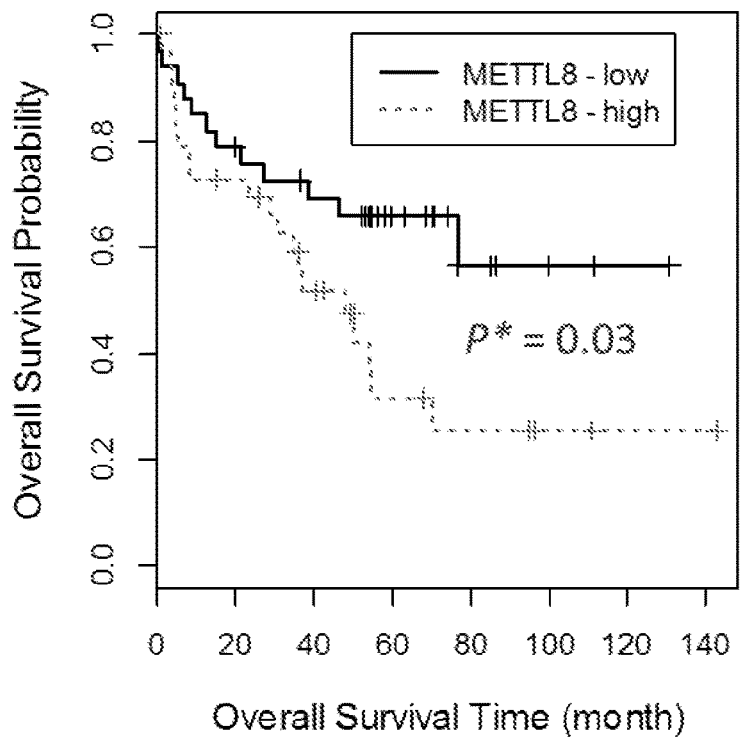
Figure 11A:
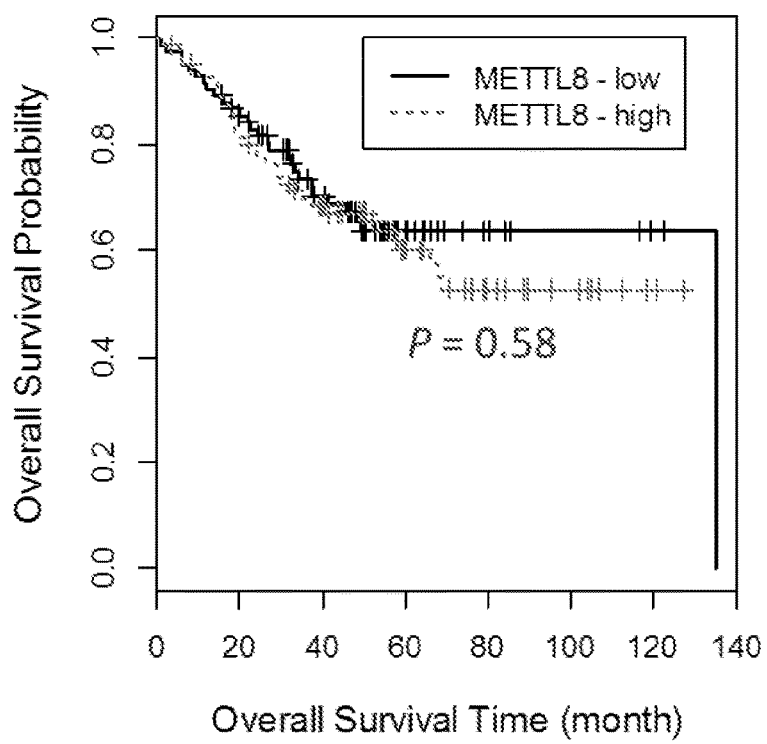

In analyzing published clinical datasets of human colorectal cancer patients (GSE17536&GSE17537), inventors found the bimodal distribution of p53 expression levels across all 232 patients. Patients enrolled in published dataset (GSE17538) could be stratified into two cohorts based on p53 mRNA level: low (n=67) and high (n=165). In those patients with low p53 expression, Mettl8 low level group (upper panel) showed a better survival rate compared to group with high level of Mettl8(lower panel) (FIG. 11A) (FIG. 11A). Although p53 is an important tumor suppressor, its level alone in this cohort of patients makes little difference in terms of overall survival probability (FIG. 11B). Mettl8 expression was used as the prognosis marker and survival analysis was performed using the Kaplan-Meier estimator for each group and the whole cohort. Interestingly, patients with low p53 expression showed significant survival difference for the Mettl8 low/high clusters (FIG. 11A). While low Mettl8 expression displayed a higher survival rate, higher Mettl8 led to increased fatality (FIG. 11A), indicating that Mettl8 plays a critical role in low-p53, oncogenesis-induced fatality.

Figure 11C:
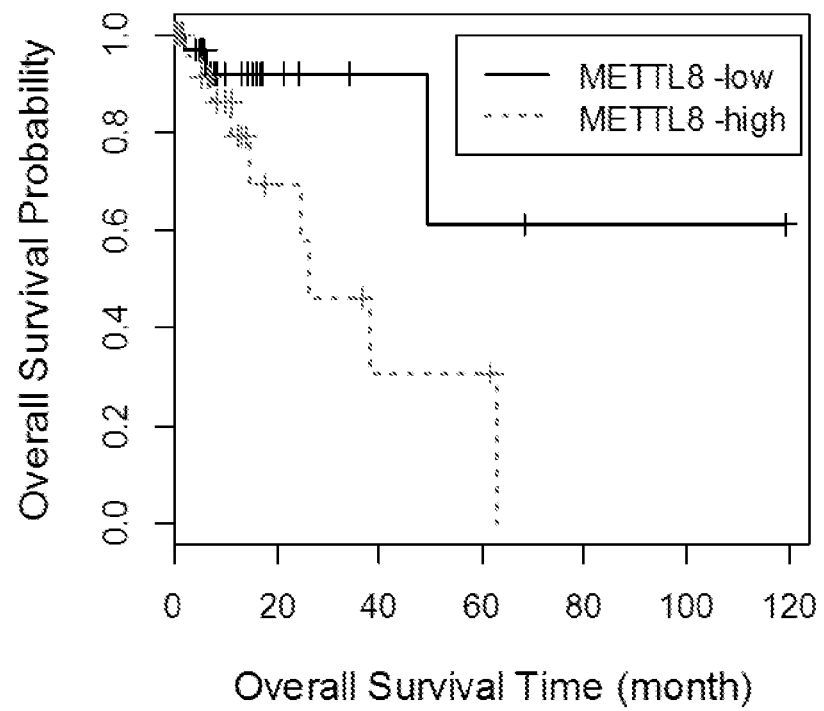
Figure 11C:
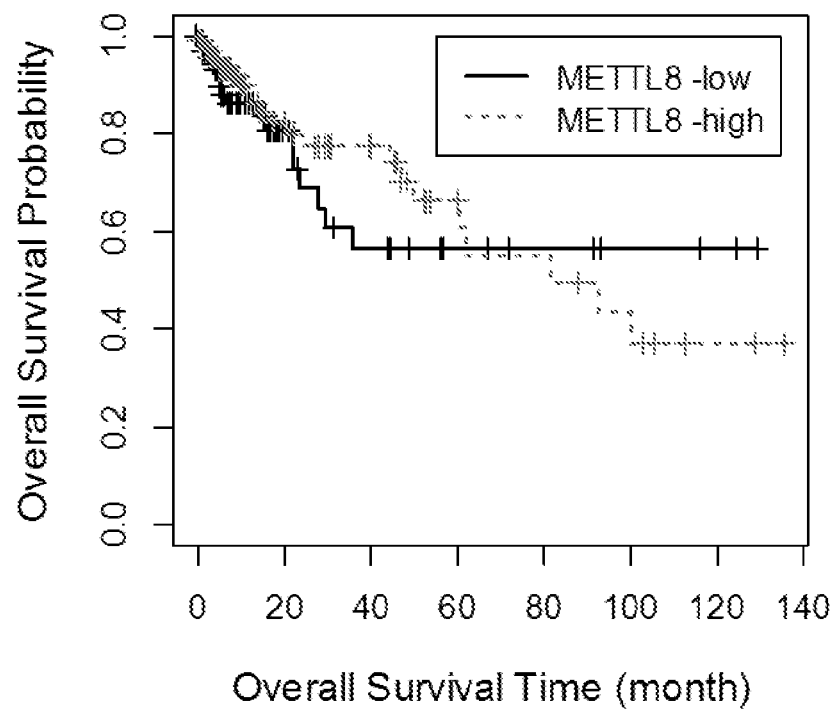

As p53 status in those patients was not clear whether it's mutated, inventors further analysed the TCGA RNA seq dataset of colon cancer. Patients from TCGA colon cancer RNA seq dataset (https://tcga-data.nci.nih.gov/tcga/) were stratified according to Trp53 and Mettl8 gene expression level and survival rate was monitored in two cohorts of patients based on p53 mRNA level: low (n=95) and high (n=328). In p53 low or deteriorate mutation cohort, Mettl8-low group showed better survival rate than Mettl8-high group (FIG. 11C). Consistently, TP53 or Mettl8 level alone could not be the defining marker for better survival rate (FIG. 11D). Among the 58 TP53-low plus 37 patients with p53 deteriorative loss-of-function mutations, those with low Mettl8 level displayed a significantly higher survival rate than Mettl8-high ones. In contrast, there was no difference between Mettl8 high or low patients in those TP53-high group (data not shown). These results suggested the possibility of Mettl8 being the decisive factor in oncogenesis when p53 is relatively low or mutated.

Figure 11E:
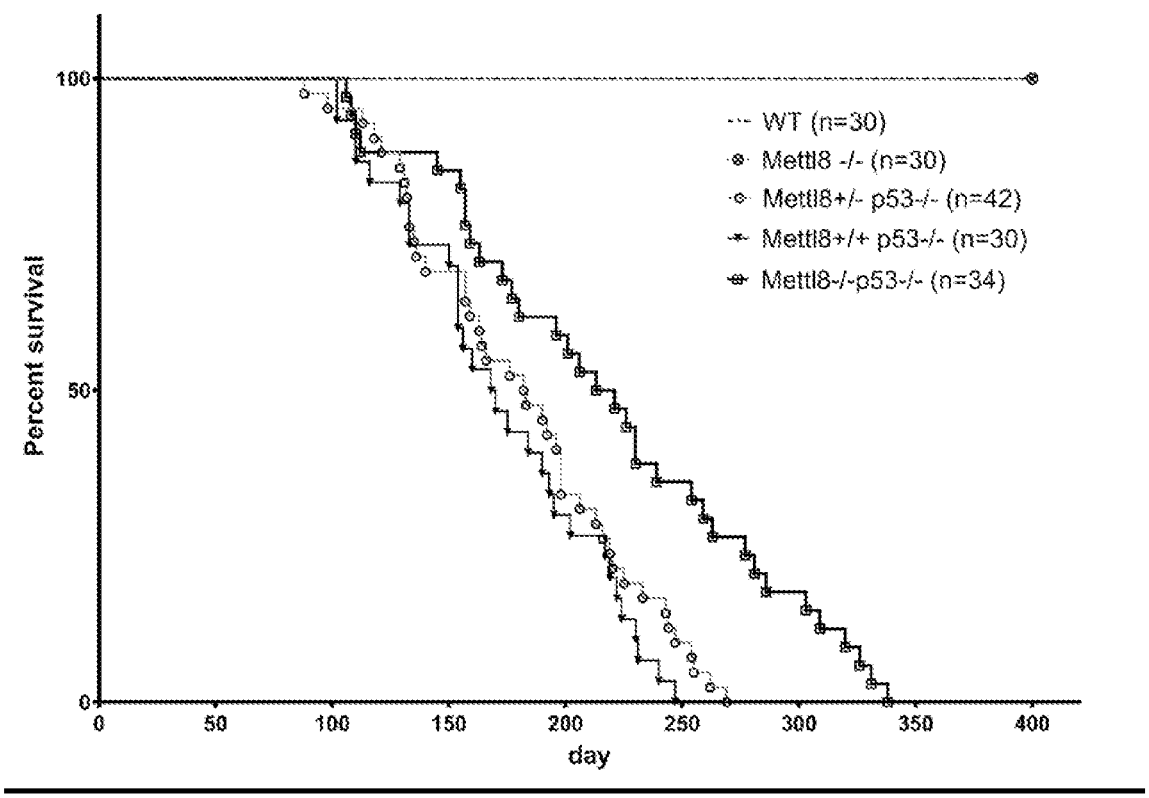

Inventors further examined possible outcomes of p53 knock out mice in the presence and absence of Mettl8. Different genotypes of mice were maintained and observed for tumor incidence and survival period up to 1 year. Survival curve was prepared with graphpad software. As shown in FIG. 11E, there was approximately 70% fatality in p53 single knockout mice at the age of 8 months. Surprisingly, Mettl8-/-/p53-/- mice showed a significantly reduced fatality rate of approximate 28% (p=0.0074) and survived well within the 300-day time frame. Mettl8+/-/ p53-/- mice also showed reduced fatality (49%). Genes with differential expression levels in MEF from different genetic backgrounds were plotted in heat-map (FIG. 11F). The results were from RNA seq data with E13.5 MEF. The detailed information was included in Table 4. Analysis of tumor spectrum revealed that Mettl8/p53 double knockout mice share similar patterns to that of p53 knockout mice, with majority being lymphoma. The fact that the p53 and Mettl8 double knock out mice could rescue p53 deficiency-caused susceptibility to tumor formation and fatality substantiates the conclusion that Mettl8 is functionally connected with p53.

TABLE 4

Genes with differential expression levels from different mouse MEF, which are grouped according to the different pattern as shown in each tab.

| Gene/nc RNA | Length | RNA-seq | | | | | | Microarray | | | | | |
|---|---|---|---|---|---|---|---|---|---|---|---|---|---|
| | | WT | M8 knockout | TP53 knockout | D knockout | fd M8 knockout/WT | fd D knockout/TP53 knockout | WT | M8 knockout | TP53 knockout | D knockout | fd M8 knockout/WT | fd D knockout/TP53 knockout |
| Enolb | 3411 | 7512.576 | 136.275 | 226.5988 | 8061 | 5.461041 | 5.152746761 | 12.33093 | 9.129252 | 8.747511 | 12.12671 | −3.201681 | 3.379203 |
| 2610305D13Rik | 2561 | 1304.243 | 144.7922 | 160.097 | 1169 | −3.171156 | 2.868257012 | | | | | | |
| Msx1 | 1931 | 641.8066 | 163.9559 | 91.13212 | 458 | −1.968831 | 2.245999434 | 10.99184 | 9.064301 | 8.346908 | 10.46656 | −1.927538 | 2.119655 |
| Rgs1 | 1330 | 489.3776 | 141.5983 | 70.19636 | 269 | −1.789144 | 1.938137959 | 8.650328 | 7.276915 | 6.704761 | 7.873389 | −1.373413 | 1.168628 |
| Mir218-1 | 110 | 24.06775 | 7.452541 | 2.46303 | 13 | −1.691297 | 1.2410081 | 5.745759 | 5.822354 | 5.568834 | 4.515319 | 0.0765953 | −1.0535153 |
| Lhx 8 | 1977 | 311.7346 | 77.71935 | 70.19636 | 222 | −1.657006 | 1.167246806 | 11.35472 | 9.083404 | 8.98756 | 10.65749 | −2.271312 | 1.669926 |
| Mir99a | 65 | 16.04517 | 5.323243 | 1.231515 | 13 | −1.591761 | 2 | 4.685147 | 4.158521 | 3.326275 | 3.278373 | −0.526627 | −0.0479028 |
| Mir374b | 95 | 13.753 | 2.129297 | 3.694545 | 20 | −1.533747 | 2.074000581 | 3.322424 | 3.296999 | 3.299109 | 3.264004 | −0.025425 | −0.035105 |
| S1fn9 | 3856 | 707.1334 | 260.8389 | 503.6897 | 1403 | −1.438823 | 1.477907871 | 10.27275 | 10.03349 | 9.766201 | 10.58595 | −0.239265 | 0.819748 |
| Angptl7 | 2062 | 657.8518 | 243.8045 | 75.12242 | 148 | −1.432038 | 0.521552843 | 10.7799 | 9.880377 | 7.959912 | 8.701876 | −0.899527 | 0.7419637 |
| Hpgds | 3298 | 442.3881 | 163.9559 | 139.1612 | 314 | −1.423721 | 0.92917316 | 8.843521 | 7.979495 | 7.67413 | 8.41057 | −0.864026 | 0.7364405 |
| Mir1942 | 63 | 8.022583 | 2.129297 | 1.231515 | 9 | −1.348715 | 1.514573173 | 4.685147 | 3.265544 | 3.267602 | 3.26844 | 0.0266104 | 0.0008375 |
| Mir5098 | 82 | 10.31475 | 3.193946 | 4.926061 | 13 | −1.331013 | 1.400005329 | | | | | | |
| Mir7227 | 59 | 8.022583 | 3.193946 | 3.694545 | 11 | −1.328727 | 1.574034729 | | | | | | |
| Mir6998 | 64 | 8.022583 | 1.064649 | 3.694545 | 7 | −1.325995 | 0.921958032 | 5.822144 | 5.183863 | 4.912472 | 4.772404 | −0.638281 | −0.1400683 |
| Mir7051 | 73 | 8.022583 | 3.193946 | 4.926061 | 8 | −1.13617 | 0.699565611 | 7.191504 | 7.056225 | 7.260203 | 7.086002 | −0.135278 | −0.1742007 |
| Mir495 | 63 | 9.168666 | 4.258595 | 0 | 10 | −1.106334 | 1.666576266 | 3.259129 | 4.696591 | 5.200319 | 3.239096 | 1.4374628 | −1.9612233 |
| Mir493 | 83 | 13.753 | 6.387892 | 2.46303 | 6 | −1.106334 | 0.533185164 | 3.421904 | 3.424454 | 3.784987 | 3.411307 | 0.0025499 | −0.3736805 |
| Mir1191 | 48 | 4.584333 | 1.064649 | 1.231515 | 6 | −0.933677 | 1.321928095 | 6.760612 | 6.601231 | 6.903372 | 6.566825 | −0.159381 | −0.3365466 |
| Esco2 | 2899 | 638.3684 | 340.6876 | 1002.453 | 2258 | −0.90594 | 1.171510397 | 9.207739 | 8.587471 | 10.14116 | 11.10211 | −0.620268 | 0.960952 |
| Mis18bp1 | 4016 | 1065.857 | 583.4275 | 1608.359 | 3411 | −0.869389 | 1.084605469 | 10.58738 | 9.737552 | 11.0634 | 11.99722 | −0.849831 | 0.933826 |
| Gm1321 | 1659 | 390.8144 | 213.9944 | 141.6242 | 398 | −0.868281 | 1.49070018 | 10.13245 | 10.1345 | 9.449467 | 10.28829 | 0.002055 | 0.838825 |
| Mir7679 | 63 | 5.730416 | 0 | 3.694545 | 11 | −0.863288 | 1.574034729 | 3.48823 | 3.449954 | 3.780704 | 3.713637 | −0.038276 | −0.0670666 |
| Fosb | 3776 | 632.638 | 353.4634 | 188.4218 | 561 | −0.839819 | 1.571142006 | 9.94288 | 9.576781 | 9.638586 | 9.760475 | −0.366099 | 0.121889 |
| Mki67 | 10075 | 11622.43 | 6596.563 | 20720.24 | 49360 | −0.817125 | 1.2523015 | 12.46468 | 11.61791 | 13.15096 | 14.35848 | −0.846768 | 1.207515 |
| Mir16-1 | 93 | 14.89908 | 8.517189 | 14.77818 | 34 | −0.806774 | 1.202065951 | 5.31474 | 4.572385 | 5.146516 | 4.361363 | −0.742355 | −0.7851535 |
| Mir758 | 81 | 25.21383 | 14.90508 | 14.77818 | 31 | −0.758411 | 1.068179442 | 3.734459 | 4.901372 | 4.208195 | 3.894968 | 1.166913 | −0.3132267 |
| Mab2212 | 2703 | 510.0071 | 303.4249 | 280.7855 | 631 | −0.749178 | 1.168171791 | 4.622257 | 4.602058 | 3.450657 | 4.780889 | −0.020199 | 1.3302319 |
| Hmgn5 | 1907 | 459.5794 | 274.6794 | 392.8533 | 944 | −0.742566 | 1.264796046 | 11.319 | 10.98621 | 11.3542 | 12.30016 | −0.332789 | 0.945956 |
| Cempf | 11122 | 3442.834 | 2081.388 | 6758.555 | 17142 | −0.726051 | 1.347748666 | 17.49855 | 17.52473 | 17.81146 | 17.69759 | 0.026178 | −0.113869 |
| Lepr | 6634 | 2470.956 | 1501.155 | 656.3976 | 2195 | −0.718996 | 1.741579112 | 10.00027 | 9.635223 | 8.240623 | 9.809648 | −0.365042 | 1.569025 |
| Cenpe | 7813 | 5023.438 | 3066.188 | 7757.314 | 18580 | −0.712184 | 1.260121396 | 12.70709 | 11.99821 | 13.27789 | 14.25452 | −0.708878 | 0.97663 |
| Mir485 | 73 | 17.19125 | 10.64649 | 7.389091 | 17 | −0.691297 | 1.202065951 | 8.934822 | 8.733295 | 8.856248 | 8.733786 | −0.201527 | −0.122462 |
| Mir1192 | 121 | 17.19125 | 10.64649 | 8.620606 | 21 | −0.691297 | 1.284528111 | 8.064611 | 7.964669 | 7.562276 | 7.705794 | −0.099942 | 0.1435179 |
| Snord93 | 45 | 20.6295 | 12.77578 | 16.0097 | 36 | −0.691297 | 1.169050894 | | | | | | |
| Mir568 | 83 | 28.65208 | 18.09903 | 4.926061 | 15 | −0.662728 | 1.606456206 | 3.977492 | 3.981847 | 3.580536 | 4.539328 | 0.0043547 | 0.9587916 |
| Nexn | 2564 | 1521.999 | 975.2182 | 545.5612 | 1358 | −0.64217 | 1.315760486 | 12.26247 | 11.96847 | 11.04659 | 12.18076 | −0.294999 | 1.13417 |
| Col10a1 | 3130 | 1654.944 | 1078.489 | 243.84 | 656 | −0.617771 | 1.427760995 | 11.3895 | 10.81998 | 8.55748 | 10.01221 | −0.569518 | 1.454732 |
| Mab2111 | 2778 | 648.6831 | 424.7948 | 263.5442 | 711 | −0.610748 | 1.431804374 | 4.12843 | 4.744737 | 3.277632 | 4.260902 | 0.6163063 | 0.9832697 |
| Kit20b | 5563 | 2320.819 | 1539.482 | 4078.778 | 9933 | −0.592189 | 1.284092449 | 10.84272 | 10.17806 | 11.68679 | 12.79319 | −0.664659 | 1.106394 |

TABLE 4-continued

Genes with differential expression levels from different mouse MEF, which are grouped according to the different pattern as shown in each tab.

| Gene/nc RNA | Length | RNA-seq | | | | fd D | Microarray | | | | fd D |
| | | WT | M8 knockout | TP53 knockout | D knockout | fd M8 knockout/WT | knockout/TP53 knockout | WT | M8 knockout | TP53 knockout | D knockout | fd M8 knockout/WT | knockout/TP53 knockout |
|---|---|---|---|---|---|---|---|---|---|---|---|---|---|
| Casc5 | 6525 | 1511.684 | 1003.964 | 2504.902 | 5319 | -0.590449 | 1.086400968 | 10.34177 | 9.617808 | 11.37677 | 12.21135 | -0.72396 | 0.834579 |
| Krt8 | 1805 | 386.2301 | 571.7163 | 836.1988 | 185 | 0.5658391 | -2.176320693 | 11.32854 | 11.73494 | 12.34269 | 10.49346 | 0.4064035 | -1.849228 |
| Cyp11a1 | 1774 | 1911.667 | 2852.194 | 1482.744 | 446 | 0.5772409 | -1.733154166 | 12.66737 | 13.0679 | 12.06807 | 10.69155 | 0.40053 | -1.376521 |
| Hdhd3 | 1083 | 254.4305 | 383.2735 | 310.3418 | 106 | 0.5911028 | -1.549793858 | 8.89848 | 9.167501 | 8.754346 | 8.071216 | 0.269021 | -0.68313 |
| Mmp13 | 2675 | 2484.709 | 3743.305 | 2498.744 | 985 | 0.5912359 | -1.343007625 | 12.52803 | 13.34984 | 12.65167 | 11.19244 | 0.821805 | -1.45923 |
| Lif | 4339 | 1234.332 | 1882.299 | 534.4776 | 236 | 0.6087656 | -1.179342572 | 11.57451 | 12.12065 | 10.0587 | 8.952517 | 0.546145 | -1.10618 |
| Wfdc2 | 708 | 22.92167 | 54.29708 | 317.7309 | 107 | 0.6171253 | -1.570194658 | 9.386927 | 10.29268 | 12.49976 | 11.1112 | 0.90756 | -1.378568 |
| Krt18 | 1400 | 997.0924 | 1587.391 | 1828.8 | 708 | 0.6708585 | -1.369076055 | 9.995646 | 10.5056 | 10.66998 | 9.144653 | 0.509958 | -1.525326 |
| Adh1 | 1334 | 741.5159 | 1180.695 | 785.7067 | 389 | 0.6710873 | -1.014220658 | 12.26041 | 13.0189 | 12.15236 | 11.43465 | 0.758484 | -0.717705 |
| Fbxo44 | 2150 | 284.2286 | 454.605 | 641.6194 | 271 | 0.6775615 | -1.24342491 | 7.932479 | 8.617592 | 8.998727 | 7.838338 | 0.685113 | -1.1603886 |
| Mir93 | 88 | 2.292167 | 7.452541 | 11.08364 | 4 | 0.7602288 | -1.332855867 | 7.650095 | 7.642487 | 7.937218 | 7.794076 | -0.007607 | -0.1431417 |
| Ppbp | 1080 | 289.9591 | 492.9323 | 124.383 | 55 | 0.7655404 | -1.177286159 | 10.95239 | 11.73024 | 9.620295 | 8.476621 | 0.777847 | -1.143674 |
| Mgarp | 1429 | 140.9682 | 257.645 | 168.7176 | 71 | 0.8700143 | -1.239604366 | 10.59295 | 11.22717 | 10.69838 | 9.512335 | 0.634223 | -1.1860488 |
| Krt14 | 1660 | 151.283 | 276.8087 | 189.6533 | 68 | 0.8716393 | -1.192181499 | 10.13439 | 10.84787 | 10.22518 | 9.323664 | 0.713472 | -0.901516 |
| Sprr1a | 790 | 53.86591 | 99.01233 | 174.8752 | 39 | 0.8782355 | -2.146400761 | 9.587798 | 10.64454 | 11.46023 | 9.946482 | 1.056744 | -1.513746 |
| Akr1e1 | 1713 | 700.2569 | 1330.811 | 1147.772 | 385 | 0.9263494 | -1.579058985 | 8.619576 | 9.570744 | 9.52195 | 7.64426 | 0.9511685 | -1.8776905 |
| Spus2 | 3404 | 223.4862 | 433.312 | 785.7067 | 272 | 0.9552202 | -1.530384162 | 9.391333 | 10.33809 | 10.95177 | 9.797504 | 0.946752 | -1.154263 |
| Crct1 | 717 | 3029.098 | 6240.971 | 370.6861 | 98 | 1.0428821 | -1.919344222 | 14.73334 | 15.63897 | 11.76094 | 10.10226 | 0.9056255 | -1.6586865 |
| Rnd1 | 2203 | 756.415 | 1732.183 | 1070.187 | 667 | 1.1953419 | -0.682103805 | 8.143776 | 8.031122 | 8.208756 | 7.684887 | -0.112654 | -0.523869 |
| Mir677 | 78 | 5.730416 | 13.84043 | 7.389091 | 5 | 1.2721772 | -0.563468795 | 6.432886 | 6.255704 | 7.290525 | 6.783655 | -0.177182 | -0.5068707 |
| Cdh16 | 3318 | 140.9682 | 405.6311 | 878.0703 | 169 | 1.2898545 | -2.37731322 | 9.306515 | 10.6415 | 11.85276 | 9.453857 | 1.334983 | -2.398907 |
| Gm53 | 617 | 537.513 | 1341.457 | 615.7576 | 288 | 1.3194295 | -1.096293673 | 8.95885 | 8.641918 | 8.017417 | 7.868243 | -0.316932 | -0.149174 |
| Mir193a | 66 | 4.584333 | 11.71114 | 20.93576 | 9 | 1.3553072 | -1.217972229 | 3.282251 | 3.283114 | 3.321942 | 3.302327 | 0.0008634 | -0.0196152 |
| Mir18 | 96 | 4.584333 | 12.77578 | 40.64 | 27 | 1.4123055 | -0.589941007 | 8.267056 | 7.955639 | 8.889686 | 8.432795 | -0.311417 | -0.456891 |
| Mir7036b | 63 | 1.146083 | 8.517189 | 17.24121 | 7 | 1.4350256 | -1.300434389 | 8.154861 | 8.121855 | 8.240585 | 8.12869 | -0.033065 | -0.111905 |
| Mir7090 | 62 | 3.43825 | 12.77578 | 16.0097 | 8 | 1.8936656 | -1.000874108 | 5.283343 | 5.350597 | 5.400565 | 5.387038 | 0.0672544 | -0.0135272 |

Example 7 Inhibition of Mettl8 Renders the Cell Resistant to Irradiation Treatment To further study the relationship between irradiation and Mettl8, the colony survival assays were performed on HCT116 wildtype and Mettl8 knockout cells. 500 cells per well of HCT116 control and Mettl8 knockout cells were seeded into 6-well plates in triplicate and subjected to different dosage of irradiation (0Gy, 1 Gy, 3Gy, and 5Gy). A week later, the survival cell colonies were fixed and stained with crystal violet. Colonies with more than 50 cells were counted.

Figure 12:
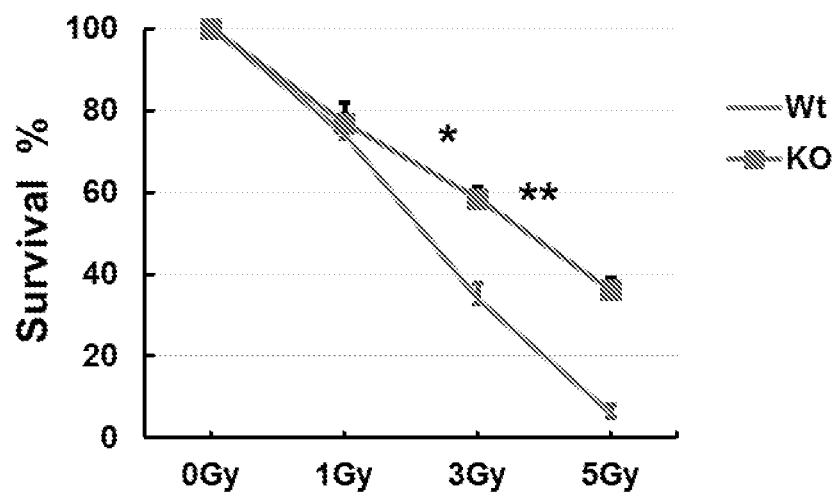
FIG. 12 shows that inhibition of Metl18 protected tissues from irradiation caused cell death.

The result was presented in ±SEM of percentage of colonies survived compared to untreated samples. As shown in FIG. 12, Mettl8 knockout cells had higher survival rate under irradiation compared to the wide type.

EQUIVALENTS

It is to be understood that while the disclosure has been described in conjunction with the above embodiments, the foregoing description and examples are intended to illustrate and not limit the scope of the disclosure. Other aspects, advantages, and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs.

The embodiments illustratively described herein may suitably be practiced in the absence of any element or elements, limitation, or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that, although the present disclosure has been specifically disclosed by specific embodiments and optional features, modification, improvement, and variation of the embodiments herein disclosed may be resorted to by those skilled in the art, and that such modifications, improvements, and variations are considered to be within the scope of this disclosure. The materials, methods, and examples provided here are representative of particular embodiments, are exemplary, and are not intended as limitations on the scope of the disclosure.

The scope of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method of inhibiting proliferation of a cell, inhibiting $m^3C$ formation in a cell, modulating R-Loop level in a cell, inhibiting Mettl8 activity in a cell, or activating ATM and p53 in a cell, the method comprising contacting the cell with a Mettl8 inhibitor; wherein the Mettl8 inhibitor is a CRISPR-Cas system directed to a Mettl8 gene or an shRNA directed to a Mettl8 gene; wherein the CRISPR-Cas system comprises at least one guide RNA (gRNA) comprising a polynucleotide sequence of SEQ ID No: 9, SEQ ID No: 10, SEQ ID No: 11, SEQ ID No: 12, SEQ ID No: 13, or SEQ ID No: 14; wherein the shRNA comprises a polynucleotide sequence of SEQ ID No: 2, SEQ ID No: 3, SEQ ID No: 4, SEQ ID No: 5, SEQ ID No: 6, SEQ ID No: 7, SEQ ID No: 8, or SEQ ID No: 15.

2. The method of claim 1, wherein the CRISPR-Cas system or the shRNA are encoded by one or more recombinant vectors.

3. The method of claim 2, wherein the recombinant vector is a retroviral vector, a lentiviral vector, a murine leukemia viral ("MLV") vector, an Epstein-Barr viral ("EBV") vector, an adenoviral vector, a herpes viral ("HSV") vector, or an adeno-associated viral ("AAV") vector.

4. The method of claim 1, wherein the Mettl8 inhibitor is a CRISPR-Cas system, wherein the gRNA comprises a polynucleotide sequence of SEQ ID No 9, SEQ ID No 10, SEQ ID No 11, SEQ ID No 12, SEQ ID No 13, or SEQ ID No 14.

5. The method of claim 1, wherein the Mettl8 inhibitor is an shRNA comprising a polynucleotide sequence of SEQ ID No. 2, SEQ ID No. 3, SEQ ID No. 4, SEQ ID No. 5, SEQ ID No. 6, SEQ ID No. 7, SEQ ID No. 8, or SEQ ID No. 15.

6. The method of claim 1, wherein the cell is a cancer cell.

7. The method of claim 1, wherein the cell is a mammalian cell.

8. The method of claim 7, wherein the mammalian cell is from a mammal selected from the group consisting of a mouse, a rat, a guinea pig, a non-human primate, a dog, a cat, a horse, a cow, a pig, a goat, a sheep, and/or human.

* * * * *

SEQUENCE LISTING

```
<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gatttagact aggtagaga                                                  19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttgagggaa tttcctgaaa t                                               21

<210> SEQ ID NO 3
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 3
gcgagagaat catcatggga t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtgctacaaa tcgtttctca a                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatcgccgct tacaagttaa t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctccttgtgt ctccgtttaa a                                              21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tttgtgctta ggatggccc                                                 19

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gatccccggg ccatcctaag cacaaattca agagatttgt gcttaggatg gcccttttta   60

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
taacttttta ggtactgctt                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ctcagctgtg cgagtccttc                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gaaggcgaga gaatcatcat                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aagtttttga acacaacatg                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
agttttgtct cgccagaacc                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gggaagacag agccgtttcc                                               20

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 15
ccgggttgag ggaatttcct gaaatctcga gatttcagga aattccctca actttttg    59

<210> SEQ ID NO 16
<211> LENGTH: 9
<212> TYPE: PRT
<213> ORGANISM: Unknown
<220> FEATURE:
<223> OTHER INFORMATION: Description of Unknown:
      SAM domain sequence

<400> SEQUENCE: 16

Ile Leu Glu Val Gly Cys Gly Ala Gly
1               5

<210> SEQ ID NO 17
<211> LENGTH: 27
<212> TYPE: DNA
<213> ORGANISM: Unknown
<220> FEATURE:
<223> OTHER INFORMATION: Description of Unknown:
      SAM domain sequence

<400> SEQUENCE: 17
atactagagg ttggttgtgg agctgga    27

<210> SEQ ID NO 18
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asn Met Ile Trp Arg Asn Ser Ile Ser Cys Leu Arg Leu Gly Lys
1               5                   10                  15

Val Pro His Arg Tyr Gln Ser Gly Tyr His Pro Val Ala Pro Leu Gly
                20                  25                  30

Ser Arg Ile Leu Thr Asp Pro Ala Lys Val Phe Glu His Asn Met Trp
            35                  40                  45

Asp His Met Gln Trp Ser Lys Glu Glu Glu Ala Ala Ala Arg Lys Lys
        50                  55                  60

Val Lys Glu Asn Ser Ala Val Arg Val Leu Leu Glu Glu Gln Val Lys
65                  70                  75                  80

Tyr Glu Arg Glu Ala Ser Lys Tyr Trp Asp Thr Phe Tyr Lys Ile His
                85                  90                  95

Lys Asn Lys Phe Phe Lys Asp Arg Asn Trp Leu Leu Arg Glu Phe Pro
            100                 105                 110

Glu Ile Leu Pro Val Asp Gln Lys Pro Glu Glu Lys Ala Arg Glu Ser
        115                 120                 125

Ser Trp Asp His Val Lys Thr Ser Ala Thr Asn Arg Phe Ser Arg Met
    130                 135                 140

His Cys Pro Thr Val Pro Asp Glu Lys Asn His Tyr Glu Lys Ser Ser
145                 150                 155                 160

Gly Ser Ser Glu Gly Gln Ser Lys Thr Glu Ser Asp Phe Ser Asn Leu
                165                 170                 175

Asp Ser Glu Lys His Lys Lys Gly Pro Met Glu Thr Gly Leu Phe Pro
            180                 185                 190

```
Gly Ser Asn Ala Thr Phe Arg Asn Ser Val Phe Pro Ile Leu Asn Thr
            195                 200                 205

Leu Glu Asn Ser Pro Glu Ser Phe Leu Tyr Cys Cys Asp Phe Ala Ser
    210                 215                 220

Gly Ala Val Glu Leu Val Lys Ser His Ser Ser Tyr Arg Ala Thr Gln
225                 230                 235                 240

Cys Phe Ala Phe Val His Asp Val Cys Asp Asp Gly Leu Pro Tyr Pro
                245                 250                 255

Phe Pro Asp Gly Ile Leu Asp Val Ile Leu Leu Val Phe Val Leu Ser
                260                 265                 270

Ser Ile His Pro Asp Arg Met Gln Gly Val Val Asn Arg Leu Ser Lys
            275                 280                 285

Leu Leu Lys Pro Gly Gly Met Leu Leu Phe Arg Asp Tyr Gly Arg Tyr
    290                 295                 300

Asp Lys Thr Gln Leu Arg Phe Lys Lys Gly His Cys Leu Ser Glu Asn
305                 310                 315                 320

Phe Tyr Val Arg Gly Asp Gly Thr Arg Ala Tyr Phe Phe Thr Lys Gly
                325                 330                 335

Glu Val His Ser Met Phe Cys Lys Ala Ser Leu Asp Glu Lys Gln Asn
            340                 345                 350

Leu Val Asp Arg Arg Leu Gln Val Asn Arg Lys Lys Gln Val Lys Met
    355                 360                 365

His Arg Val Trp Ile Gln Gly Lys Phe Gln Lys Pro Leu His Gln Thr
370                 375                 380

Gln Asn Ser Ser Asn Met Val Ser Thr Leu Leu Ser Gln Asp
385                 390                 395

<210> SEQ ID NO 19
<211> LENGTH: 1197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgaatatga tttggagaaa ttccatttct tgtctaaggc taggaaaggt gccacacaga      60
taccaaagtg gttaccaccc agtggcccct ctgggatcaa ggattttaac tgacccagcc    120 aaagttttg  aacacaacat gtgggatcac atgcagtggt ctaaggaaga agaagcagca    180
gccagaaaaa aagtaaaaga aaactcagct gtgcgagtcc ttctggaaga gcaagttaag    240
tatgagagag aagctagtaa atactgggac acatttttaca agattcataa gaataagttt    300
ttcaaggatc gtaattggct gttgagggaa tttcctgaaa ttcttccagt tgatcaaaaa    360
cctgaagaga aggcgagaga atcatcatgg gatcatgtaa aaactagtgc tacaaatcgt    420
ttctcaagaa tgcactgtcc tactgtgcct gatgaaaaaa atcattatga aaaagttct     480 ggttcttcag aaggtcaaag caaaacagaa tctgattttt ccaacctaga ctctgaaaaa    540
cacaaaaaag gacctatgga gactggattg tttcctggta gcaatgccac tttcaggaat    600
agtgtgtttc caatttttgaa cactttggag aactctccgg agtcctttct gtattgttgt    660
gattttgctt ctggagctgt ggagctcgta aagtcacact cgtcctacag agcaacccag    720
tgttttgcct tgttcatga  tgtatgtgat gatggcttac cttaccctt  tccagatggg    780 atcctgatc  tcattctcct tgtctttgtg ctctcttcta ttcatcctga caggatgcaa    840
ggtgttgtaa accgactgtc caagttactg aaacctgggg gaatgctgtt atttcgagac    900
```

```
tatggaagat atgataagac tcagcttcgt tttaaaaagg gacattgttt atctgaaaat    960
ttttatgttc gaggagatgg taccagagca tatttcttta caaaagggga agtccacagt   1020
atgttctgca agccagtttt agatgaaaag caaaatctgg ttgatcgccg cttacaagtt   1080
aataggaaaa aacaagtgaa aatgcaccga gtgtggattc aaggcaaatt ccagaaacca   1140
ttgcaccaga ctcagaatag ctccaatatg gtatctacac tcctttcaca agactga      1197
```

<210> SEQ ID NO 20
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
agtgcattct tgagaaacga tttgtagcac tagttttttac atgatgattc tctcgccttc    60
tcttcaggtt tttgatcaac tggaagaatt                                      90
```

<210> SEQ ID NO 21
<211> LENGTH: 98
<212> TYPE: DNA
<213> ORGANISM: Homo sapiens

<400> SEQUENCE: 21

```
agtgcattct tgagaaacga tttgtagcac tagttttttac atgatcccat gatgattctc    60
tcgccttctc ttcaggtttt tgatcaactg gaagaatt                             98
```

<210> SEQ ID NO 22
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

```
gcagccagaa aaaagtaaa agaaaactca gctgtgaaga gcaaggtagt caactgcgtg      60
ctgtagctcc tagagccaga gcttt                                           85
```

<210> SEQ ID NO 23
<211> LENGTH: 98
<212> TYPE: DNA
<213> ORGANISM: Homo sapiens

<400> SEQUENCE: 23

```
gcagccagaa aaaagtaaa agaaaactca gctgtgcgag tccttctgga agagcaaggt      60
agtcaactgc gtgctgtagc tcctagagcc agagcttt                             98
```

<210> SEQ ID NO 24
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

```
ctgtttaatc tatgttgact aattaatcat ttgtaactct taggatgaat atgatttgga    60
gaaattccat tcttgtcta aggcta                                          86
```

<210> SEQ ID NO 25
<211> LENGTH: 98
<212> TYPE: DNA
<213> ORGANISM: Homo sapiens

<400> SEQUENCE: 25
ctgtttaatc tatgttgact aattaatcat ttgtaacttt ttaggtactg cttaggatga    60
atatgatttg gagaaattcc atttcttgtc taaggcta                            98

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tcgaggattt taactgaccc cgccaaagtt tttgaacaca acatgtg                  47

<210> SEQ ID NO 27
<211> LENGTH: 104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
gagagttttg tctcgccaga acctgggagc agaggacggt ctgctcctga ccccgacttg    60
gaagaataca gcaaaggacc tgggaagaca gagccgtttc ctgg                    104

<210> SEQ ID NO 28
<211> LENGTH: 600
<212> TYPE: DNA
<213> ORGANISM: Mus musculus

<400> SEQUENCE: 28
ctctgtttta gttaagtttg aaagtgacgc taacaaatac tgggatatat tttaccagac    60
ccataagaat aagttttca agaatcgtaa ttggctgttg agggaatttc ctgaaatcct   120
tcctgttaat caaacacta aagagaaagt gggagaatca tcctgggatc aagtcggaag   180
cagcatctct aggacacaag gaacagaaac ccattgtcaa gagagttttg tctcgccaga   240
acctgggagc agaggacggt ctgctcctga ccccgacttg gaagaataca gcaaaggacc   300
tgggaagaca gagccgtttc ctggtagcaa tgccactttt cgaatactag aggtactgta   360
tgagagtgtg tagcccacgc tattttatga gtggtccaga ctgtccaggt ggaaagatca   420
gatctaatta aatgcttagt gttcttacat gcataagtaa tacttcaggg actttaatca   480
gtcaagtttt aagcttgtgg ctttaatttc atctatgtta ctttttttt ttctttaat     540 ttgttgttat ttctaactta gaggcagtat ttaagtcctg gtacattttt ggtccaaatt   600

<210> SEQ ID NO 29
<211> LENGTH: 15
<212> TYPE: DNA
<213> ORGANISM: Homo sapiens

<400> SEQUENCE: 29
catttcccgg tgaga                                                   15

```
<210> SEQ ID NO 30
<211> LENGTH: 15
<212> TYPE: DNA
<213> ORGANISM: Macaca mulatta

<400> SEQUENCE: 30
catttcccgg tgaga                                                     15

<210> SEQ ID NO 31
<211> LENGTH: 15
<212> TYPE: DNA
<213> ORGANISM: Mus musculus

<400> SEQUENCE: 31
catttccggg agagg                                                     15

<210> SEQ ID NO 32
<211> LENGTH: 15
<212> TYPE: DNA
<213> ORGANISM: Canis lupus familiaris

<400> SEQUENCE: 32
cacttcccgg tgagg                                                     15

<210> SEQ ID NO 33
<211> LENGTH: 15
<212> TYPE: DNA
<213> ORGANISM: Loxodonta africana

<400> SEQUENCE: 33
catttcccgg tgagg                                                     15

<210> SEQ ID NO 34
<211> LENGTH: 98
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: misc_feature
<222> LOCATION: (46)..(53)
<223> OTHER INFORMATION: This region may or may not be present in its
      entirety

<400> SEQUENCE: 34
agtgcattct tgagaaacga tttgtagcac tagtttttac atgatccat gatgattctc      60 tcgccttctc ttcaggtttt tgatcaactg gaagaatt                             98

<210> SEQ ID NO 35
<211> LENGTH: 98
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: misc_feature
<222> LOCATION: (37)..(49)
<223> OTHER INFORMATION: This region may or may not be present in its
      entirety

<400> SEQUENCE: 35
gcagccagaa aaaagtaaa agaaaactca gctgtgcgag tccttctgga agagcaaggt      60
agtcaactgc gtgctgtagc tcctagagcc agagcttt                             98
```

```
<210> SEQ ID NO 36
<211> LENGTH: 98
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: misc_feature
<222> LOCATION: (39)..(50)
<223> OTHER INFORMATION: This region may or may not be present in its
      entirety

<400> SEQUENCE: 36
ctgtttaatc tatgttgact aattaatcat ttgtaacttt ttaggtactg cttaggatga    60
atatgatttg gagaaattcc atttcttgtc taaggcta                           98
```